(12) United States Patent
Qin et al.

(10) Patent No.: US 11,597,774 B2
(45) Date of Patent: Mar. 7, 2023

(54) ANTIBODY VARIABLE DOMAINS AND ANTIBODY CONSTRUCTS

(71) Applicants: CITY OF HOPE, Duarte, CA (US); BOARD OF REGENTS, THE UNIVERSITY OF TEXAS SYSTEM, Austin, TX (US)

(72) Inventors: Hong Qin, Upland, CA (US); Larry W. Kwak, Pasadena, CA (US); Guowei Wei, San Dimas, CA (US)

(73) Assignees: CITY OF HOPE, Duarte, CA (US); BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 206 days.

(21) Appl. No.: 16/610,868

(22) PCT Filed: May 4, 2018

(86) PCT No.: PCT/US2018/031239
§ 371 (c)(1),
(2) Date: Nov. 4, 2019

(87) PCT Pub. No.: WO2018/204876
PCT Pub. Date: Nov. 8, 2018

(65) Prior Publication Data
US 2020/0071418 A1 Mar. 5, 2020

Related U.S. Application Data

(60) Provisional application No. 62/501,649, filed on May 4, 2017.

(51) Int. Cl.
*C07K 16/30* (2006.01)
*A61P 35/00* (2006.01)
*A61K 39/395* (2006.01)

(52) U.S. Cl.
CPC .... *C07K 16/3061* (2013.01); *A61K 39/39558* (2013.01); *A61P 35/00* (2018.01); *C07K 2317/21* (2013.01); *C07K 2317/24* (2013.01); *C07K 2317/31* (2013.01); *C07K 2317/35* (2013.01); *C07K 2317/522* (2013.01); *C07K 2317/524* (2013.01); *C07K 2317/526* (2013.01); *C07K 2317/55* (2013.01); *C07K 2317/565* (2013.01); *C07K 2317/622* (2013.01); *C07K 2319/30* (2013.01)

(58) Field of Classification Search
CPC ............ C07K 16/3061; C07K 2317/21; C07K 2319/30; A61K 39/39558
See application file for complete search history.

(56) References Cited

U.S. PATENT DOCUMENTS

| 4,676,980 | A | 6/1987 | Segal et al. |
| 4,816,567 | A | 3/1989 | Cabilly et al. |
| 4,946,778 | A | 8/1990 | Ladner et al. |
| 6,180,370 | B1 | 1/2001 | Queen et al. |
| 2006/0115486 | A1 | 6/2006 | Pier et al. |
| 2010/0120627 | A1 | 5/2010 | Belouchi et al. |
| 2015/0086601 | A1 | 3/2015 | Rey et al. |
| 2020/0354452 | A1* | 11/2020 | Qin .................... C07K 16/3061 |

FOREIGN PATENT DOCUMENTS

| WO | WO93/08829 A1 | 5/1993 |
| WO | WO2010/111254 A1 | 9/2010 |
| WO | WO2010/111254 A9 | 9/2010 |
| WO | WO2015/189638 A2 | 12/2015 |
| WO | WO2015/189638 A3 | 12/2015 |

OTHER PUBLICATIONS

Holliger et al., Engineered antibody fragments and the rise of single domains, Nature Biotech., 23 (9) 1126-1136 (Year: 2005).*
Saeed et al., Antibody engineering for pursuing a healthier future, Frontiers in Microbiology, vol. 8, article 495 (Year: 2017).*
Targeted Cancer Therapies, retrieved from https://www.cancer.gov/about-cancer/treatment/types/targeted-therapies/targeted-therapies-fact-sheet, Sep. 1, 2021 (Year: 2021).*
Gura, T., Systems for Identifying New Drugs Are Often Faulty, Science, 1997, 278:1041-1042 (Year: 1997).*
Kaiser, J., First pass at cancer genoome reveals complex landscape, Science, 2006, 313:1370 (Year: 2006).*
Bird et al., Single-Chain Antigen-Binding Proteins, Science, vol. 242, pp. 423-426, Publication Date: Oct. 21, 1998 (Year: 1998).*
International Search Report dated Aug. 3, 2018, for PCT/US2018/031239, filed May 4, 2018, 3 pages.
Marks, J.D. et al. (Jul. 1992). "By-passing immunization: building high affinity human antibodies by chain shuffling," *Biotechnology* 10(7):779-783.
McCafferty, J. et al. (Dec. 6, 1990). "Phage antibodies: filamentous phage displaying antibody variable domains," *Nature* 348(6301):552-554.

(Continued)

*Primary Examiner* — Peter J Reddig
*Assistant Examiner* — Cheng Lu
(74) *Attorney, Agent, or Firm* — Mintz Levin Cohn Ferris Glovsky and Popeo, P.C.

(57) ABSTRACT

Provided herein are, inter alia, compositions and methods for the treatment of cancer. The compositions include, for example, an antibody variable domain or antibody construct, inter alia, useful for targeting and killing cancer cells. Due to their ability to differentially bind cancer cells versus non-cancer cells, the compositions provided herein may be used, for example, for therapeutic and diagnostic purposes.

16 Claims, 30 Drawing Sheets

Specification includes a Sequence Listing.

(56) References Cited

OTHER PUBLICATIONS

Traunecker, A. (Dec. 1991). "Bispecific single chain molecules (Janusins) target cytotoxic lymphocytes on HIV infected cells," *EMBO J* 10(12):3655-3659.
Written Opinion dated Aug. 3, 2018, for PCT/US2018/031239, filed May 4, 2018, 3 pages.

* cited by examiner

Lane 1: Protein A-purified recombinant 4-4 LCmFc-Ab
Lane 2: Protein A-purified recombinant 4-4 LC-Ab
Lane 3: Protein A-purified recombinant 4-4 (LC)$_2$-Ab
Lane 4: Protein A-purified recombinant 4-4 LCFv-Ab

|  | CDR3 |
| --- | --- |
| 4-4 VL | XXWDXXXXX |
| 4-4 VL Mutant | XXASXXXXX |

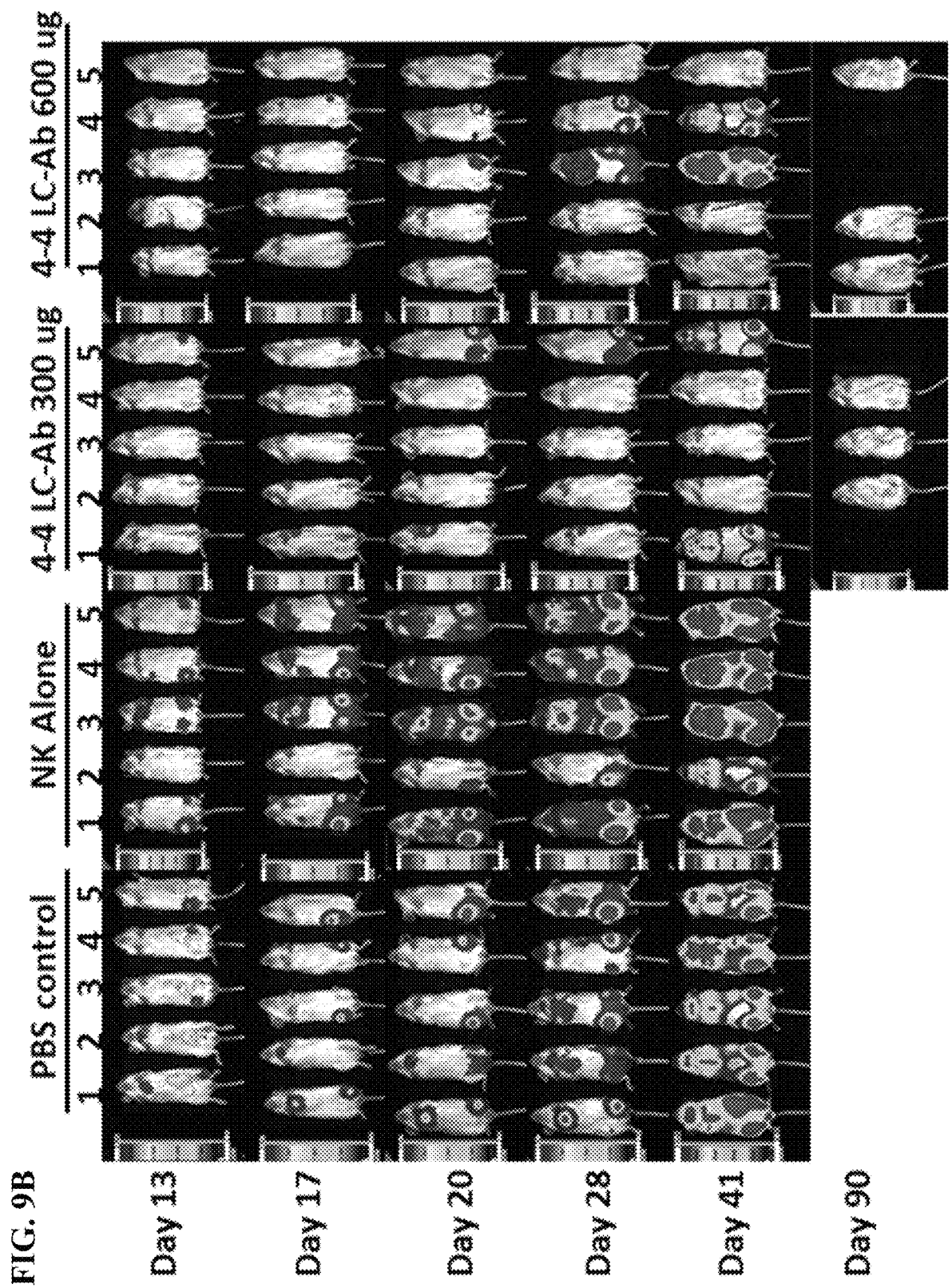

ANTIBODY VARIABLE DOMAINS AND ANTIBODY CONSTRUCTS

CROSS-REFERENCES TO RELATED APPLICATIONS

This application is a National Stage filing of International Patent Application No. PCT/US2018/031239, filed May 4, 2018, which claims the benefit of U.S. Provisional Application No. 62/501,649, filed May 4, 2017, the contents of which are incorporated herein by reference in their entireties and for all purposes.

REFERENCE TO A "SEQUENCE LISTING," A TABLE, OR A COMPUTER PROGRAM LISTING APPENDIX SUBMITTED AS AN ASCII FILE

The Sequence Listing written in file 048440-660001WO_ST25.TXT, created May 4, 2018, 10,446 bytes, machine format IBM-PC, MS Windows operating system, is hereby incorporated by reference.

BACKGROUND

New cancer immunotherapies are rapidly entering the clinic due to their promising potency. Monoclonal antibodies and antibody-based immunotherapeutics are particularly attractive platforms due to their high specificity and proven antitumor effects. Immunotherapeutics currently under development have been designed against a range of targets; however these tumor-associated targets are often expressed by both cancer and healthy cells. Consequently, these immunotherapeutic agents inevitably deplete healthy cells in the process of eliminating tumors. Thus, there is a need in the art for immunotherapeutics that can distinguish and selectively kill cancer cells while leaving healthy cells unharmed. Provided herein are, inter alia, antibody constructs and methods of using the same addressing these and other problems in the art.

BRIEF SUMMARY OF THE INVENTION

In an aspect is provided an antibody variable domain including a CDR 1 as set forth in SEQ ID NO:1, a CDR 2 as set forth in SEQ ID NO:2 and a CDR 3 as set forth in SEQ ID NO:3.

In another aspect is provided an antibody construct including a first antibody peptide, the first antibody peptide including: (i) a first antibody variable domain including a CDR 1 as set forth in SEQ ID NO:1, a CDR 2 as set forth in SEQ ID NO:2 and a CDR 3 as set forth in SEQ ID NO:3; and (ii) a first antibody domain bound to the first antibody variable domain.

In one aspect, an isolated nucleic acid encoding the antibody variable domain provided herein including embodiments thereof is provided.

In another aspect, an isolated nucleic acid encoding the first antibody peptide provided herein including embodiments thereof is provided.

In another aspect, an isolated nucleic acid encoding the second antibody peptide provided herein including embodiments thereof is provided.

In another aspect, an isolated nucleic acid encoding the first light chain antibody peptide provided herein including embodiments thereof is provided.

In another aspect, an isolated nucleic acid encoding the second light chain antibody peptide provided herein including embodiments thereof is provided.

In one aspect, a pharmaceutical composition including a therapeutically effective amount of the antibody variable domain provided herein including embodiments thereof and a pharmaceutically acceptable excipient is provided.

In another aspect, a pharmaceutical composition including a therapeutically effective amount of the antibody construct provided herein including embodiments thereof and a pharmaceutically acceptable excipient is provided.

In one aspect is provided a method for treating cancer in a subject in need thereof, the method including administering to a subject a therapeutically effective amount of the antibody variable domain provided herein including embodiments thereof, thereby treating cancer in the subject.

In another aspect is provided a method for treating cancer in a subject in need thereof, the method including administering to a subject a therapeutically effective amount of the antibody construct provided herein including embodiments, thereby treating cancer in the subject.

BRIEF DESCRIPTION OF THE DRAWINGS

FIG. 1C: FACS histogram displaying 4-4 phage binding specificity based on staining different lymphoma cell lines: mantle cell lymphoma (MCL) lines—JeKo-1, Mino, MAVER-1, and NCEB-1; non-MCL lines—HBL-1 (diffused large b-cell lymphoma, DLBCL), RL (follicular lymphoma, FL), Raji (Burkitt lymphoma, BL), and BJAB (BL). Serially titrated 4-4 phage clone was detected by FITC conjugated anti-M13 phage antibody and unstained cells were used as a negative control.

FIG. 2A: Schematic diagram of four recombinant 4-4 human antibody variants (antibody constructs) engineered and implemented throughout the study. Monospecific VL represent the identified 4-4 VL sequence. Heavy and light chain constant Fc regions (CH2 and CH3) were based on respective murine and human IgG1. Divalent VL murine Fc fusion antibody construct was termed "LCmFc-Ab." Divalent VL human Fc fusion antibody construct was termed "LC-Ab." Tetravalent, linker-connected bi-VL human Fc fusion antibody construct was termed "(LC)$_2$-Ab." Tetravalent, VL-substituted Fv human IgG antibody construct was termed "LCFv-Ab. " FIG. 2B: SDS gel image of protein A affinity purified recombinant 4-4 antibody variants (antibody constructs).

FIG. 3A: Serially titrated LCmFc-Ab on JeKo-1 cells. FIG.

3B: 200 ng LCmFc-Ab/10⁶ cells on MCL lines (JeKo-1, Mino, MAVER-1, NCEB-1, and REC-1); and non-MCL lines [HBL-1 (DLBCL), RL (FL), Raji (BL), BJAB (BL), and Jurkat (T-cell lymphoma)]. FIG. 3C: 10 ng LCmFc-Ab/10⁶ cells on JeKo-1 (MCL) and PBMC purified normal human B and T lymphocytes, and gated myeloid cells FIGS. 4A-4B. 4-4 VL binding specificity confirmed by point mutations.

(FIG. 6B) four MCL primary patient samples. FIG. 6C: Specific lysis with the use of human antibody variants depicted in FIGS. 2A and 2B over varying concentrations.

FIG. 7A: Results of chromium-51 (⁵¹Cr) release assays. Specific lysis measured target (T) cell lysis by effector (E) NK cells at E:T ratio 20:1. Specific lysis of normal B cells was determined with the addition of 4-4 LC Ab construct. Rituximab, antibody alone, or NK cells alone were used as controls. FIG. 7B: Human PBMC was incubated for 24 h with serially diluted 4-4 LC-Ab construct. Rituximab and irrelevant antibodies were used as controls. FACS plots of human B cells from PBMC stained with anti-CD20-APC.

FIG. 8A: FACS plots of anti-CD20-APC gated human B cells from humanized mice administered via IV injection 200 μg/mouse of single agent antibody treatment (4-4 LC-Ab). Blood was sampled by retro-orbital bleeds on days −1, 1, and 3 of the antibody treatment. FACS plots are representative of n=4 mice per treatment groups. Control groups were administered rituximab or irrelevant control antibody. FIG. 8B: Line plot displaying the mean and standard deviation of the percent of CD20+B cells in CD45 gated human leukocytes in each treatment group with respect to the control Ab group.

FIGS. 9A-9J. In vivo characterization of MCL-specific antibody construct's biological functions. FIG. 9A: Treatment schedule of 4-4 antibody construct treatment in MCL model. NSG mice were IV challenged with a minimum lethal dose of tumor cells and randomized into groups of n=5. Each mouse was administered 600 μL IV injections of antibody with 10×10⁶ NK cells and 5×10⁴ IU IL2. Control mice were administered PBS or NK cells alone. Treatment occurred on Day 3, 8, 13, and 18. Tumor cells were engineered to express red luciferase which allowed tumor growth to be monitored using bioluminescent imaging. FIGS. 9B-9D: Bioluminescent images of tumors in MCL tumor xenograft mice following antibody construct treatment. FIGS. 9E-9J: Tumor-free (FIGS. 9E, 9G, 9I) and overall (FIGS. 9F, 9H, 9J) survival curves for tumor xenograft mice treated with 4-4 antibody construct tracked for 90 days. **P<0.001. FIGS. 9B and 9E: Experimental groups compared 4-4 LC-Ab dosing effects between 300 μg and 600 μg per treatment in Z-138 ibrutinib-resistant MCL model. Images taken on days 13, 17, 20, 28, 41 and 90 after tumor challenge are shown. FIGS. 9C and 9F: Experimental groups compared 300 μg antibody treatment of 4-4 LC-Ab to 4-4 LCFv-Ab construct in a Z-138 ibrutinib-resistant MCL model. Images on days 14, 24, 34, 50, 70, and 80 after tumor challenge are shown. FIGS. 9D and 9G: Experimental groups compared 300 antibody treatment of 4-4 LC-Ab construct to 4-4 LCFv-Ab construct in a JeKo-1-CD20-KO rituximab-resistant MCL model. Images on days 15, 26, 38, 50, 70, and 90 after tumor challenge are shown. Additional rituximab negative control was added.

DETAILED DESCRIPTION

Figure 1A:
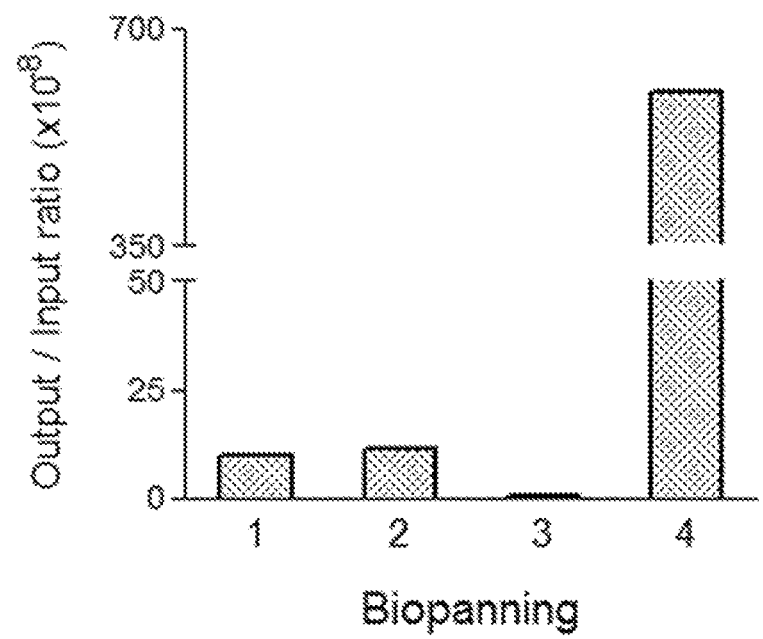
FIGS. 1A-1C. Identification and characterization of mantle cell lymphoma-specific antibody phage clones. A human antibody phage library was filtered to exclude phages that bound normal human B cells. The filtered library was then used to screen human mantle cell lymphoma line Jeko-1. Phages bound to JeKo-1 cells were eluted, tittered, and amplified for the subsequent rounds of biopanning. Biopanning enrichment results were expressed in phage "Output/input ratio" ($\times 10^{-8}$) (FIG. 1A) or "Number of phages/$10^6$ cells" (FIG. 1B) for each of the four biopanning rounds. Predominantly enriched phage clone (4-4) containing a variable binding domain of light chain (VL) was identified.
Figure 1B:
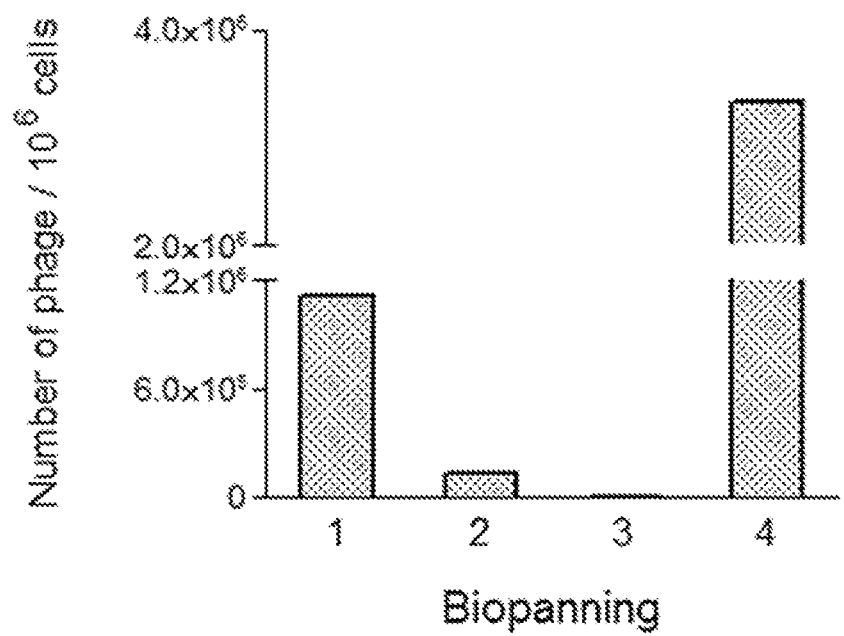
Figure 1C:
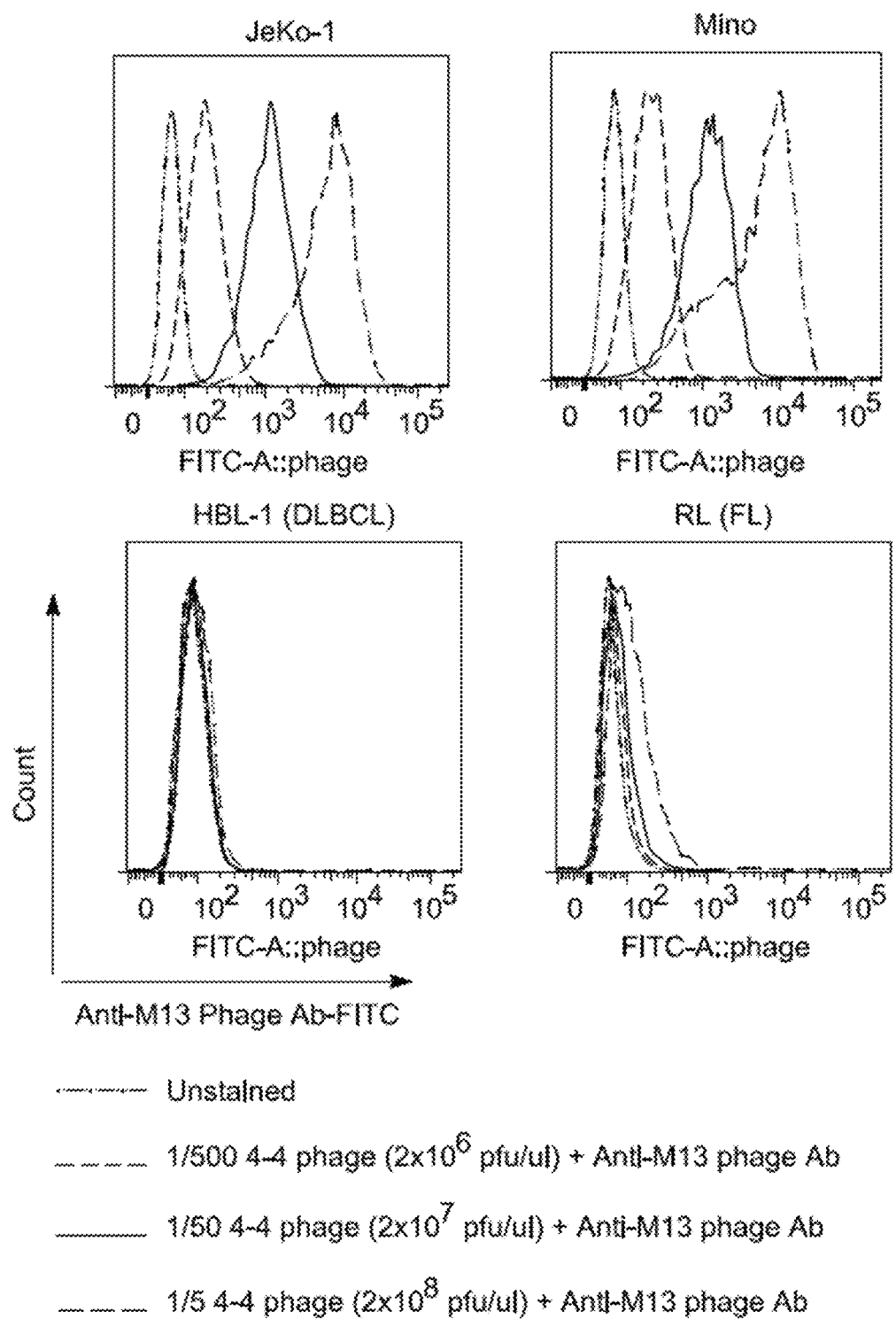
Figure 1C:
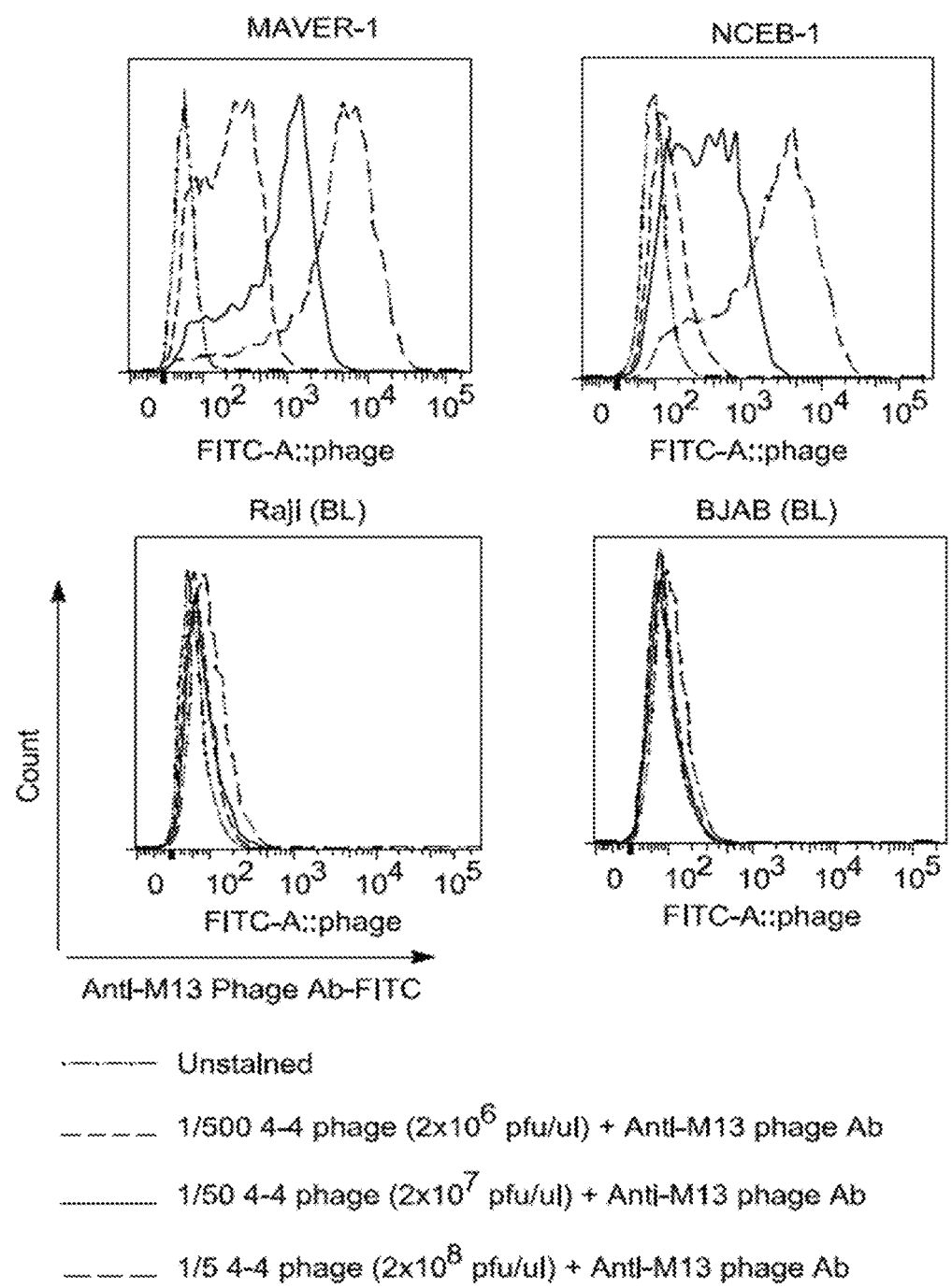

While various embodiments and aspects of the present invention are shown and described herein, it will be obvious to those skilled in the art that such embodiments and aspects are provided by way of example only. Numerous variations, changes, and substitutions will now occur to those skilled in the art without departing from the invention. It should be understood that various alternatives to the embodiments of the invention described herein may be employed in practicing the invention.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The abbreviations used herein have their conventional meaning within the chemical and biological arts. The chemical structures and formulae set forth herein are constructed according to the standard rules of chemical valency known in the chemical arts.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., C$_1$-C$_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene.

The term "heteroalkyl," by itself or in combination with another term, means, unless otherwise stated, a stable non-cyclic straight or branched chain, or combinations thereof, including at least one carbon atom and at least one heteroatom (e.g. O, N, P, Si or S) and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two or three heteroatoms may be consecutive, such as, for example, —CH$_2$—NH—OCH$_3$ and —CH$_2$—O—Si(CH$_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo(C$_1$-C$_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

The term "oxo," as used herein, means an oxygen that is double bonded to a carbon atom.

The term "alkylsulfonyl," as used herein, means a moiety having the formula $-S(O_2)-R'$, where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R")=NR'", —S(O)R', —S(O)$_2$R', —S(O)$_2$N(R)('R"—NRSO$_2$R'), —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", NR"C(O)$_2$R', NRC(NR'R")=NR'", S(O)R', —S(O)$_2$R', —S(O)$_2$N(R')(R", —NRSO$_2$R), —CN, —NO$_2$, —R', —N$_3$, —CH(Ph)$_2$, fluoro($C_1$-$C_4$)alkoxy, and fluoro ($C_1$-$C_4$)alkyl, in a number ranging from zero to the total number of open valences on the aromatic ring system; and where R', R'', R''', and R'''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R'', R''', and R'''' groups when more than one of these groups is present.

Where a moiety is substituted with an R substituent, the group may be referred to as "R-substituted." Where a moiety is R-substituted, the moiety is substituted with at least one R substituent and each R substituent is optionally different. For example, where a moiety herein is $R^{14}$-substituted or unsubstituted alkyl, a plurality of $R^{14}$ substituents may be attached to the alkyl moiety wherein each $R^{14}$ substituent is optionally different. Where an R-substituted moiety is substituted with a plurality of R substituents, each of the R-substituents may be differentiated herein using a prime symbol (') such as R', R'', etc. For example, where a moiety is $R^{3A}$-substituted or unsubstituted alkyl, and the moiety is substituted with a plurality of $R^{3A}$ substituents, the plurality of $R^{3A}$ substituents may be differentiated as $R^{3A'}$, $R^{3A''}$, $R^{3A'''}$, etc. In some embodiments, the plurality of R substituents is 3.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula —T—C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula —A—(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R'")$_d$—, where variables s and d are independently integers of from 0 to 3, and X is —O—, —NR'—, —S—, —S(O)—, —S(O)$_2$—, or —S(O)$_2$NR'—. The substituents R, R', R'', and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:
(A) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
(B) alkyl, heteroalkyl, cycloalkyl, heterocycloalkyl, aryl, heteroaryl, substituted with at least one substituent selected from:
   (i) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
   (ii) alkyl, heteroalkyl, cycloalkyl, heterocycloalkyl, aryl, heteroaryl, substituted with at least one substituent selected from:
      (a) oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and
      (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_2$Cl, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "chemical linker," as provided herein, is a covalent linker, a non-covalent linker, a peptide linker (a linker including a peptide moiety), a cleavable peptide linker, a substituted or unsubstituted alkylene, substituted or unsubstituted heteroalkylene, substituted or unsubstituted cycloalkylene, substituted or unsubstituted heterocycloalkylene, substituted or unsubstituted arylene or substituted or unsubstituted heteroarylene or any combination thereof. Thus, a chemical linker as provided herein may include a plurality of chemical moieties, wherein each of the plurality of chemical moieties is chemically different. Alternatively, the chemical linker may be a non-covalent linker. Examples of non-covalent linkers include without limitation, ionic bonds, hydrogen bonds, halogen bonds, van der Waals interactions (e.g. dipole-dipole, dipole-induced dipole, London dispersion), ring stacking (pi effects), and hydrophobic interactions. In embodiments, a chemical linker is formed using conjugate chemistry including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

As used herein, the term "conjugate" refers to the association between atoms or molecules. The association can be direct or indirect. For example, a conjugate between a nucleic acid and a protein can be direct, e.g., by covalent bond, or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, conjugates are formed using conjugate chemistry including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982.

Useful reactive moieties or functional groups used for conjugate chemistries (including "click chemistries" as known in the art) herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with acyl halides, or bonded to metals such as gold;

(h) amine or sulfhydryl groups, which can be, for example, acylated, alkylated or oxidized;

(i) alkenes, which can undergo, for example, cycloadditions, acylation, Michael addition, etc.;

(j) epoxides, which can react with, for example, amines and hydroxyl compounds;

(k) phosphoramidites and other standard functional groups useful in nucleic acid synthesis;

(l) metal silicon oxide bonding;

(m) metal bonding to reactive phosphorus groups (e.g. phosphines) to form, for example, phosphate diester bonds; and (n) sulfones, for example, vinyl sulfone.

Chemical synthesis of compositions by joining small modular units using conjugate ("click") chemistry is well known in the art and described, for example, in H. C. Kolb, M. G. Finn and K. B. Sharpless ((2001). "Click Chemistry: Diverse Chemical Function from a Few Good Reactions". Angewandte Chemie International Edition 40 (11): 2004-2021); R. A. Evans ((2007). "The Rise of Azide—Alkyne 1,3-Dipolar 'Click' Cycloaddition and its Application to Polymer Science and Surface Modification". Australian Journal of Chemistry 60 (6): 384-395; W. C. Guida et al. Med. Res. Rev. p 3 1996; Spiteri, Christian and Moses, John E. ((2010). "Copper-Catalyzed Azide—Alkyne Cycloaddition: Regioselective Synthesis of 1,4,5-Trisubstituted 1,2,3-Triazoles". Angewandte Chemie International Edition 49 (1): 31-33); Hoyle, Charles E. and Bowman, Christopher N. ((2010). "Thiol-Ene Click Chemistry". Angewandte Chemie International Edition 49 (9): 1540-1573); Blackman, Melissa L. and Royzen, Maksim and Fox, Joseph M. ((2008). "Tetrazine Ligation: Fast Bioconjugation Based on Inverse-Electron-Demand Diels—Alder Reactivity". Journal of the American Chemical Society 130 (41): 13518-13519); Devaraj, Neal K. and Weissleder, Ralph and Hilderbrand, Scott A. ((2008). "Tetrazine Based Cycloadditions: Application to Pretargeted Live Cell Labeling". Bioconjugate Chemistry 19 (12): 2297-2299); Stockmann, Henning; Neves, Andre; Stairs, Shaun; Brindle, Kevin; Leeper, Finian ((2011). "Exploring isonitrile-based click chemistry for ligation with biomolecules". Organic & Biomolecular Chemistry), all of which are hereby incorporated by reference in their entirety and for all purposes.

The reactive functional groups can be chosen such that they do not participate in, or interfere with, the chemical stability of the proteins or nucleic acids described herein. By way of example, the nucleic acids can include a vinyl sulfone or other reactive moiety (e.g., maleimide). Optionally, the nucleic acids can include a reactive moiety having the formula —S—S—R. R can be, for example, a protecting group. Optionally, R is hexanol. As used herein, the term hexanol includes compounds with the formula $C_6H_{13}OH$ and includes, 1-hexanol, 2-hexanol, 3-hexanol, 2-methyl-1-pentanol, 3-methyl-1-pentanol, 4-methyl-1-pentanol, 2-methyl-2-pentanol, 3-methyl-2-pentanol, 4-methyl-2-pentanol, 2-methyl-3-pentanol, 3-methyl-3-pentanol, 2,2-dimethyl-1-butanol, 2,3-dimethyl-1-butanol, 3,3-dimethyl-1-butanol, 2,3-dimethyl-2-butanol, 3,3-dimethyl-2-butanol, and 2-ethyl-1-butanol. Optionally, R is 1-hexanol.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

"Nucleic acid" refers to deoxyribonucleotides or ribonucleotides and polymers thereof in either single- or double-stranded form, and complements thereof. The term "polynucleotide" refers to a linear sequence of nucleotides. The term "nucleotide" typically refers to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA (including siRNA), and hybrid molecules having mixtures of single and double stranded DNA and RNA. Nucleic acid as used herein also refers to nucleic acids that have the same basic chemical structure as a naturally occurring nucleic acid. Such analogues have modified sugars and/or modified ring substituents, but retain the same basic chemical structure as the naturally occurring nucleic acid. A nucleic acid mimetic refers to chemical compounds that have a structure that is different from the general chemical structure of a nucleic acid, but that functions in a manner similar to a naturally occurring nucleic acid. Examples of such analogues include, without limitation, phosphorothiolates, phosphoramidates, methyl phosphonates, chiral-methyl phosphonates, 2-O-methyl ribonucleotides, and peptide-nucleic acids (PNAs).

The term "gene" means the segment of DNA involved in producing a protein; it includes regions preceding and following the coding region (leader and trailer) as well as intervening sequences (introns) between individual coding segments (exons). The leader, the trailer, as well as the introns, include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" or "expression vector" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that may be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence. An amino acid residue in a protein "corresponds" to a given residue when it occupies the same essential structural position within the protein as the given residue. One skilled in the art will immediately recognize the identity and location of residues corresponding to a specific position in a protein (e.g., an antibody construct or antigen binding domain provided herein) in other proteins with different numbering systems. For example, by performing a simple sequence alignment with a protein (e.g., an antibody construct or antigen binding domain provided herein) the identity and location of residues corresponding to specific positions of said protein are identified in other protein sequences aligning to said protein. For example, a selected residue in a selected antibody construct (or antigen binding domain) corresponds to light chain threonine at Kabat position 40, when the selected residue occupies the same essential spatial or other structural relationship as a light chain threonine at Kabat position 40. In some embodiments, where a selected protein is aligned for maximum homology with the light chain of an antibody (or antigen binding domain), the position in the aligned selected protein aligning with threonine 40 is said to correspond to threonine 40. Instead of a primary sequence alignment, a three dimensional structural alignment can also be used, e.g., where the structure of the selected protein is aligned for maximum correspondence with the light chain threonine at Kabat position 40, and the overall structures compared. In this case, an amino acid that occupies the same essential position as threonine 40 in the structural model is said to correspond to the threonine 40 residue.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids sequences encode any given amino acid residue. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

The term "peptidyl", "peptidyl moiety" or "peptide moiety" refers to a monovalent peptide and may be alternatively referred to as a portion of a peptide or a portion of a polypeptide.

The term "recombinant" when used with reference, for example, to a cell, a nucleic acid, a protein, or a vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, optionally 65%, 70%, 75%, 80%, 85%, 90%, 95%, 98%, or 99% identity over a specified region, e.g., of the entire polypeptide sequences of the invention or individual domains of the polypeptides of the invention), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. Optionally, the identity exists over a region that is at least about 50 nucleotides in length, or more preferably over a region that is 100 to 500 or 1000 or more nucleotides in length. The present invention includes polypeptides that are substantially identical to any of SEQ ID NOs:1, 2, 3, 4, and 5.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of, e.g., a full length sequence or from 20 to 600, about 50 to about 200, or about 100 to about 150 amino acids or nucleotides in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2:482c, by the homology alignment algorithm of Needleman and Wunsch (1970) *J Mol. Biol.* 48:443, by the search for similarity method of Pearson and Lipman (1988) *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross-reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any appropriate method known in the art for conjugating an antibody to the label may be employed, e.g., using methods described in Hermanson, Bioconjugate Techniques 1996, Academic Press, Inc., San Diego.

Antibodies are large, complex molecules (molecular weight of ~150,000 or about 1320 amino acids) with intricate internal structure. A natural antibody molecule contains two identical pairs of polypeptide chains, each pair having one light chain and one heavy chain. Each light chain and heavy chain in turn consists of two regions: a variable ("V") region involved in binding the target antigen, and a constant ("C") region that interacts with other components of the immune system. The light and heavy chain variable regions come together in 3-dimensional space to form a variable region that binds the antigen (for example, a receptor on the surface of a cell). Within each light or heavy chain variable region, there are three short segments (averaging 10 amino acids in length) called the complementarity determining regions ("CDRs"). The six CDRs in an antibody variable domain (three from the light chain and three from the heavy chain) fold up together in 3-dimensional space to form the actual antibody binding site which docks onto the target antigen. The position and length of the CDRs have been precisely defined by Kabat, E. et al., Sequences of Proteins of Immunological Interest, U.S. Department of Health and Human Services, 1983, 1987. The part of a variable region not contained in the CDRs is called the framework ("FR"), which forms the environment for the CDRs.

An "antibody variant" as provided herein refers to a polypeptide capable of binding to an antigen and including one or more structural domains of an antibody or fragment thereof. Non-limiting examples of antibody variants include single-domain antibodies or nanobodies, affibodies (polypeptides smaller than monoclonal antibodies (e.g., about 6 kDA) and capable of binding antigens with high affinity and imitating monoclonal antibodies, monospecific $Fab_2$, bispecific $Fab_2$, trispecific $Fab_3$, monovalent IgGs, scFv, bispecific diabodies, trispecific triabodies, scFv-Fc, minibodies, IgNAR, V-NAR, hcIgG, VhH, or peptibodies. A "nanobody" or "single domain antibody" as described herein is commonly well known in the art and refers to an antibody fragment consisting of a single monomeric variable antibody domain. Like a whole antibody, it is able to bind selectively to a specific antigen. A "peptibody" as provided herein refers to a peptide moiety attached (through a covalent or non-covalent linker) to the Fc domain of an antibody. Further non-limiting examples of antibody variants known in the art include antibodies produced by cartilaginous fish or camelids. A general description of antibodies from camelids and the variable regions thereof and methods for their production, isolation, and use may be found in references WO97/49805 and WO 97/49805, which are incorporated, by reference herein in their entirety and for all purposes. Likewise, antibodies from cartilaginous fish and the variable regions thereof and methods for their production, isolation, and use may be found in WO2005/118629, which is incorporated by reference herein in its entirety and for all purposes.

The term "antibody" is used according to its commonly known meaning in the art. Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_{H1}$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain (VL) and variable heavy chain (VH) refer to these light and heavy chains respectively. The Fc (i.e. fragment crystallizable region) is the "base" or "tail" of an immunoglobulin and is typically composed of two heavy chains that contribute two or three constant domains depending on the class of the antibody. By binding to specific proteins the Fc region ensures that each antibody generates an appropriate immune response for a given antigen. The Fc region also binds to various cell receptors, such as Fc receptors, and other immune molecules, such as complement proteins.

The term "antigen" as provided herein refers to molecules capable of binding to the antibody binding domain provided herein. An "antigen binding domain" as provided herein is a region of an antibody that binds to an antigen (epitope). As described above, the antigen binding domain may include one constant and one variable domain of each of the heavy and the light chain (VL, VH, CL and CHL respectively). In embodiments, the antigen binding domain includes a light chain variable domain and a heavy chain variable domain. In embodiments, the antigen binding domain includes light chain variable domain and does not include a heavy chain variable domain and/or a heavy chain constant domain. The paratope or antigen-binding site is formed on the N-terminus of the antigen binding domain. The two variable domains of an antigen binding domain may bind the epitope of an antigen.

Antibodies exist, for example, as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH—CH$_1$ by a disulfide bond. The F(ab)'2 may be reduced under mild conditions to break the disulfide linkage in the hinge region, thereby converting the F(ab)'2 dimer into an Fab' monomer. The Fab' monomer is essentially the antigen binding portion with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

A single-chain variable fragment (scFv) is typically a fusion protein of the variable regions of the heavy (VH) and light chains (VL) of immunoglobulins, connected with a short linker peptide of 10 to about 25 amino acids. The linker may usually be rich in glycine for flexibility, as well as serine or threonine for solubility. The linker can either connect the N-terminus of the VH with the C-terminus of the VL, or vice versa.

The epitope of an antibody is the region of its antigen to which the antibody binds. Two antibodies bind to the same or overlapping epitope if each competitively inhibits (blocks) binding of the other to the antigen. That is, a 1×, 5×, 10×, 20× or 100× excess of one antibody inhibits binding of the other by at least 30% but preferably 50%, 75%, 90% or even 99% as measured in a competitive binding assay (see, e.g., Junghans et al., Cancer Res. 50:1495, 1990). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

For preparation of suitable antibodies of the invention and for use according to the invention, e.g., recombinant, monoclonal, or polyclonal antibodies, many techniques known in the art can be used (see, e.g., Kohler & Milstein, Nature 256:495-497 (1975); Kozbor et al., Immunology Today 4: 72 (1983); Cole et al., pp. 77-96 in Monoclonal Antibodies and Cancer Therapy, Alan R. Liss, Inc. (1985); Coligan, Current Protocols in Immunology (1991); Harlow & Lane, Antibodies, A Laboratory Manual (1988); and Goding, Monoclonal Antibodies: Principles and Practice (2d ed. 1986)). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity (see, e.g., Kuby, Immunology (3rd ed. 1997)). Techniques for the production of single chain antibodies or recombinant antibodies (U.S. Pat. Nos. 4,946,778, 4,816,567) can be adapted to produce antibodies to polypeptides of this invention. Also, transgenic mice, or other organisms such as other mammals, may be used to express humanized or human antibodies (see, e.g., U.S. Pat. Nos. 5,545,807; 5,545,806; 5,569,825; 5,625,126; 5,633,425; 5,661,016, Marks et al., Bio/Technology 10:779-783 (1992); Lonberg et al., Nature 368:856-859 (1994); Morrison, Nature 368:812-13 (1994); Fishwild et al., Nature Biotechnology 14:845-51 (1996); Neuberger, Nature Biotechnology 14:826 (1996); and Lonberg & Huszar, Intern. Rev. Immunol. 13:65-93 (1995)). Alternatively, phage display technology can be used to identify antibodies and heteromeric Fab fragments that specifically bind to selected antigens (see, e.g., McCafferty et al., Nature 348:552-554 (1990); Marks et al., Biotechnology 10:779-783 (1992)). Antibodies can also be made bispecific, i.e., able to recognize two different antigens (see, e.g., WO 93/08829, Traunecker et al., EMBO J. 10:3655-3659 (1991); and Suresh et al., Methods in Enzymology 121:210 (1986)). Antibodies can also be heteroconjugates, e.g., two covalently joined antibodies, or immunotoxins (see, e.g., U.S. Pat. No. 4,676, 980, WO 91/00360; WO 92/200373; and EP 03089).

Methods for humanizing or primatizing non-human antibodies are well known in the art (e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534). Humanized antibodies are further described in, e.g., Winter and Milstein (1991) Nature 349:293. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers (see, e.g., Morrison et al., PNAS USA, 81:6851-6855 (1984), Jones et al., Nature 321:522-525 (1986); Riechmann et al., Nature 332:323-327 (1988); Morrison and Oi, Adv. Immunol., 44:65-92 (1988), Verhoeyen et al., Science 239:1534-1536 (1988) and Presta, Curr. Op. Struct. Biol. 2:593-596 (1992), Padlan, Molec. Immun., 28:489-498 (1991); Padlan, Molec. Immun., 31(3):169-217 (1994)), by substituting rodent CDRs or CDR sequences for the corresponding sequences of a human antibody. Accordingly, such humanized antibodies are chimeric antibodies (U.S. Pat. No. 4,816, 567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. For example, polynucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

Techniques for conjugating therapeutic agents to antibodies are well known (see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery" in Controlled Drug Delivery ($2^{nd}$ Ed.), Robinson et al. (eds.), pp. 623-53 (Marcel Dekker, Inc. 1987); Thorpe, "Antibody Carriers Of Cytotoxic Agents In Cancer Therapy: A Review" in Monoclonal Antibodies '84: Biological And Clinical Applications, Pinchera et al. (eds.), pp. 475-506 (1985); and Thorpe et al., "The Preparation And Cytotoxic Properties Of Antibody-Toxin Conjugates", Immunol. Rev., 62:119-58 (1982)).

As used herein, the term "antibody-drug conjugate" or "ADC" refers to a therapeutic agent conjugated or otherwise covalently bound to an antibody.

A "therapeutic agent" or "therapeutic moiety" as used herein refers to an agent (e.g., compound or composition) that when administered to a subject will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms or the intended therapeutic effect, e.g., treatment or amelioration of an injury, disease, pathology or condition, or their symptoms including any objective or subjective parameter of treatment such as abatement; remission; diminishing of symptoms or making the injury, pathology or condition more tolerable to the patient; slowing in the rate of degeneration or decline; making the final point of degeneration less debilitating; or improving a patient's physical or mental well-being. In embodiments, the therapeutic agent is a composition useful in treating or preventing a disease such as cancer.

The phrase "specifically (or selectively) binds to an antibody" or "specifically (or selectively) immunoreactive with," when referring to a protein or peptide refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions typically requires an antibody that is selected for its specificity for a particular protein. For example, polyclonal antibodies can be selected to obtain only a subset of antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Using Antibodies, A Laboratory Manual (1998) for a description of immunoassay formats and conditions that can be used to determine specific immunoreactivity).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated, that the resulting reaction product can be produced directly from a reaction between the added reagents or from an intermediate from one or more of the added reagents which can be produced in the reaction mixture.

The term "contacting" may include allowing two species to react, interact, or physically touch (e.g., bind), wherein the two species may be, for example, an antibody construct as described herein and a cancer protein. In embodiments, contacting includes, for example, allowing an antibody construct to bind to a cancer protein expressed on a cancer cell.

A "cell" as used herein, refers to a cell carrying out metabolic or other functions sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and trans-formed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish. In some embodiments, the sample is obtained from a human.

A "control" sample or value refers to a sample that serves as a reference, usually a known reference, for comparison to a test sample. For example, a test sample can be taken from a test condition, e.g., in the presence of a test compound, and compared to samples from known conditions, e.g., in the absence of the test compound (negative control), or in the presence of a known compound (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

"Patient" or "subject in need thereof" refers to a living organism suffering from or prone to a disease or condition that can be treated by administration of a composition or pharmaceutical composition as provided herein. Non-limiting examples include humans, other mammals, bovines, rats, mice, dogs, monkeys, goat, sheep, cows, deer, and other non-mammalian animals. In some embodiments, a patient is human.

The terms "disease" or "condition" refer to a state of being or health status of a patient or subject capable of being treated with a compound, pharmaceutical composition, or method provided herein. In embodiments, the disease is cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma (Mantle cell lymphoma), head and neck cancer, colorectal cancer, prostate cancer, pancreatic cancer, melanoma, breast cancer, neuroblastoma).

As used herein, the term "cancer" refers to all types of cancer, neoplasm or malignant tumors found in mammals, including leukemias, lymphomas, melanomas, neuroendocrine tumors, carcinomas and sarcomas. Exemplary cancers that may be treated with a compound, pharmaceutical composition, or method provided herein include lymphoma (e.g., Mantle cell lymphoma, follicular lymphoma, diffuse large B-cell lymphoma, marginal zona lymphoma, Burkitt's lymphoma), sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia (e.g., lymphoblastic leukemia, chronic lymphocytic leukemia, hairy cell leukemia), acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). The P388 leukemia model is widely accepted as being predictive of in vivo anti-leukemic activity. It is believed that a compound that tests positive in the P388 assay will generally exhibit some level of anti-leukemic activity in vivo regardless of the type of leukemia being treated. Accordingly, the present application includes a method of treating leukemia, and, preferably, a method of treating acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The term "associated" or "associated with" in the context of a substance or substance activity or function associated with a disease (e.g., cancer (e.g. leukemia, lymphoma, B cell lymphoma, or multiple myeloma)) means that the disease (e.g. cancer, (e.g. leukemia, lymphoma, B cell lymphoma, or multiple myeloma)) is caused by (in whole or in part), or a symptom of the disease is caused by (in whole or in part) the substance or substance activity or function.

As used herein, "treatment" or "treating," or "palliating" or "ameliorating" are used interchangeably herein. These terms refer to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made. Treatment includes preventing the disease, that is, causing the clinical symptoms of the disease not to develop by administration of a protective composition prior to the induction of the disease; suppressing the disease, that is, causing the clinical symptoms of the disease not to develop by administration of a protective composition after the inductive event but prior to the clinical appearance or reappearance of the disease; inhibiting the disease, that is, arresting the development of clinical symptoms by administration of a protective composition after their initial appearance; preventing re-occurring of the disease and/or relieving the disease, that is, causing the regression of clinical symptoms by administration of a protective composition after their initial appearance. For example, certain methods herein treat cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma). For example certain methods herein treat cancer by decreasing or reducing or preventing the occurrence, growth, metastasis, or progression of cancer; or treat cancer by decreasing a symptom of cancer. Symptoms of cancer (e.g. lung cancer, ovarian cancer, osteosarcoma, bladder cancer, cervical cancer, liver cancer, kidney cancer, skin cancer (e.g., Merkel cell carcinoma), testicular cancer, leukemia, lymphoma, head and neck cancer, colorectal cancer, prostate cancer, pancreatic cancer, melanoma, breast cancer, neuroblastoma) would be known or may be determined by a person of ordinary skill in the art.

As used herein the terms "treatment," "treat," or "treating" refers to a method of reducing the effects of one or more symptoms of a disease or condition characterized by expression of the protease or symptom of the disease or condition characterized by expression of the protease. Thus in the disclosed method, treatment can refer to a 10%, 20%, 30%, 40%, 50%, 60%, 70%, 80%, 90%, or 100% reduction in the severity of an established disease, condition, or symptom of the disease or condition. For example, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. Further, as used herein, references to decreasing, reducing, or inhibiting include a change of 10%, 20%, 30%, 40%, 50%, 60%, 70%, 80%, 90% or greater as compared to a control level and such terms can include but do not necessarily include complete elimination.

An "effective amount" is an amount sufficient to accomplish a stated purpose (e.g. achieve the effect for which it is administered, treat a disease, reduce enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme or protein relative to the absence of the antagonist. A "function disrupting amount," as used herein, refers to the amount of antagonist required to disrupt the function of an enzyme or protein relative to the absence of the antagonist. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example cancer therapies such as chemotherapy, hormonal therapy, radiotherapy, or immunotherapy. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered by transdermally, by a topical route, formulated as applicator sticks, solutions, suspensions, emulsions, gels, creams, ointments, pastes, jellies, paints, powders, and aerosols.

Formulations suitable for oral administration can consist of (a) liquid solutions, such as an effective amount of the antibodies provided herein suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Pharmaceutical compositions can also include large, slowly metabolized macromolecules such as proteins, polysaccharides such as chitosan, polylactic acids, polyglycolic acids and copolymers (such as latex functionalized sepharose(™), agarose, cellulose, and the like), polymeric amino acids, amino acid copolymers, and lipid aggregates (such as oil droplets or liposomes). Additionally, these carriers can function as immunostimulating agents (i.e., adjuvants).

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the compound of choice with a base, including, for example, liquid triglycerides, polyethylene glycols, and paraffin hydrocarbons.

Formulations suitable for parenteral administration, such as, for example, by intraarticular (in the joints), intravenous, intramuscular, intratumoral, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration, oral administration, and intravenous administration are the preferred methods of administration. The formulations of compounds can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The combined administration contemplates co-administration, using separate formulations or a single pharmaceutical formulation, and consecutive administration in either order, wherein preferably there is a time period while both (or all) active agents simultaneously exert their biological activities.

Effective doses of the compositions provided herein vary depending upon many different factors, including means of administration, target site, physiological state of the patient, whether the patient is human or an animal, other medications administered, and whether treatment is prophylactic or therapeutic. However, a person of ordinary skill in the art would immediately recognize appropriate and/or equivalent doses looking at dosages of approved compositions for treating and preventing cancer for guidance.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances, and the like, that do not deleteriously react with the compounds of the invention. One of skill in the art will recognize that other pharmaceutical excipients are useful in the present invention.

The term "pharmaceutically acceptable salt" refers to salts derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

The pharmaceutical preparation is optionally in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The unit dosage form can be of a frozen dispersion.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In embodiments, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Antibody Constructs

Provided herein are, inter alia, compositions useful for the treatment of cancer. The antibody variable domain and antibody constructs including the same provided herein are, inter alia, useful for targeting and killing cancer cells while leaving healthy cells unharmed. The compositions provided herein, including embodiments thereof, are capable of specifically binding to human mantle cell lymphomas (MCLs) and causing targeted lysis of MCL cells in the presence of effector cells (e.g., NK cells). Surprisingly, the antibody variable domain and antibody constructs provided herein do not bind to non-cancer (healthy) cells, thereby preventing adverse effects otherwise caused by unspecific killing of healthy cells. Due to their ability to differentially bind cancer cells versus non-cancer cells, the antibody variable domain and antibody constructs provided herein are highly efficient and efficacious agents useful for therapeutic and diagnostic purposes.

In an aspect is provided an antibody variable domain including a CDR 1 as set forth in SEQ ID NO:1, a CDR 2 as set forth in SEQ ID NO:2 and a CDR 3 as set forth in SEQ ID NO:3. The order the CDRs are listed corresponds to their order in the antibody variable domain from the N-terminus to the C-terminus. Thus, in N-terminus to C-terminus direction the antibody variable domain may include a CDR 1 as set forth in SEQ ID NO:1, a CDR 2 as set forth in SEQ ID NO:2 and a CDR 3 as set forth in SEQ ID NO:3. In embodiments, the antibody variable domain includes the sequence of SEQ ID NO:5. In embodiments, the antibody variable domain is the sequence of SEQ ID NO:5.

An "antibody variable domain" as provided herein refers to a peptide (e.g., peptide domain) or peptidyl moiety capable of binding an antigen. An antibody variable domain as provided includes CDR sequences and framework region (FR) sequences of a light chain variable (VL) domain or a heavy chain variable (VH) domain. An antibody variable domain as provided may include a light chain variable (VL) domain or a heavy chain variable (VH) domain. Thus, in embodiments, the antibody variable domain includes a light chain variable (VL) domain. In embodiments, the antibody variable domain includes a heavy chain variable (VH) domain. In embodiments, the antibody variable domain is a light chain variable (VL) domain. In embodiments, the antibody variable domain is a heavy chain variable (VH) domain.

A "heavy chain variable (VH) domain" as provided herein is an antibody variable domain of a heavy chain of an antibody or a fragment thereof. Likewise, the "light chain variable (VL) domain" as provided herein is an antibody variable domain of a light chain of an antibody or a fragment thereof. In embodiments, the light chain variable (VL) domain includes CDR 1, CDR 2, CDR 3 and FR 1, FR 2, FR 3 and FR4 (framework regions) of an antibody variable light chain. Thus, the antibody variable domain may be the variable domain of the light chain of an antibody. In embodiments, the antibody variable domain is the variable domain of the light chain of an antibody. In embodiments, the antibody variable domain is the variable domain of the light chain of an antibody fragment. In embodiments, the antibody variable domain is the variable domain of the light chain of an antibody variant. In embodiments, the antibody variable domain is the variable domain of the light chain of a Fab. The antibody variable domain may be the variable domain of the heavy chain of an antibody. In embodiments, the antibody variable domain is the variable domain of the heavy chain of an antibody fragment. In embodiments, the antibody variable domain is the variable domain of the heavy chain of an antibody variant. In embodiments, the antibody variable domain is the variable domain of the heavy chain of a Fab. In view of the foregoing, the antibody variable domain provided herein may include or be the variable domain of the light chain of an antibody, fragment or variant thereof or the variable domain of the heavy chain of an antibody, fragment or variant thereof. Thus, in embodiments, the antibody variable domain is an antibody light chain variable domain. In embodiments, the antibody variable domain is an antibody heavy chain variable domain.

Figure 2A:
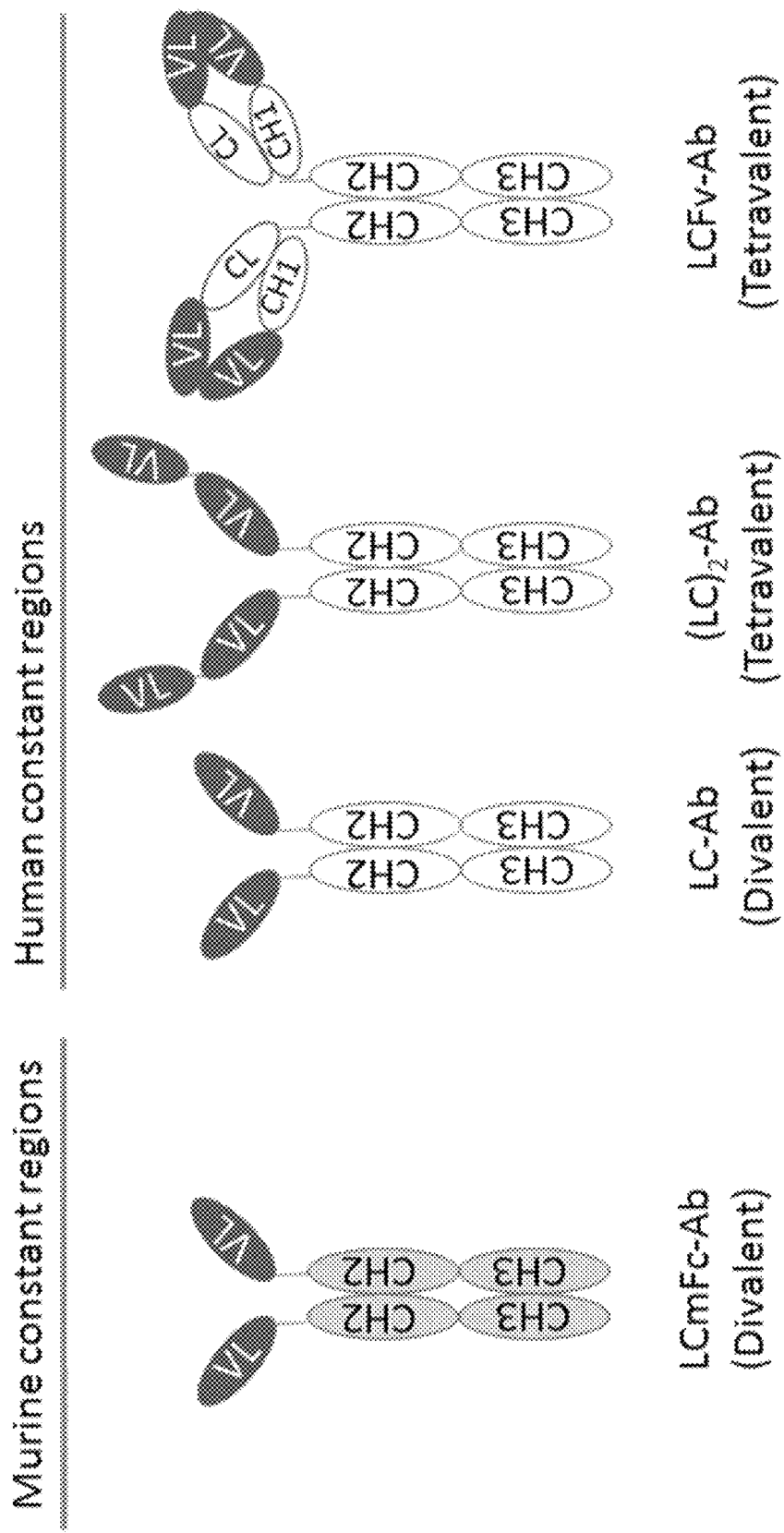
FIGS. 2A-2B. Antibody variants (antibody constructs) produced and tested.
Figure 2A:
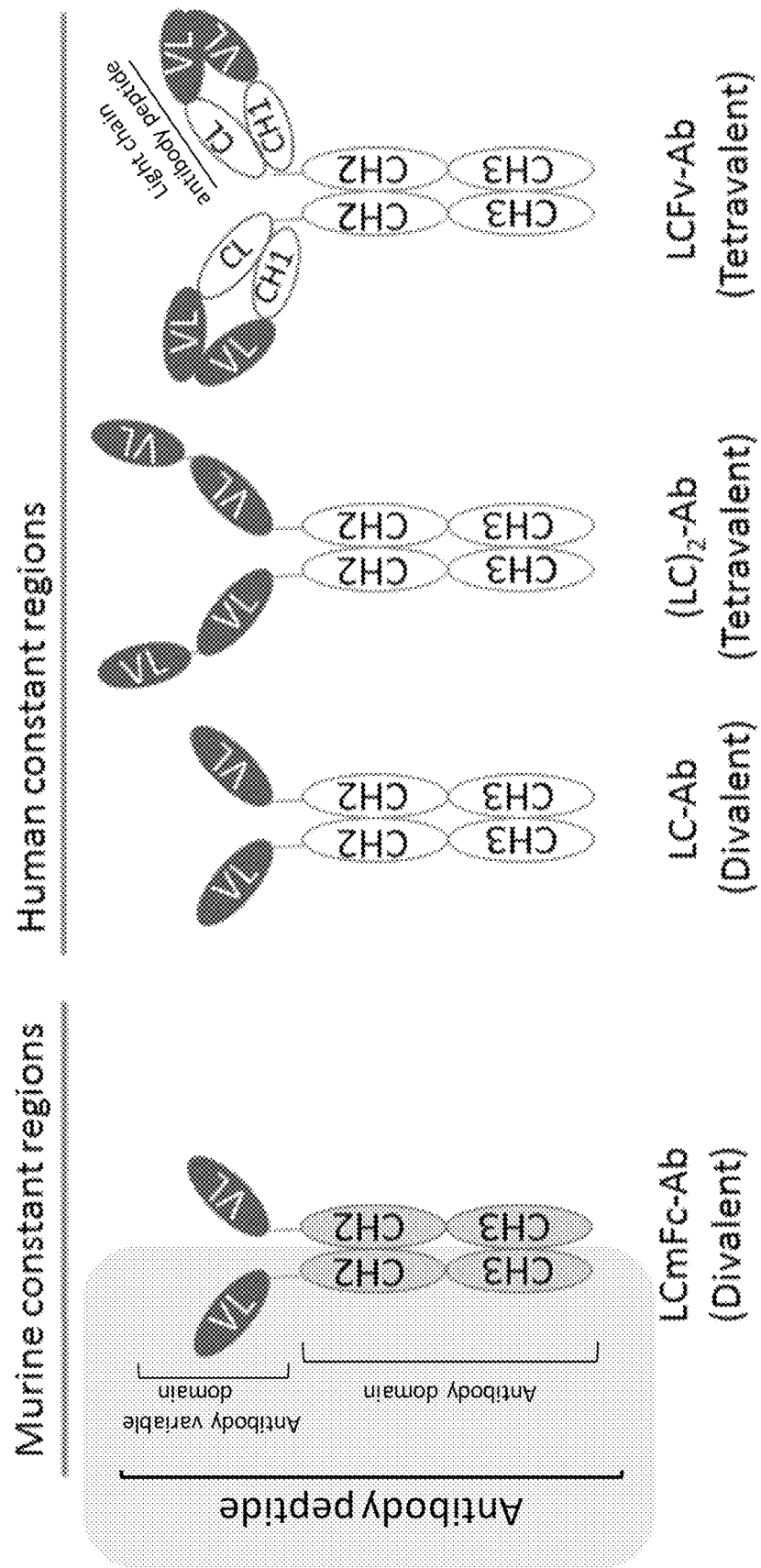
Figure 2B:
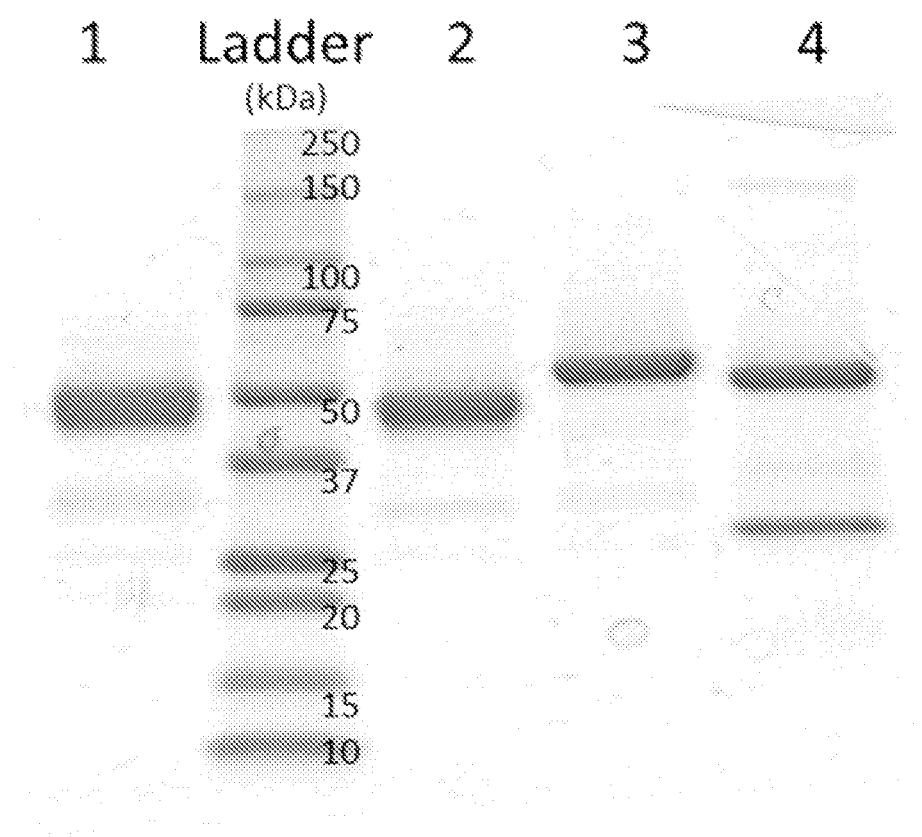
Figure 3A:
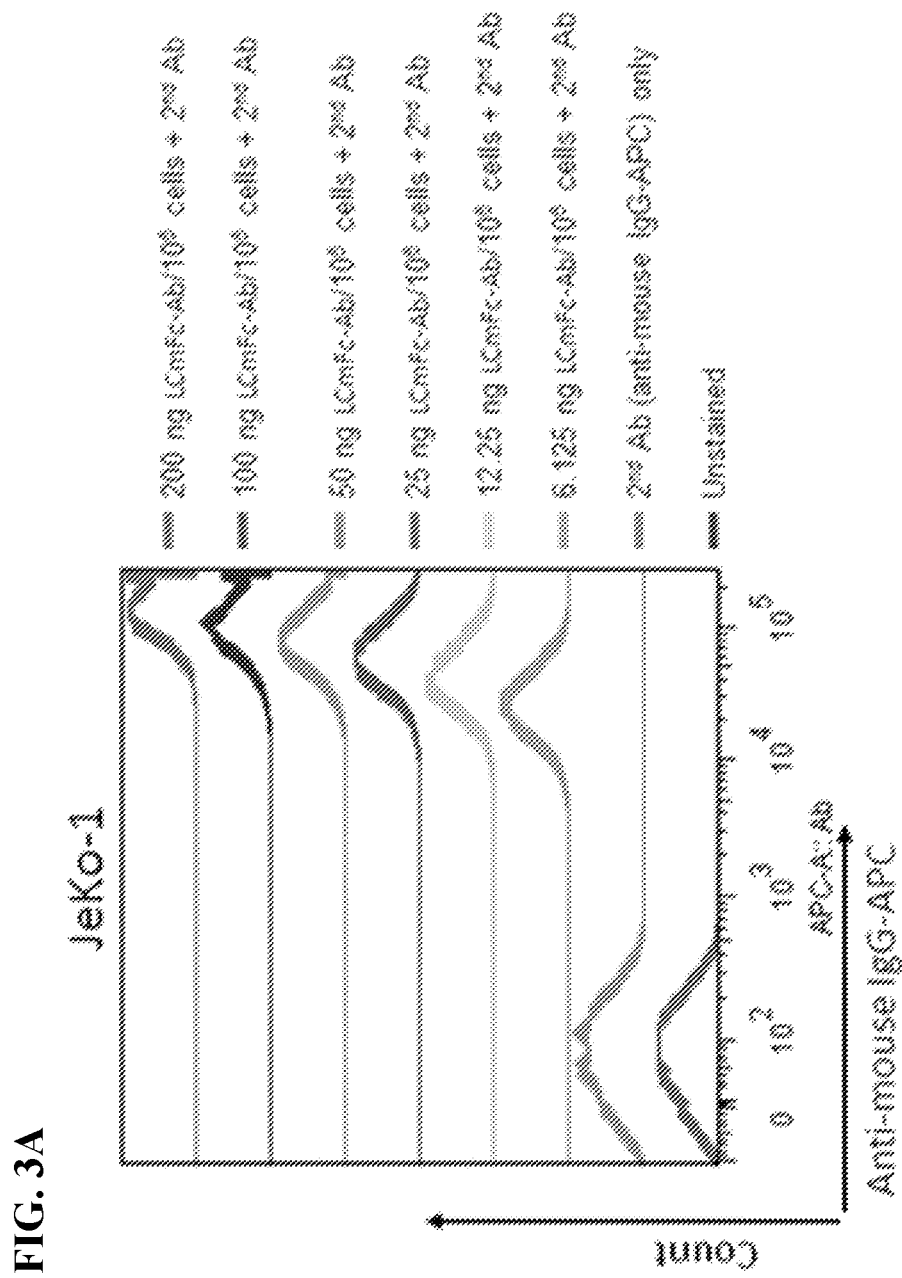
FIGS. 3A-3C. Characterization of MCL-specific binding by 4-4 human antibody constructs. FACS histograms display the binding of 4-4 LCmFc-Ab on various cells and at various concentrations, which was detected by APC conjugated anti-mouse IgG secondary antibodies. Unstained cells and secondary antibody alone were used as negative controls.
Figure 3B:
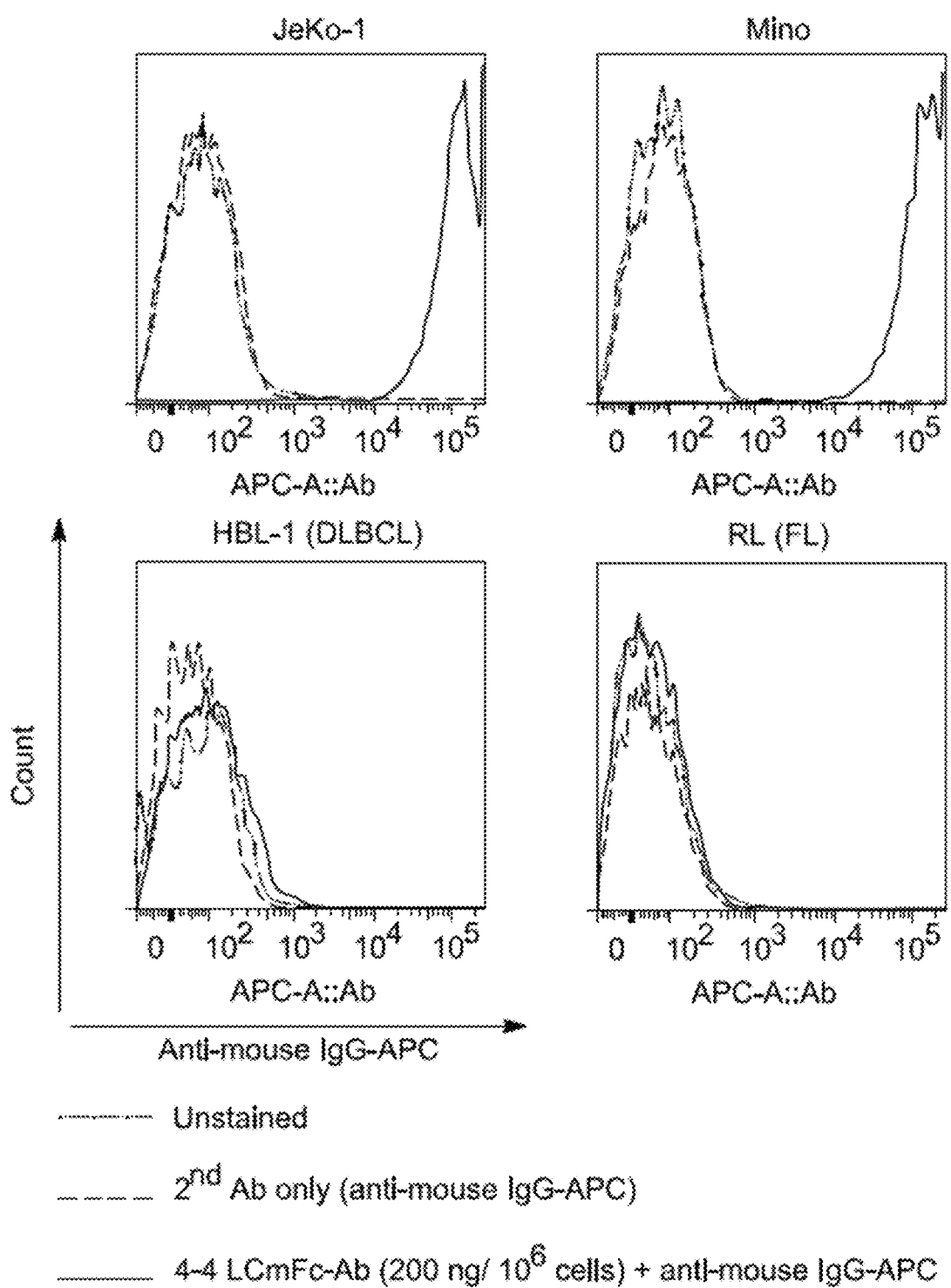
Figure 3B:
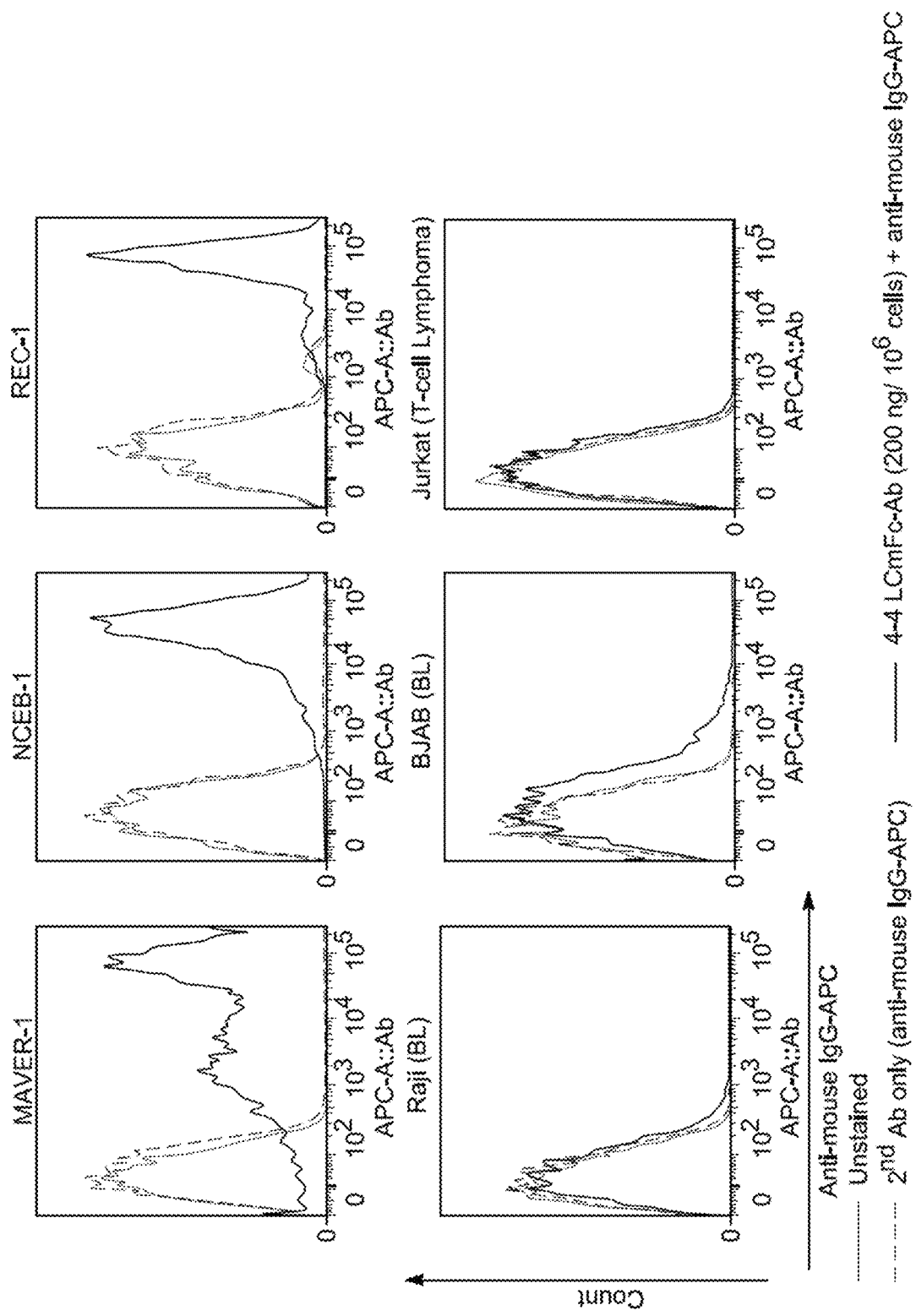
Figure 3C:
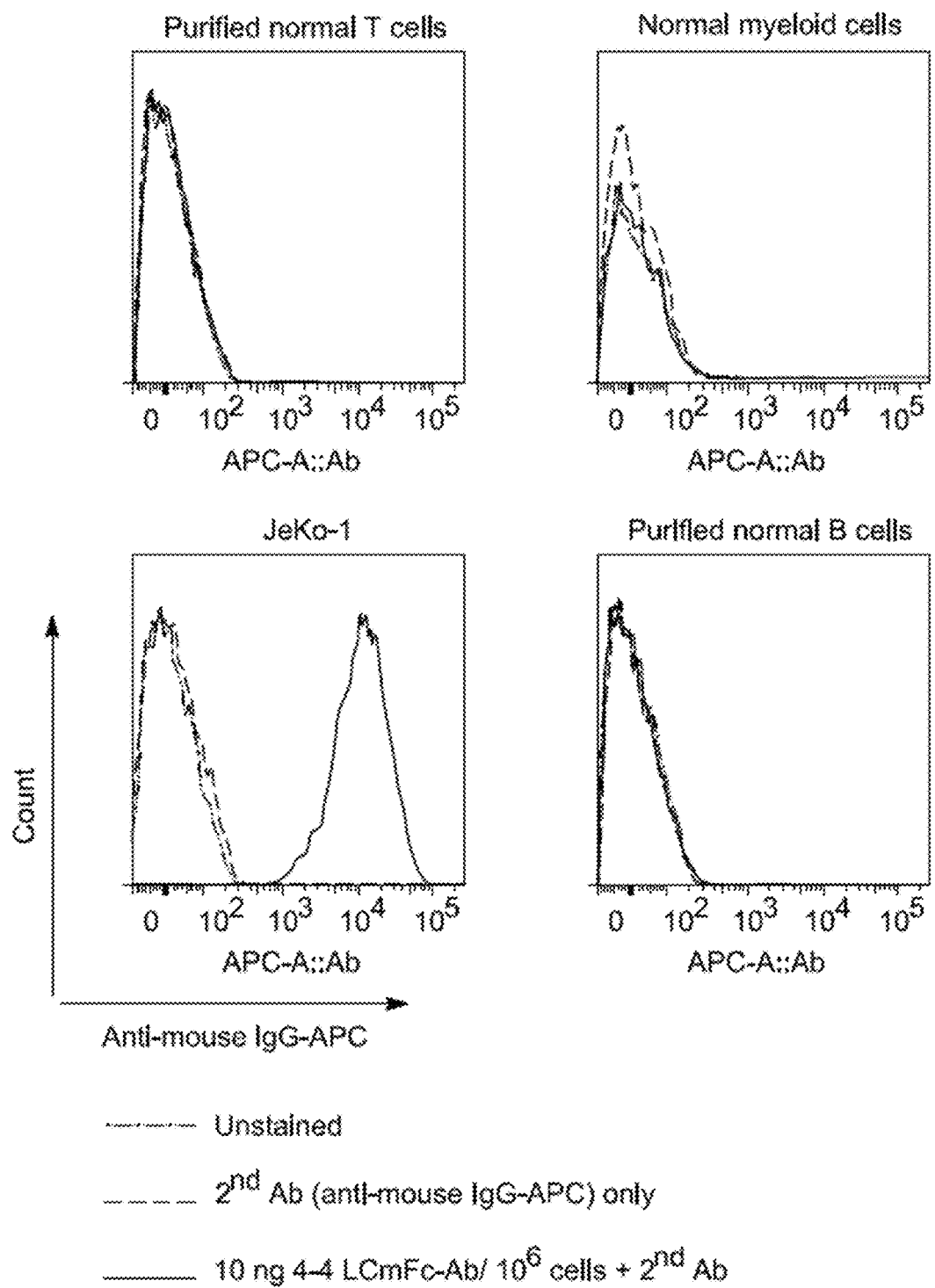
Figures 4A, 4B:
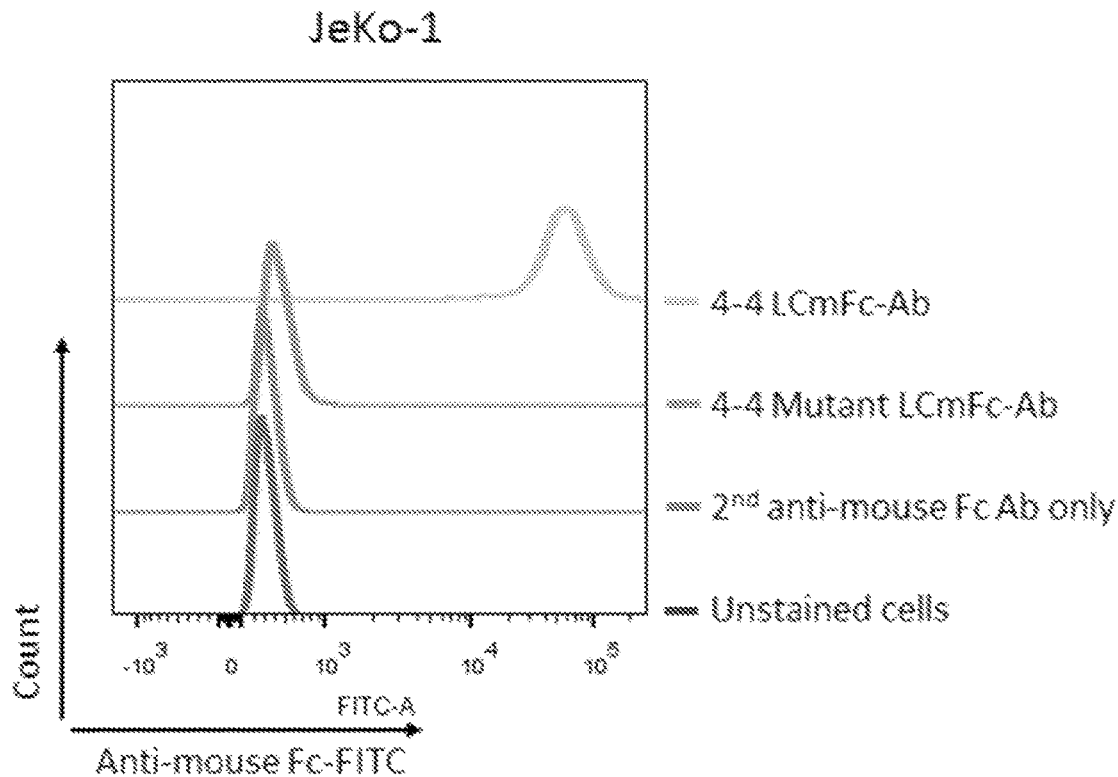
FIG. 4A: 4-4 VL amino acid sequences of complementarity determining region (CDR) 3. Parental 4-4 VL (above) underwent two point mutation to Kabat numbered light chain amino acid residue 91 and 92 on CDR3 (W91A and D92S) to become 4-4 VL Mutant (below).
FIG. 4B: FACS histogram displaying 4-4 LCmFc-Ab binding compared with 4-4 Mutant LCmFc-Ab on JeKo-1 cells. 0.1 of antibodies/10⁶ cells were used and binding was detected by FITC conjugated anti-mouse Fc secondary antibodies. Unstained cells and secondary antibody alone were used as negative controls.
Figure 5:
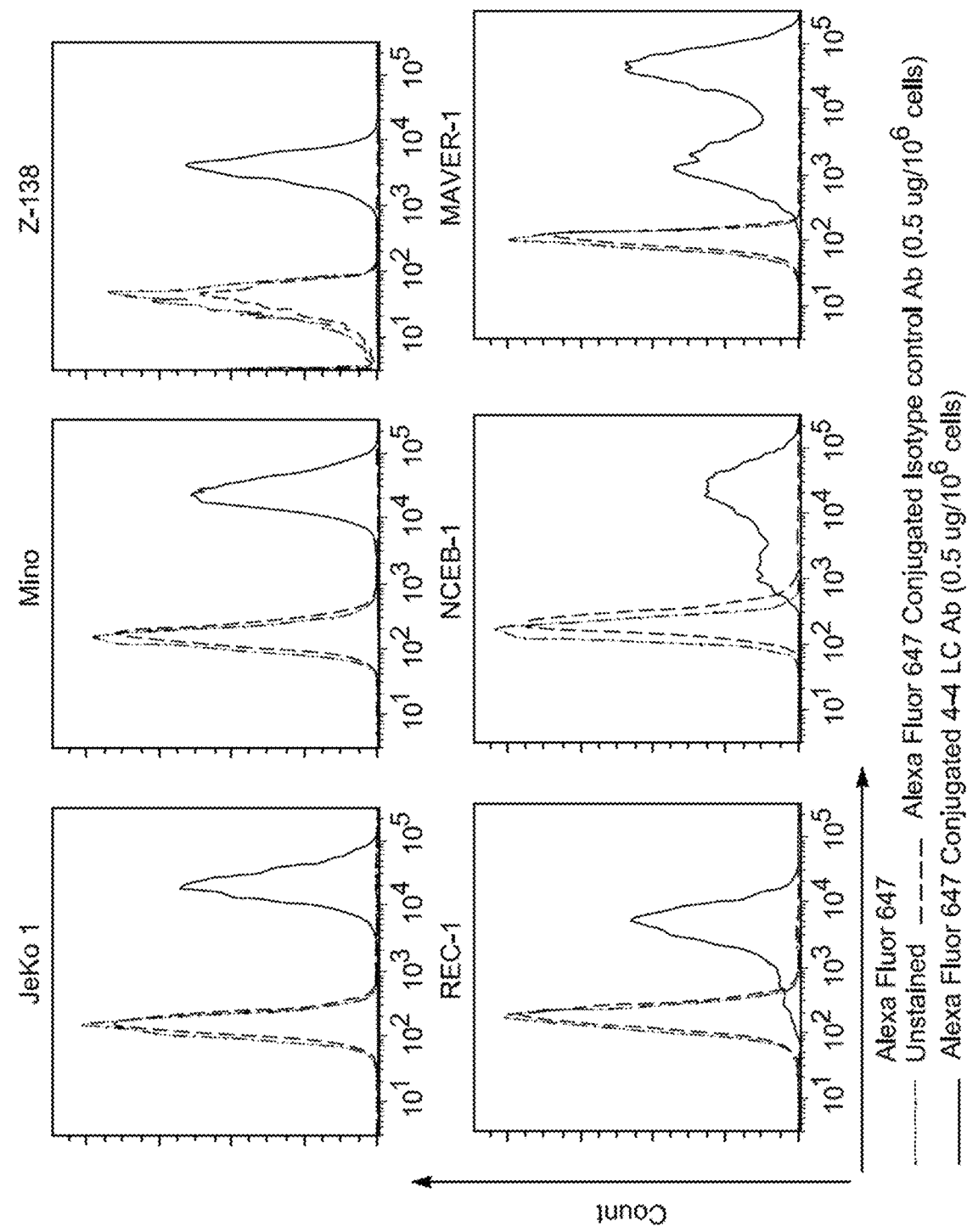
FIG. 5. 4-4 LC-Ab construct specifically binding MCLs. FACS histogram displaying the binding of Alexa Fluor 647 conjugated 4-4 LC-Ab on MCLs and non-MCL B-cell NHLs and leukemias. Non-MCL lines include: RL, follicular lymphoma; Raji and Ramos, Burkitt lymphoma; SU-DHL-6 and CLI-LY3, diffuse large B-cell lymphoma; MECl, chronic lymphocytic leukemia; RS4;11, acute lymphoblastic leukemia. Unstained cells were and Alexa Fluor 647 conjugated isotype antibodies were used as controls.
Figure 5:
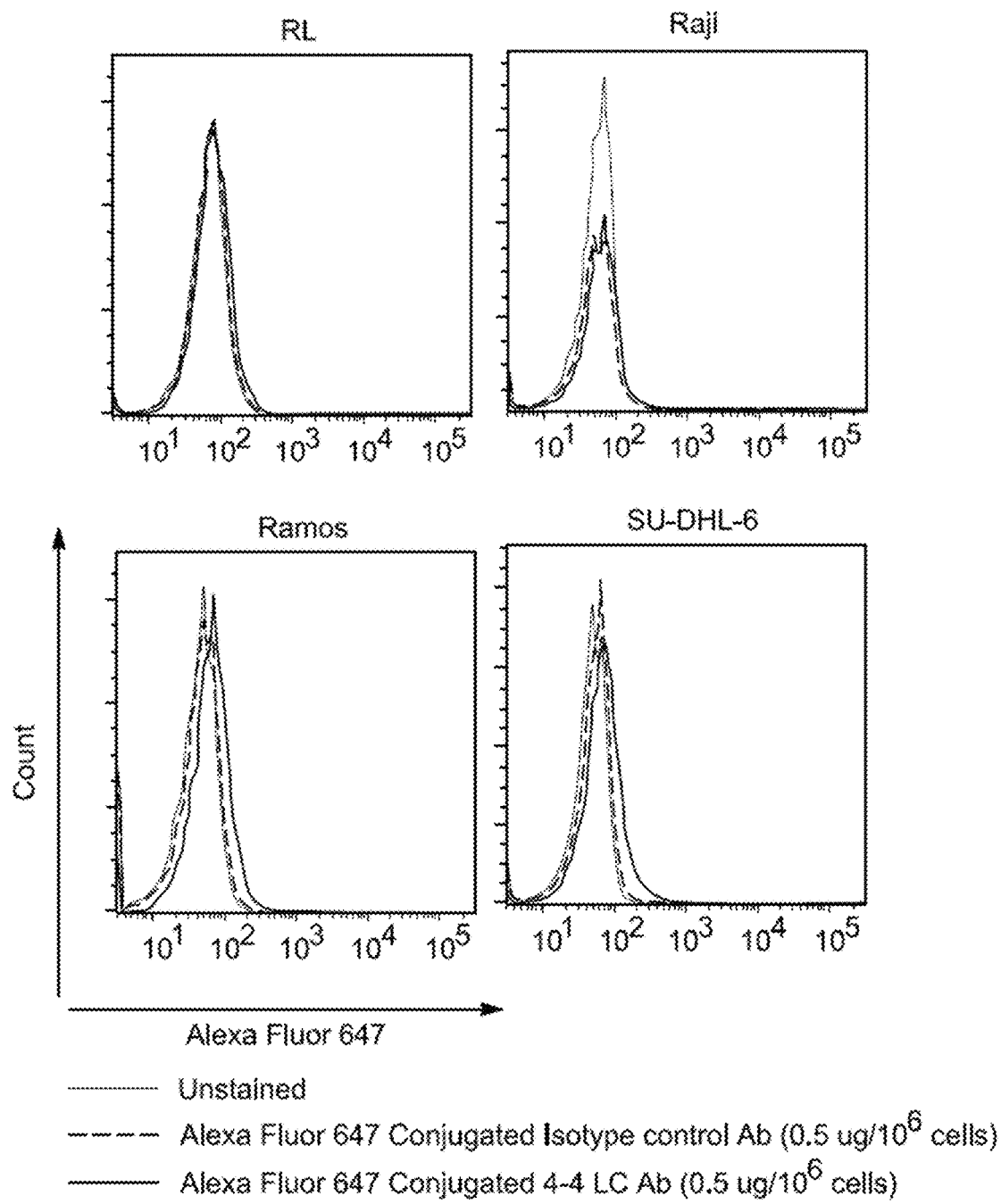
Figure 5:
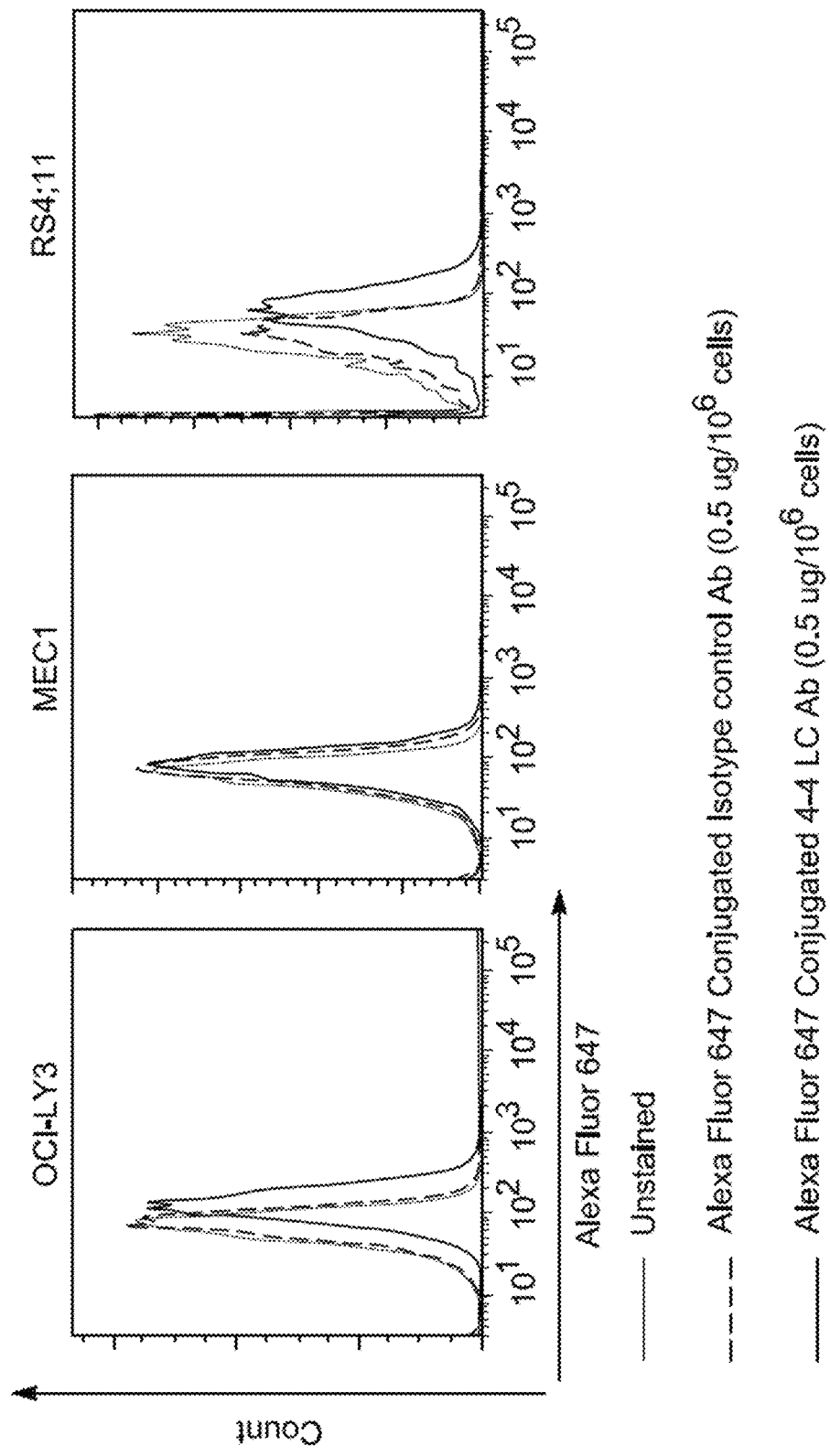
Figure 6A:
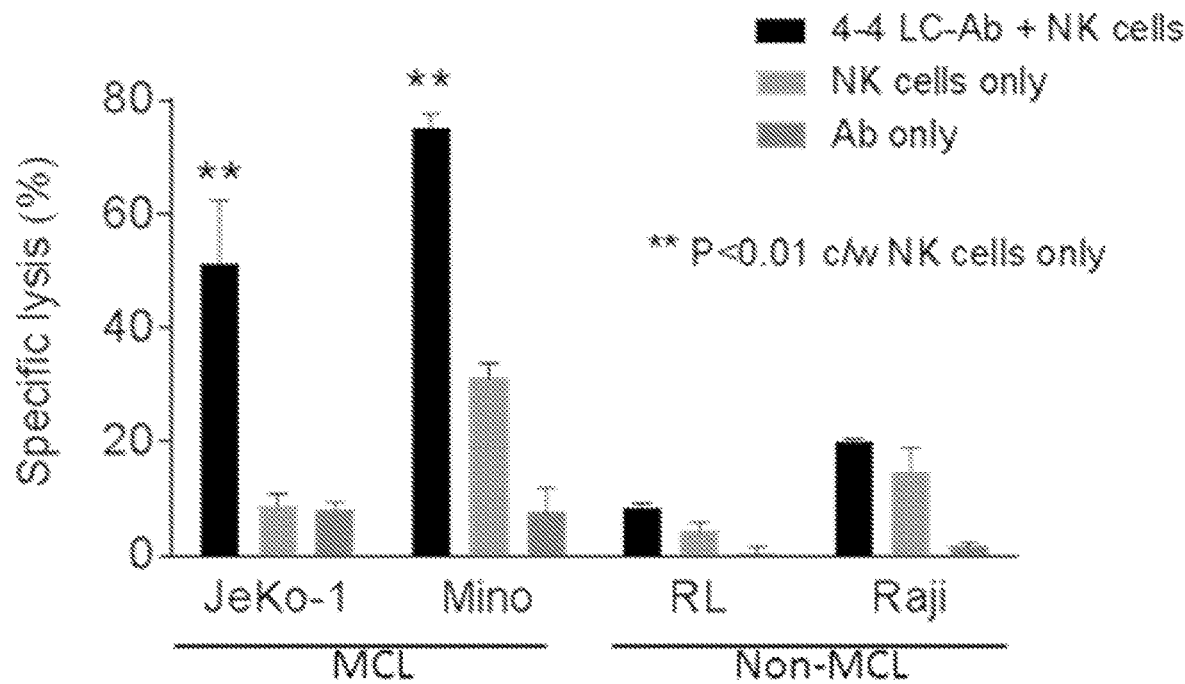
FIGS. 6A-6C. 4-4 LC-Ab construct demonstrated cytotoxicity specifically against MCL. Results of chromium-51 (⁵¹Cr) release assays. Specific lysis measured target (T) cell lysis by effector (E) NK cells at E:T ratio 20:1 with or without the addition of 4-4 LC-Ab. Percentage reflects complete cell lysis by detergent and corrected for spontaneous ⁵¹Cr released. Controls included NK cells only and 4-4 LC-Ab only. Specific lysis of (FIG. 6A) mantle cell lymphoma (MCL) lines JeKo-1 and Mino compared with non-MCL lines RL and Raji.
Figure 6B:
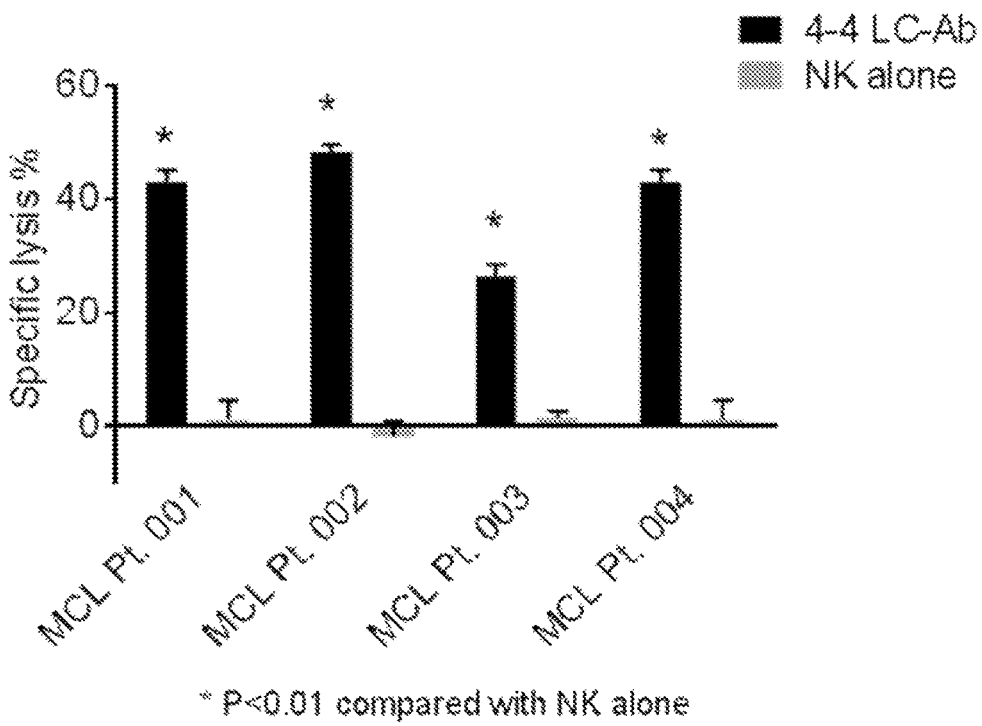
Figure 6C:
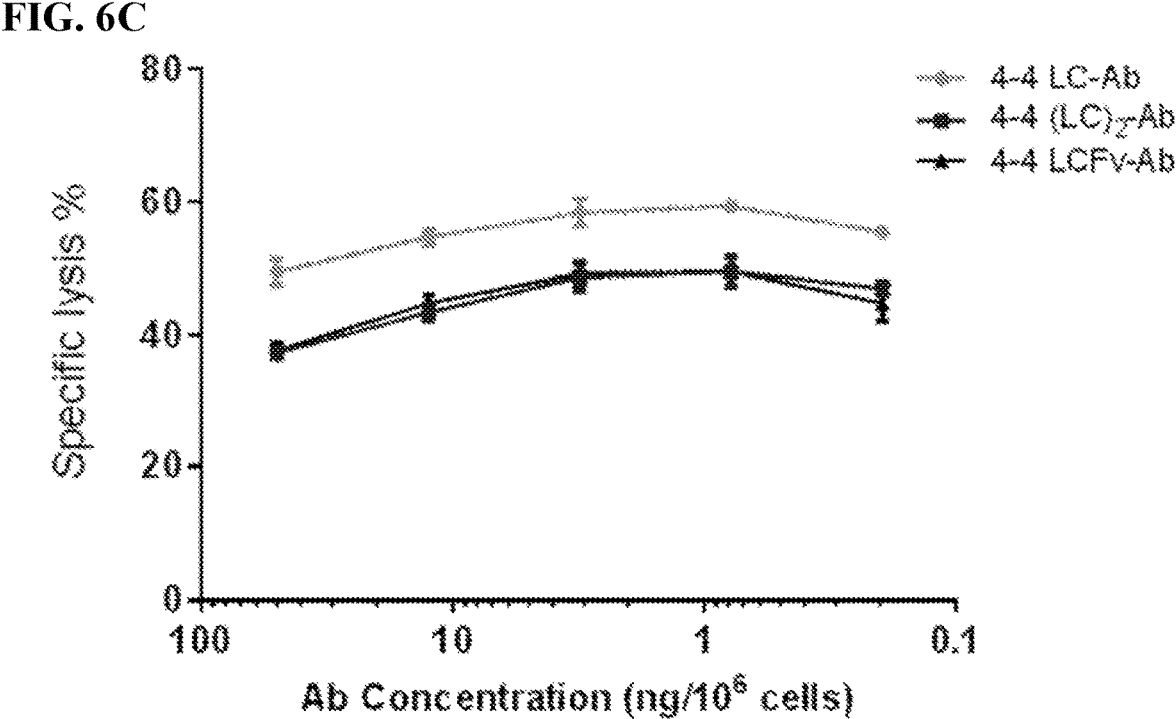
Figure 7A:
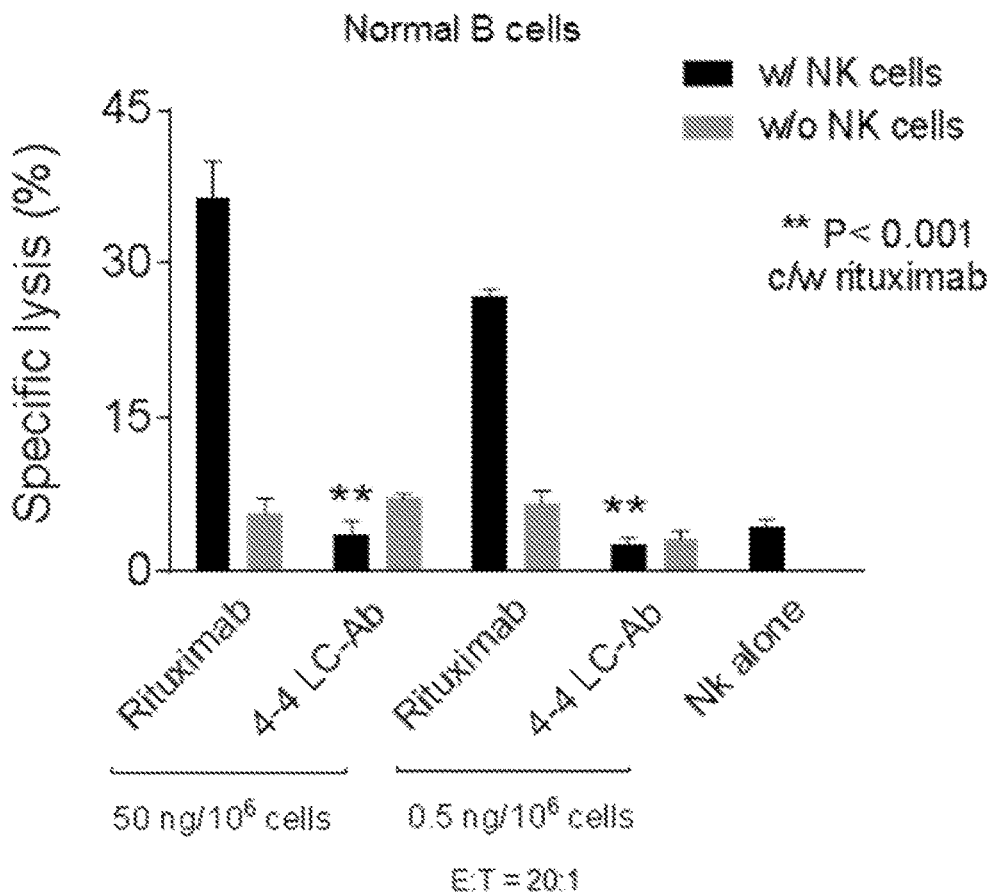
FIGS. 7A-7B. 4-4 LC-Ab construct demonstrated no in vitro cytotoxicity against normal human B cells.
Figure 7B:
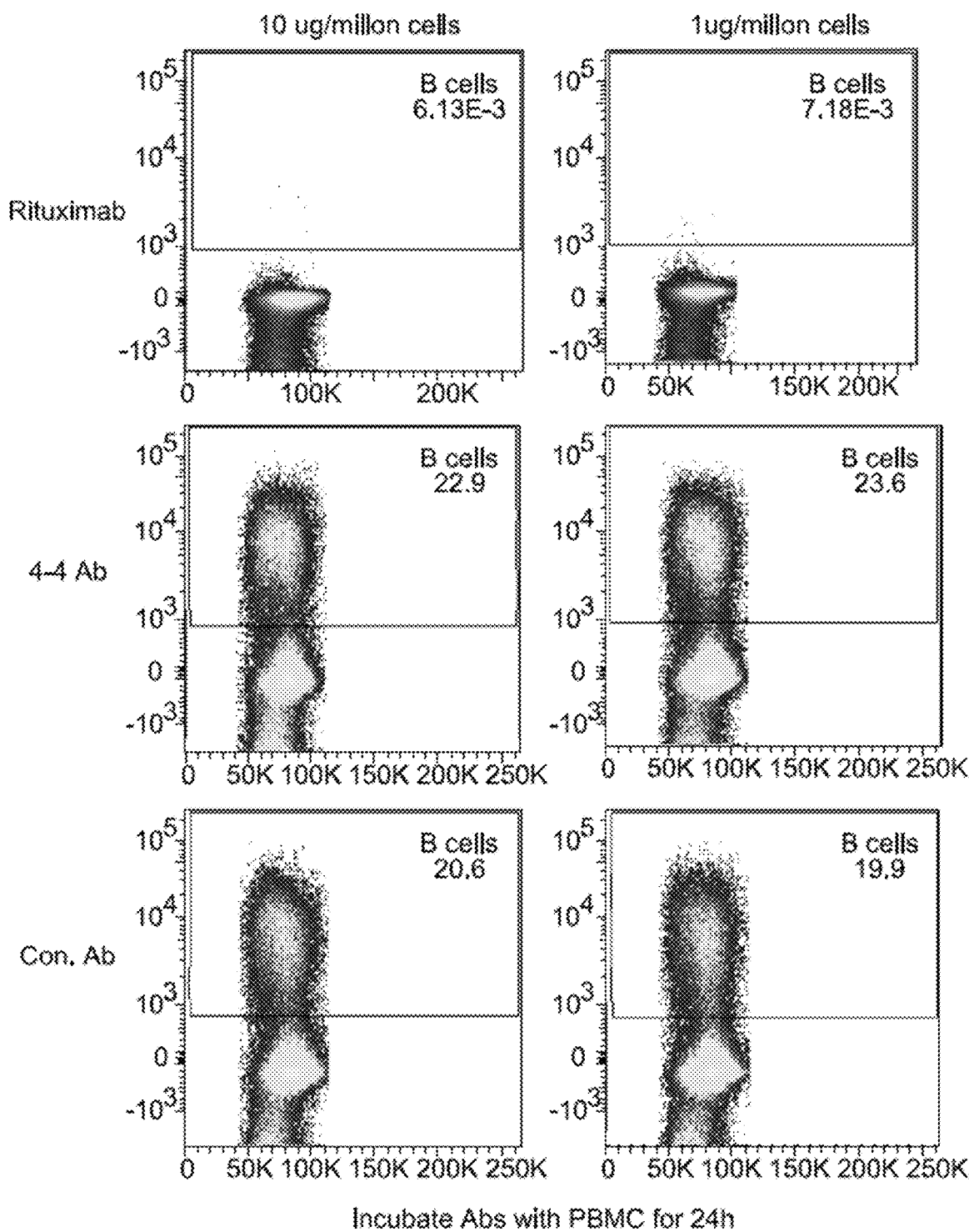
Figure 7B:
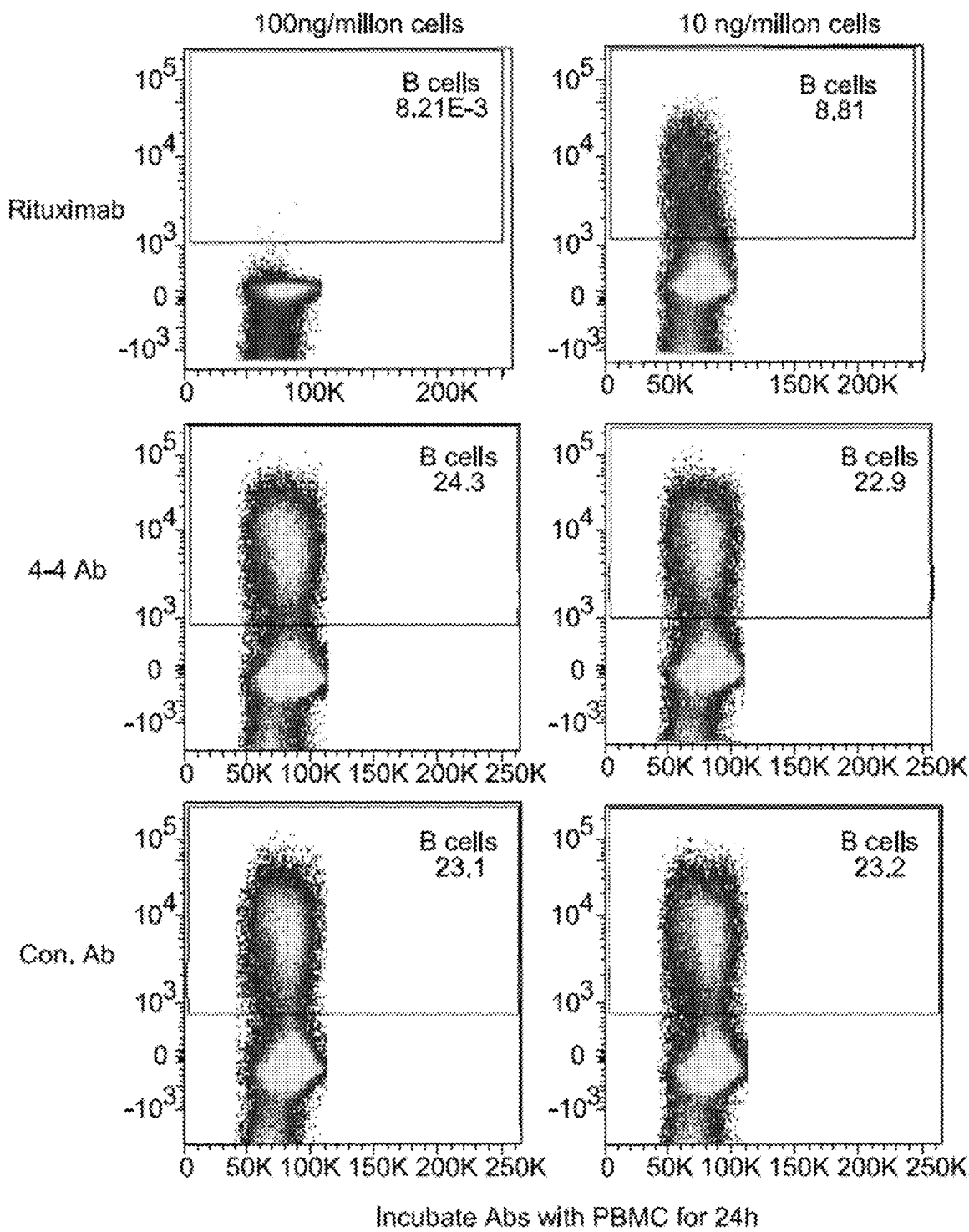
Figure 7B:
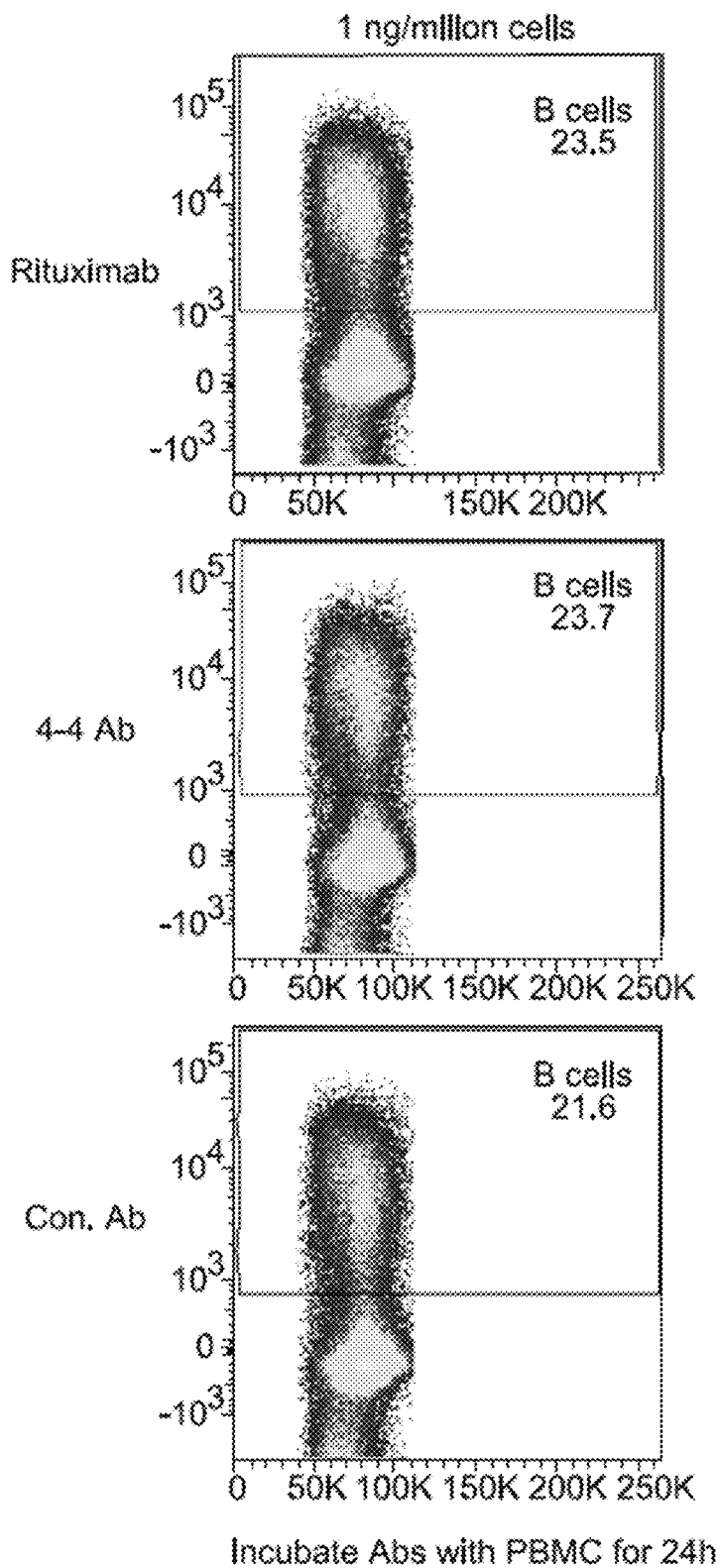
Figure 8A:
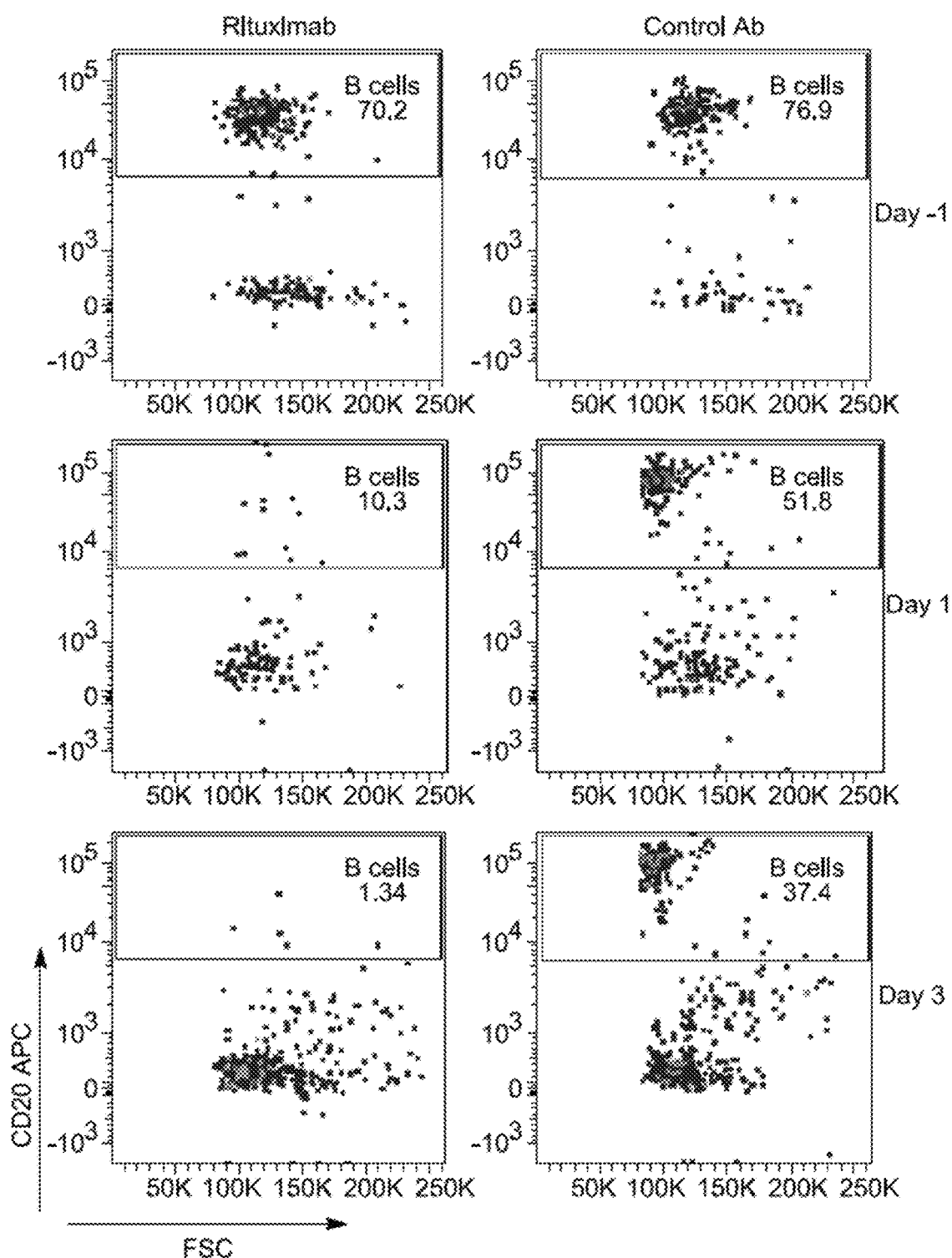
FIGS. 8A-8B. 4-4 LC-Ab construct did not cause B-cell depletion in humanized mice.
Figure 8A:
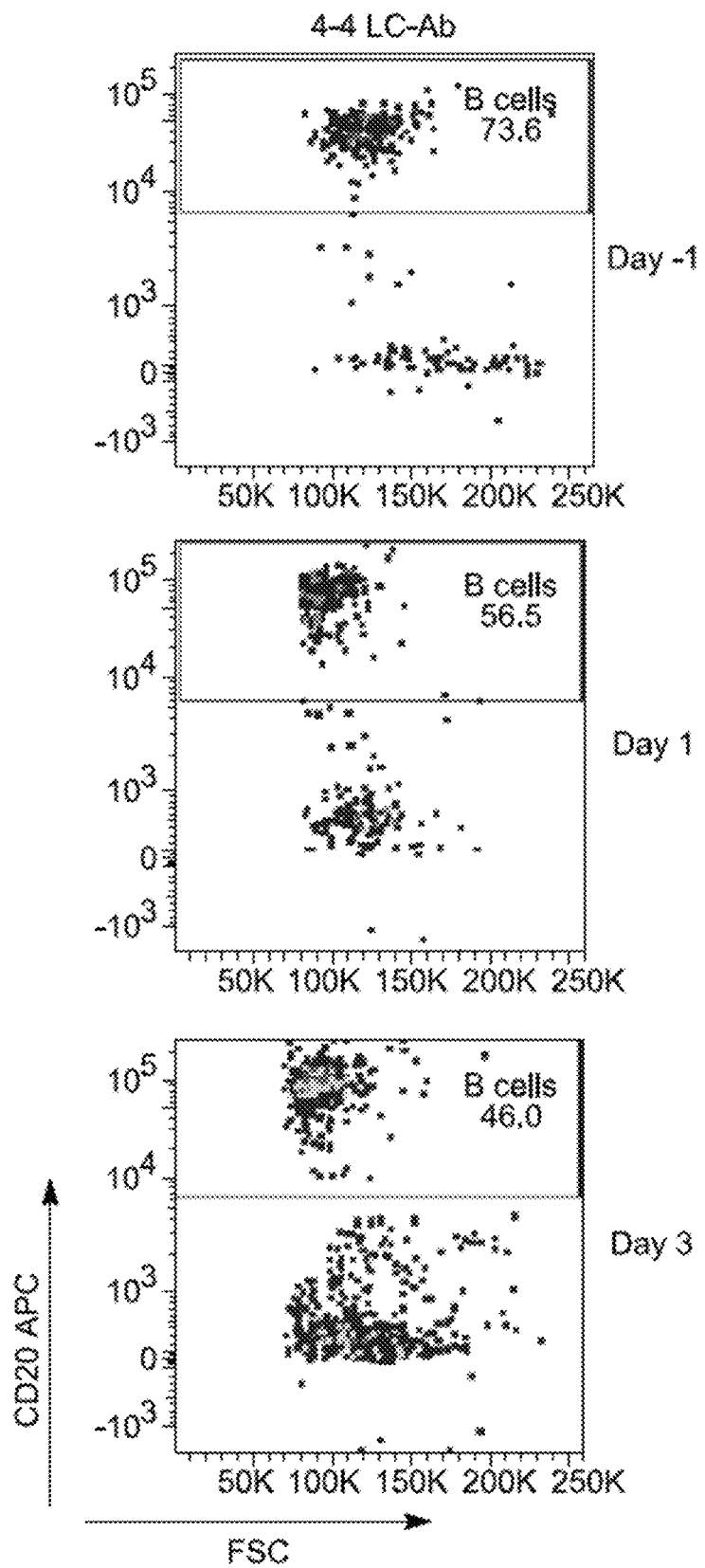
Figure 8B:
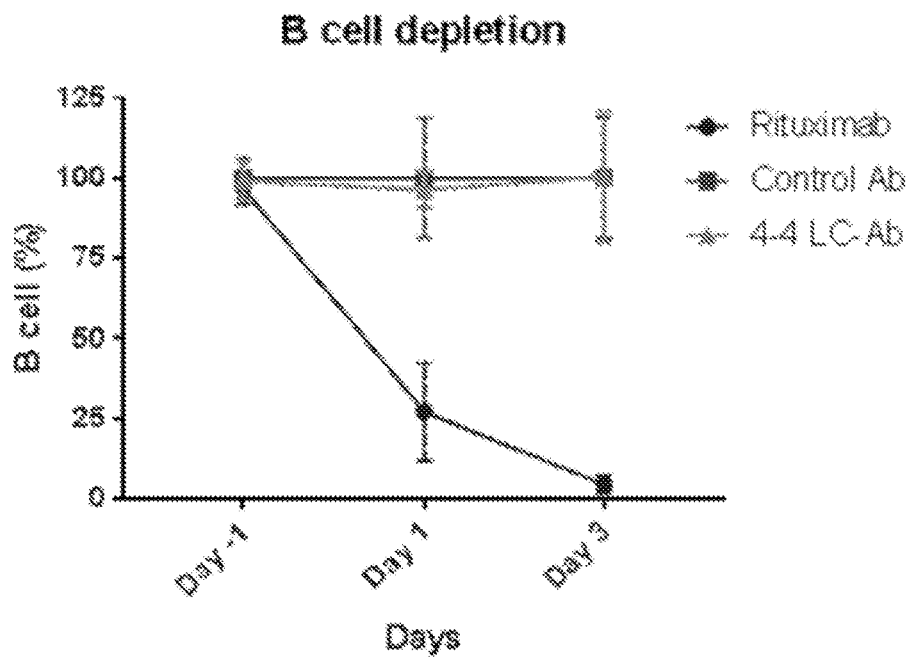
Figure 9A:
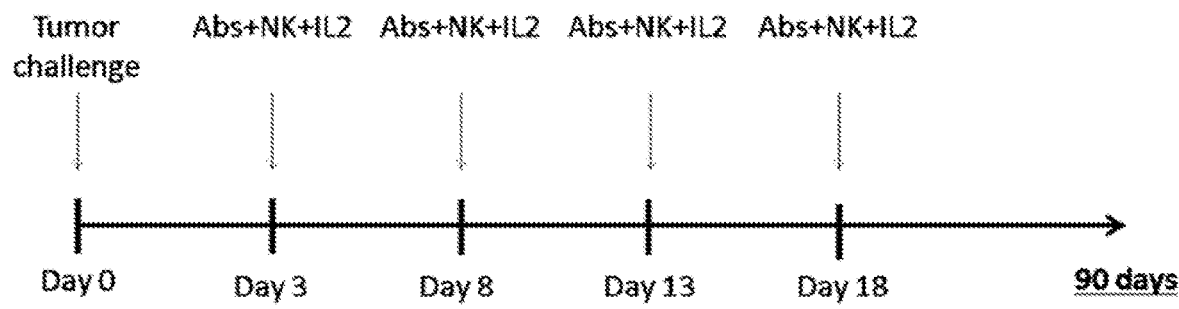
Figure 9C:
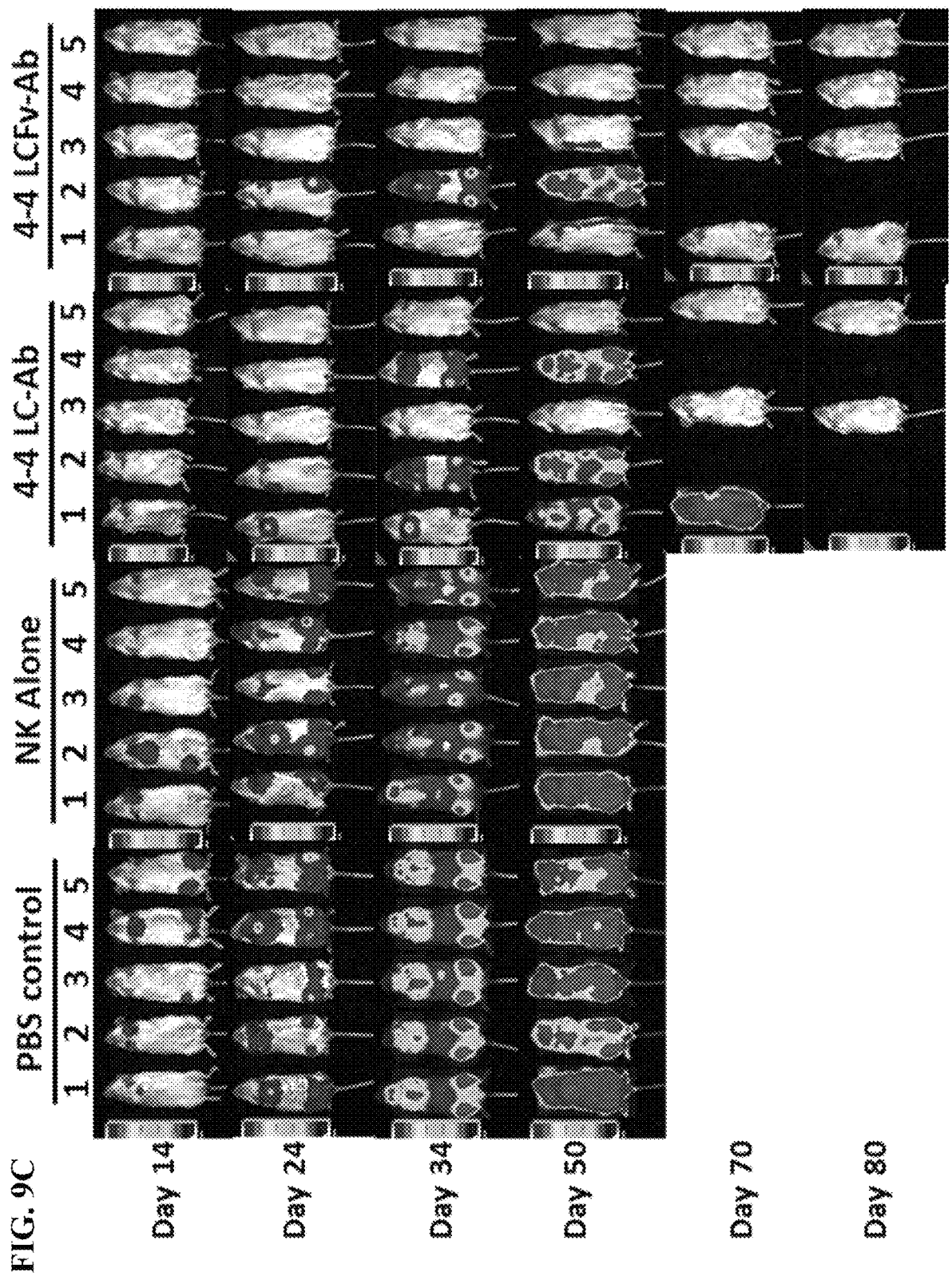
Figure 9D:
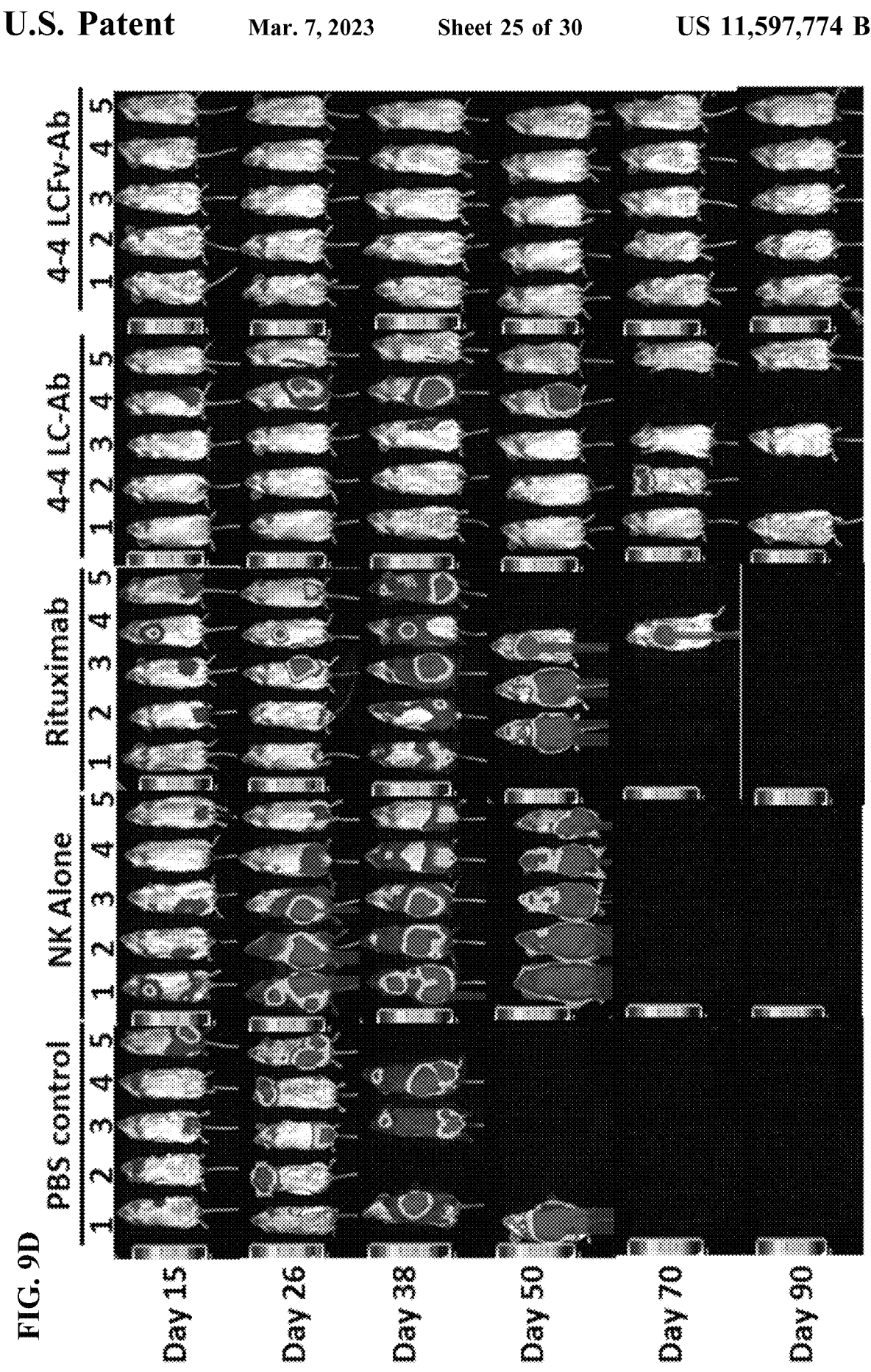
Figure 9E:
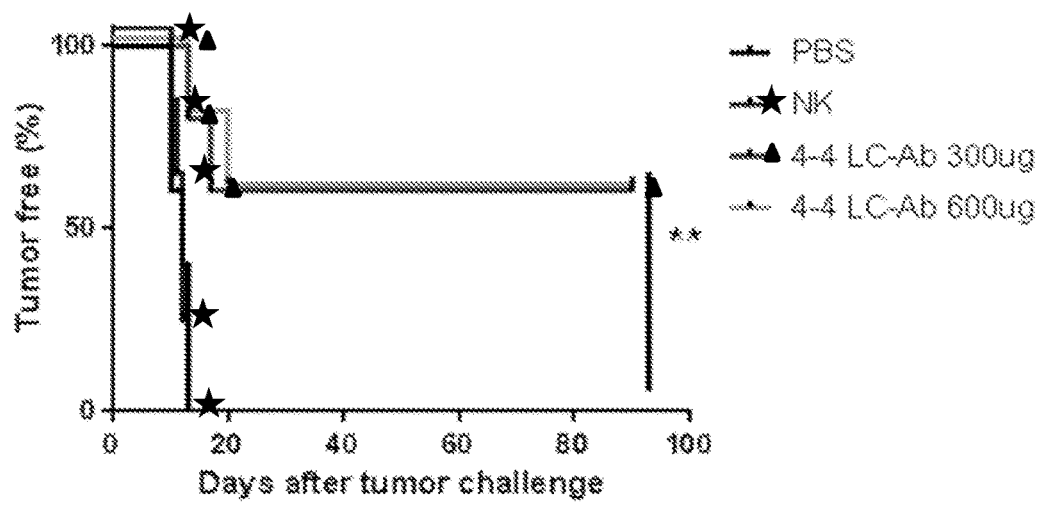
Figure 9F:
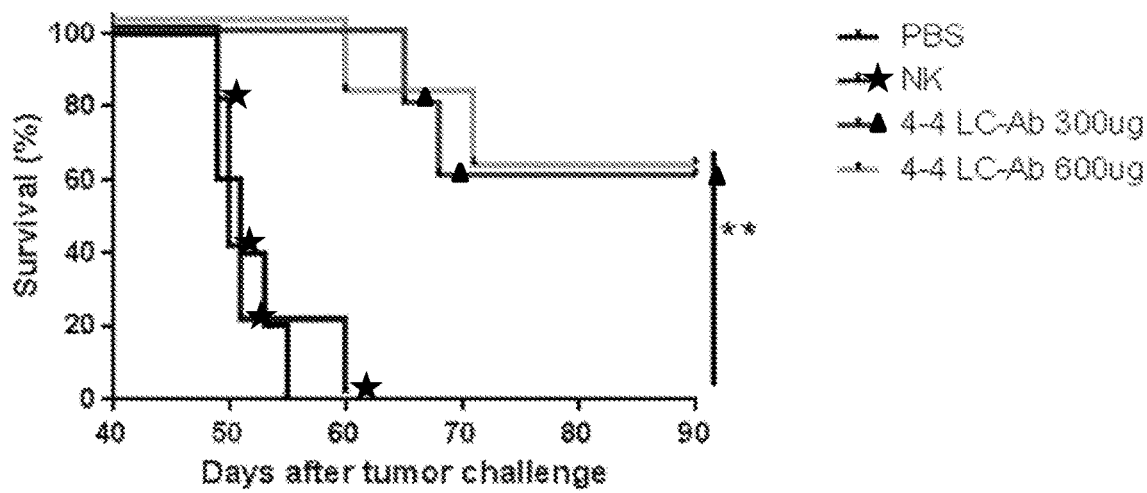
Figure 9G:
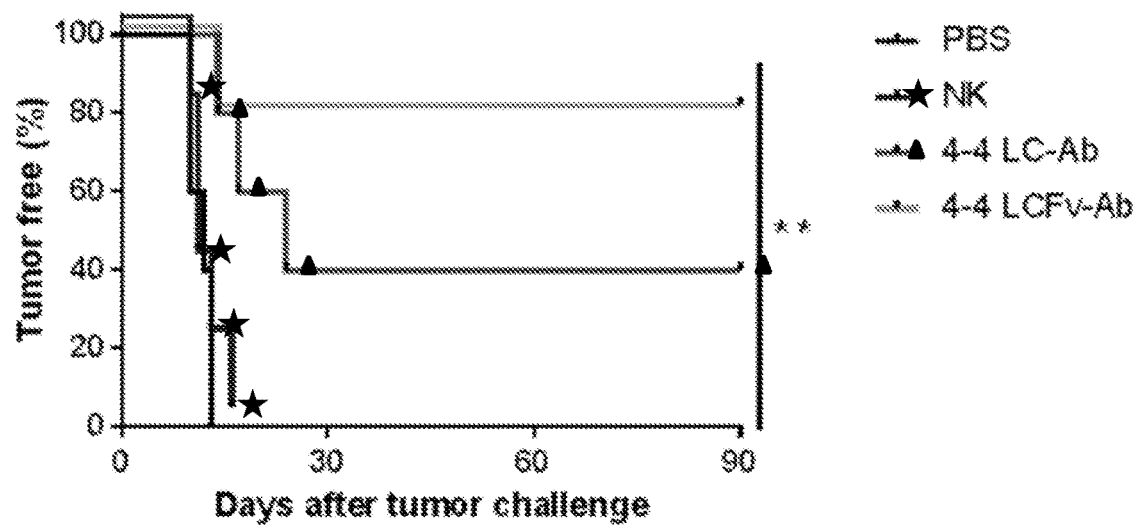
Figure 9H:
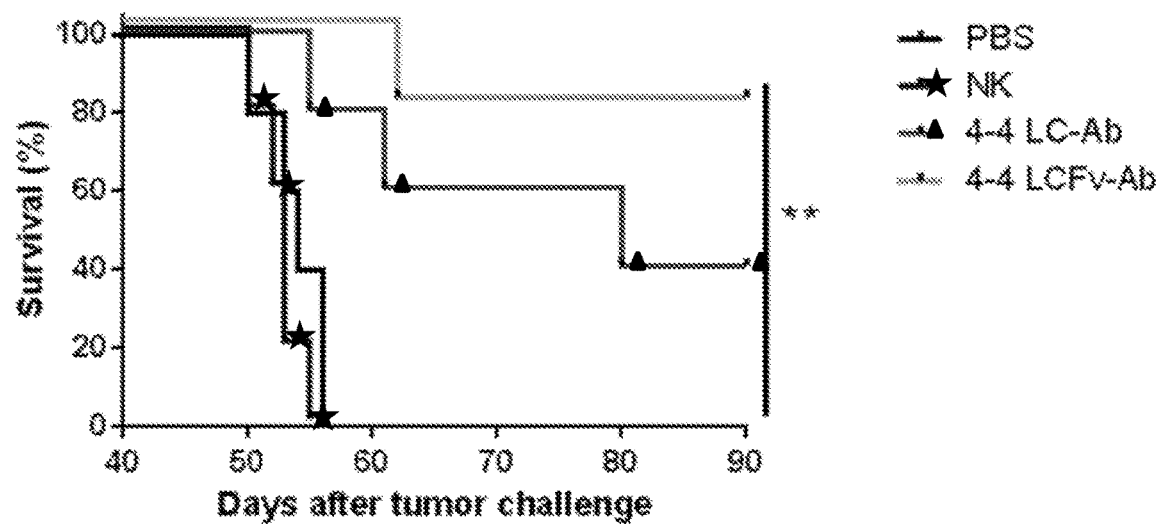
Figure 9I:
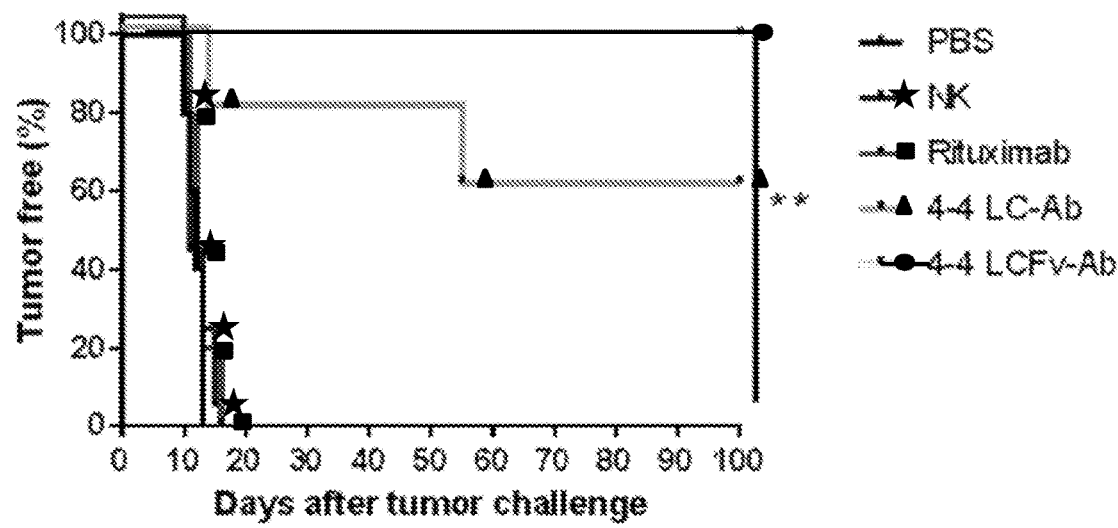
Figure 9J:
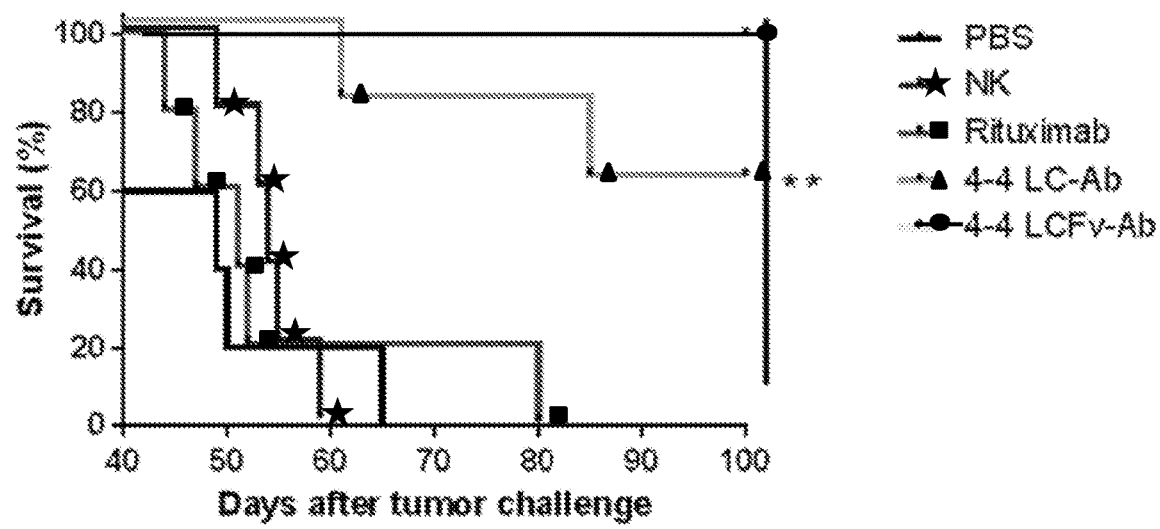
Figure 10:
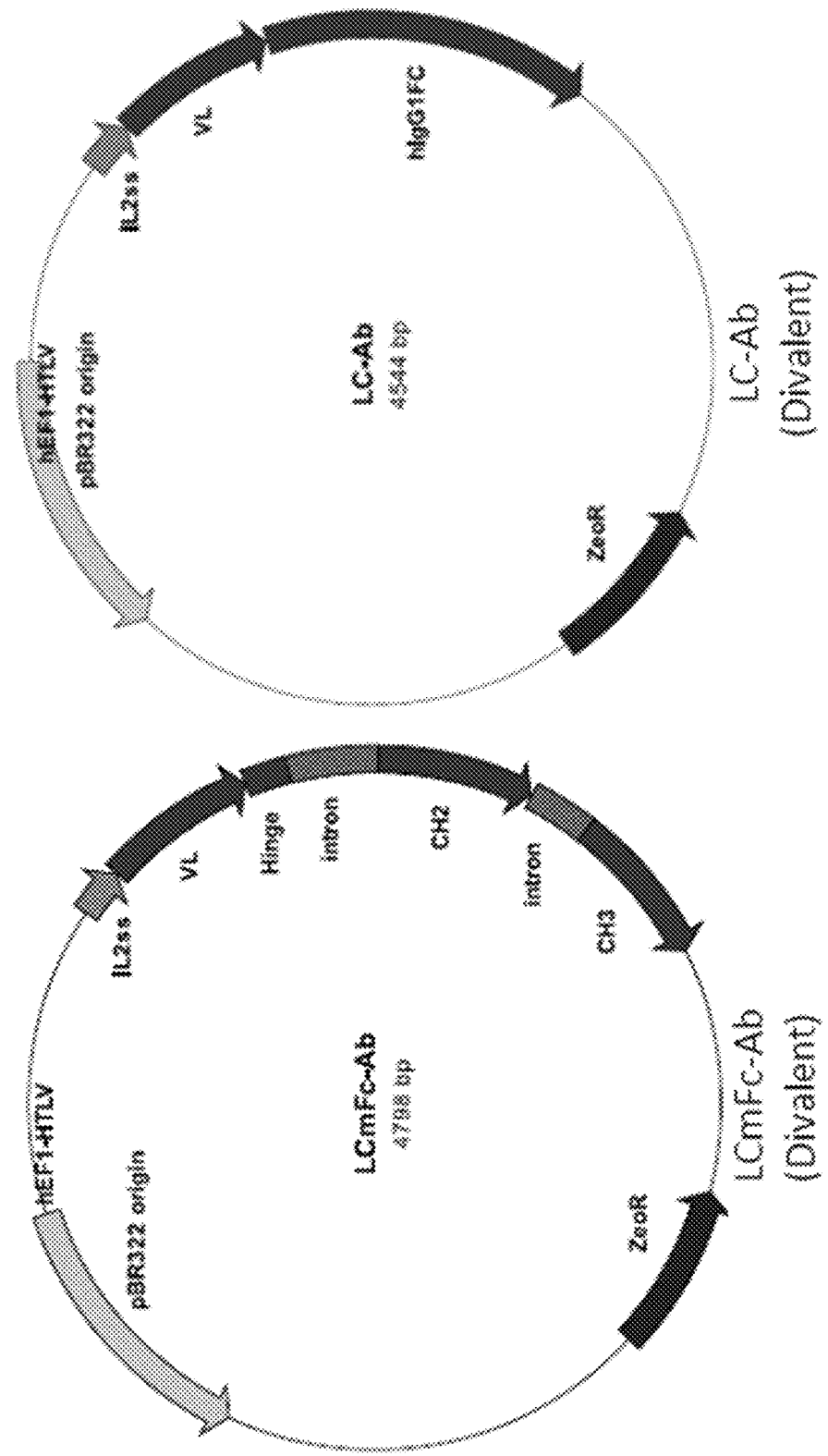
FIG. 10. Expression vectors encoding the antibody constructs shown in FIG. 2A.
Figure 10:
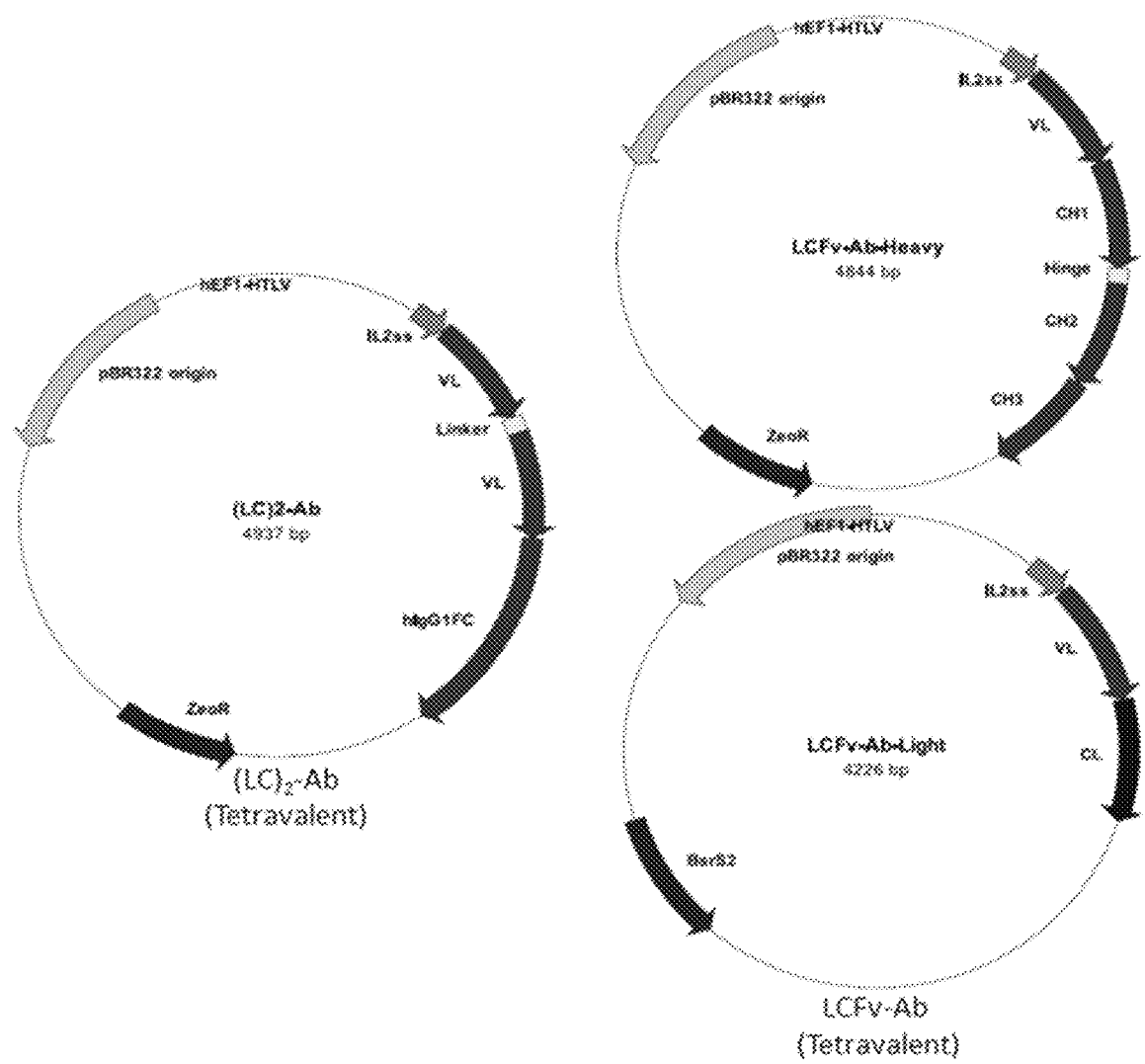

The antibody variable domain provided herein may form part of an antibody, antibody variant or antibody fragment. The antibody variable domain provided herein including embodiments thereof may form part of a single chain variable fragment (scFv). In embodiments, the antibody variable domain provided herein including embodiments thereof forms part of an antibody construct. The antibody construct may be an antibody construct as described herein including embodiments thereof. Thus, in another aspect is provided an antibody construct including a first antibody peptide, the first antibody peptide including: (i) a first antibody variable domain including a CDR 1 as set forth in SEQ ID NO:1, a CDR 2 as set forth in SEQ ID NO:2 and a CDR 3 as set forth in SEQ ID NO:3; and (ii) a first antibody domain bound to the first antibody variable domain. In embodiments, the antibody construct is a construct as depicted in FIG. 2A.

An "antibody construct" as provided herein refers to a recombinant polypeptide or recombinant polypeptide complex, which includes an antibody peptide (e.g., a first antibody peptide) including an antibody variable domain (e.g., first antibody variable domain) and an antibody domain. In embodiments, the antibody construct is an antibody, as described herein. In embodiments, the antibody construct is an antibody variant, as described herein. The antibody construct is capable of binding an antigen at least in part through said antibody variable domain and may be a monovalent or multivalent (e.g., divalent or tetravalent) polypeptide complex. The antibody construct provided herein may include one or more antibody variable domains (e.g., a first, second, third or fourth antibody variable domain) forming part of one or more antibody peptides (e.g., a first antibody peptide or a second antibody peptide). Therefore, the antibody construct may be able to bind an antigen at least in part through one or more (e.g., 2, 3, or 4) antibody variable domains and may therefore be referred to as a monovalent, a divalent or a tetravalent antibody construct, respectively.

The antibody construct as provided herein includes at least one antibody peptide. An "antibody peptide" as provided herein is a polypeptide including a combination of an antibody variable domain provided herein with one or more heavy chain constant domains (e.g., $CH_1$, $CH_2$, or $CH_3$) or fragments or variants thereof. A "heavy chain constant (CH) domain" as provided herein is a domain (e.g., heavy chain constant 1 ($CH_1$) domain, heavy chain constant 2 ($CH_2$) domain, heavy chain constant 3 ($CH_3$) domain), which forms part of a constant region of a heavy chain of an antibody or a fragment thereof.

In embodiments, the antibody peptide (e.g., first antibody peptide) includes an antibody light chain variable domain (e.g., first antibody light chain variable domain), a heavy chain constant 2 ($CH_2$) domain (e.g., first $CH_2$ domain) and a heavy chain constant 3 ($CH_3$) domain (e.g., first $CH_3$ domain). In embodiments, the antibody peptide includes a first antibody light chain variable domain, a second antibody light chain variable domain, a heavy chain constant 2 ($CH_2$) domain and a heavy chain constant 3 ($CH_3$) domain. In embodiments, the antibody peptide includes an antibody light chain variable domain, a heavy chain constant 1 ($CH_1$) domain, a heavy chain constant 2 ($CH_2$) domain and a heavy chain constant 3 ($CH_3$) domain. For the embodiments above, the order the domains and regions are listed corresponds to their order in the antibody peptide from the N-terminus to the C-terminus. Thus, in N-terminus to C-terminus direction the antibody peptide may include an antibody light chain variable domain, a heavy chain constant 2 ($CH_2$) domain and a heavy chain constant 3 ($CH_3$) domain. Further, in N-terminus to C-terminus direction the antibody peptide may include a first antibody light chain variable domain, a second antibody light chain variable domain, a heavy chain constant 2 ($CH_2$) domain and a heavy chain constant 3 ($CH_3$) domain or an antibody light chain variable domain, a heavy chain constant 1 ($CH_1$) domain, a heavy chain constant 2 ($CH_2$) domain and a heavy chain constant 3 ($CH_3$) domain.

As described above the antibody construct may include more than one antibody peptide. In embodiments, the antibody construct includes a first antibody peptide and a second antibody peptide bound to each other. The first antibody peptide may be bound to the second antibody peptide through a chemical linker. The first antibody peptide may be bound to the second antibody peptide through a covalent bond. The first antibody peptide may be bound to the second antibody peptide through a non-covalent bond. The first antibody peptide may be bound to the second antibody peptide to form a dimer.

The antibody construct may further include a first light chain antibody peptide and a second light chain antibody peptide, wherein the first light chain antibody peptide and the first antibody peptide are bound together and the second light chain antibody peptide and the second antibody peptide are bound together. A light chain antibody peptide as provided herein refers to a polypeptide including an antibody variable domain as provided herein and a light chain constant region/domain (CL). A "light chain constant (CL) domain" as provided herein refers to the constant region of a light chain of an antibody or a fragment thereof. In embodiments, the light chain antibody peptide (first or second light chain antibody peptide) includes an antibody light chain variable domain and a light chain constant domain (CL). Thus, in N-terminus to C-terminus direction the light chain antibody peptide may include an antibody light chain variable domain and a light chain constant domain (CL). The first light chain antibody peptide may be bound to the first antibody peptide through a chemical linker (covalent or non-covalent) and the second light chain antibody peptide may be bound to the second antibody peptide through a chemical linker (covalent or non-covalent).

An "antibody domain" as referred to herein is a portion of a polypeptide including a heavy chain constant region (CH) as described above. An antibody domain may include one or more heavy chain constant domains (e.g., CH1, CH2, and CH3). In embodiments, the antibody domain includes a constant heavy chain 2 (CH2) domain and a constant heavy chain 3 (CH3) domain. In embodiments, the antibody domain includes a constant heavy chain 1 (CH1) domain, a constant heavy chain 2 (CH2) domain and a constant heavy chain 3 (CH3) domain. In N-terminus to C-terminus direction, the antibody domain may include a constant heavy chain 2 (CH2) domain and a constant heavy chain 3 (CH3)

domain. In embodiments, the antibody domain includes in N-terminus to C-terminus direction a constant heavy chain 1 (CH1) domain, a constant heavy chain 2 (CH2) domain and a constant heavy chain 3 (CH3) domain. In embodiments, the antibody domain is a human antibody domain. In embodiments, the antibody domain is a mouse antibody domain. In embodiments, the antibody domain is a constant heavy chain. A "constant heavy chain" provided herein is a peptidyl moiety including one or more heavy chain constant domains of an antibody.

In embodiments, the antibody construct is a monovalent antibody construct. A monovalent antibody construct as provided herein refers to an antibody construct including a first antibody peptide including one antibody variable domain (e.g., a first antibody variable domain), wherein the construct binds to an antigen at least in part through said one antibody variable domain. A monovalent antibody construct as provided herein may be a single chain antibody (scFv), wherein the antibody variable domain (e.g., first antibody variable domain) is bound to a variable heavy chain domain (e.g., first variable heavy chain domain) through a chemical linker (e.g., peptide linker). A "variable heavy chain domain" as provided herein is a peptidyl moiety including FRs (framework regions) and CDRs and capable of binding to an antigen. In embodiments, a variable heavy chain domain includes a variable heavy chain (VH). In embodiments, a variable heavy chain domain is a variable heavy chain (VH). Thus, in embodiments, the first antibody domain is a first variable heavy chain domain. In embodiments, the antibody construct is a single chain antibody (scFv). In embodiments, the antibody construct is a single domain antibody (nanobody).

A monovalent antibody construct provided herein may include a first antibody peptide including a first antibody variable domain bound through a chemical linker to a first antibody domain. In embodiments, the chemical linker is a covalent linker. In embodiments, the linker is a bond. In embodiments, the first antibody domain is a first constant heavy chain. In embodiments, the first constant heavy chain includes a first constant heavy chain 2 (CH2) domain bound to a first constant heavy chain 3 (CH3) domain. In embodiments, the first CH3 domain is bound to the first antibody variable domain through the first CH2 domain. In embodiments, the first constant heavy chain 2 (CH2) domain is bound to said first constant heavy chain 3 (CH3) domain through a covalent linker. In further embodiments, the first constant heavy chain 2 (CH2) domain is bound to said first constant heavy chain 3 (CH3) domain through a bond.

The first antibody peptide provided herein may include one or more constant heavy chain domains (e.g., CH1, CH2, CH3). In embodiments, the first antibody peptide further includes a first constant heavy chain 1 (CH1) domain. In embodiments, the first CH1 domain forms part of a first antibody domain. In embodiments, the first antibody variable domain is bound to the first antibody domain through the first CH1 domain. In embodiments, the first antibody variable domain is bound to the first CH1 domain through a chemical linker. In embodiments, the first antibody variable domain is bound to the first CH1 domain through a bond. In embodiments, the first antibody variable domain is bound to the first CH2 domain through the first CH1 domain. In embodiments, the first $CH_2$ domain is bound to the first $CH_1$ domain through a chemical linker. In embodiments, the first CH2 domain is bound to the first CH1 domain through a peptide linker.

In one embodiment, the first antibody variable domain is an antibody light chain variable domain, the first antibody domain is a first constant heavy chain consisting of a first CH2 domain bound to a first CH3 domain, wherein the first antibody variable domain is bound to the first CH3 domain through the first CH2 domain. In one other embodiment, the first antibody variable domain is an antibody light chain variable domain, the first antibody domain is a first constant heavy chain consisting of a first CH1 domain bound to a first CH3 domain through a first CH2 domain, wherein the first antibody variable domain is bound to the CH2 domain through the CH1 domain.

The antibody construct provided herein including embodiments thereof may be a divalent antibody construct. Where the antibody construct provided herein is a divalent construct the antibody construct includes a second antibody variable domain. In a divalent antibody construct the second antibody variable domain may form part of the first antibody peptide. Where the second antibody variable domain forms part of the first antibody peptide, the second antibody variable domain is bound to the antibody domain through the first antibody variable domain. Thus, in embodiments, the first antibody peptide includes a second antibody variable domain bound to the antibody domain through the first antibody variable domain. In one embodiment, the first antibody variable domain is a first antibody light chain variable domain, the second antibody variable domain is a second antibody light chain variable domain and the first antibody domain is a first constant heavy chain consisting of a first CH2 domain bound to a first CH3 domain, wherein the second antibody variable domain is bound to the first antibody domain through the first antibody variable domain.

Alternatively, the second antibody variable domain may form part of a second antibody peptide. Thus, in embodiments, the antibody construct is a divalent antibody construct further including a second antibody peptide bound to the first antibody peptide. The second antibody peptide may be bound to the first antibody peptide through a chemical linker to form a dimer. The chemical linker may be a covalent linker. In embodiments, the chemical linker is a disulfide linker. In embodiments, the second antibody peptide is bound to the first antibody domain. In embodiments, the second antibody peptide is bound to the first CH2 domain. In embodiments, the second antibody peptide is bound through a disulfide linker to the first antibody domain.

In embodiments, the second antibody peptide and the first antibody peptide are chemically identical. In embodiments, the second antibody peptide and the first antibody peptide are chemically different. Thus, in embodiments, the first antibody peptide bound to the second antibody peptide forms a homodimer. In embodiments, the first antibody peptide bound to the second antibody peptide forms a heterodimer.

As described above the first antibody peptide and the second antibody peptide may be chemically identical. Therefore, the second antibody peptide provided herein may include identical domains (e.g., antibody variable domain and antibody domain) having the same chemical composition as the first antibody peptide. Thus, the second antibody peptide provided herein may include (i) a second antibody variable domain; and (ii) a second antibody domain bound to the second antibody variable domain. Thus, in embodiments, the second antibody variable domain includes a CDR 1 as set forth in SEQ ID NO:1, a CDR 2 as set forth in SEQ ID NO:2 and a CDR 3 as set forth in SEQ ID NO:3.

In embodiments, the second antibody domain is a second constant heavy chain. In embodiments, the second constant heavy chain includes a second constant heavy chain 2 (CH2) domain bound to a second constant heavy chain 3 (CH3)

domain. In embodiments, the second constant heavy chain 2 (CH2) domain is bound to the second antibody variable domain through a chemical linker. In embodiments, the second constant heavy chain 2 (CH2) domain is bound to the second antibody variable domain through a bond. In embodiments, the second CH3 domain is bound to the second antibody variable domain through the second CH2 domain. In embodiments, the second CH3 domain is bound to the second CH2 domain through a chemical linker. In embodiments, the second CH3 domain is bound to the second CH2 domain through a bond.

In one embodiment, the first antibody variable domain is an antibody light chain variable domain, the second antibody variable domain is a second antibody light chain variable domain, the first antibody domain is a first constant heavy chain consisting of a first CH2 domain bound to a first CH3 domain and the second antibody domain is a second constant heavy chain consisting of a second CH2 domain bound to a second CH3 domain, wherein the first antibody peptide and the second antibody peptide are bound together.

In embodiments, the second antibody peptide further includes a second constant heavy chain 1 (CH1) domain. In embodiments, the second CH1 domain forms part of the second antibody domain. In embodiments, the second antibody variable domain is bound to the second antibody domain through the second CH1 domain. In embodiments, the second antibody variable domain is bound to the second CH1 domain through a chemical linker. In embodiments, the second antibody variable domain is bound to the second CH1 domain through a bond. In embodiments, the second antibody variable domain is bound to the second CH2 domain through the second CH1 domain. In embodiments, the second CH2 domain is bound to the second CH1 domain through a chemical linker. In embodiments, the second CH2 domain is bound to the second CH1 domain through a peptide linker.

In embodiments, the first CH1 domain and the second CH1 domain are bound together. In embodiments, the first CH1 domain and the second CH1 domain are bound through a chemical linker.

The antibody construct provided herein including embodiments thereof may be tetravalent antibody constructs. Where the antibody construct provided herein including embodiments thereof is a tetravalent antibody construct the antibody construct includes four antibody variable domains provided herein (e.g., first, second, third and fourth antibody variable domain). In a tetravalent antibody construct the third antibody variable domain may form part of the first antibody peptide and the fourth antibody variable domain may form part of the second antibody peptide. Where the third antibody variable domain forms part of the first antibody peptide and the fourth antibody variable domain forms part of the second antibody peptide, the third antibody variable domain is bound to the first antibody domain through the first antibody variable domain and the fourth antibody variable domain is bound to the second antibody domain through the second antibody variable domain. Therefore, the first antibody peptide may include a third antibody variable domain bound to the first antibody domain through the first antibody variable domain and the second antibody peptide may include a fourth antibody variable domain bound to the second antibody domain through the second antibody variable domain. Thus, in embodiments, the antibody construct is a tetravalent antibody construct further including a third antibody variable domain bound to the first antibody peptide and a fourth antibody variable domain bound to the second antibody peptide. In embodiments, the third antibody variable domain forms part of the first antibody peptide and the fourth antibody variable domain forms part of the second antibody peptide. In embodiments, the third antibody variable domain is bound to the first antibody domain through the first antibody variable domain. In embodiments, the third antibody variable domain is bound to the first CH2 domain through the first antibody variable domain. In embodiments, the fourth antibody variable domain is bound to the second antibody domain through the second antibody variable domain. In embodiments, the fourth antibody variable domain is bound to the second CH2 domain through the second antibody variable domain.

In one embodiment, the first antibody variable domain is a first antibody light chain variable domain, the second antibody variable domain is a second antibody light chain variable domain, the third antibody variable domain is a third antibody light chain variable domain, the fourth antibody variable domain is a fourth antibody light chain variable domain, the first antibody domain is a first constant heavy chain consisting of a first CH2 domain bound to a first CH3 domain and the second antibody domain is a second constant heavy chain consisting of a second CH2 domain bound to a second CH3 domain, wherein the first antibody peptide and the second antibody peptide are bound together.

Alternatively, the third antibody variable domain may form part of a first light chain antibody peptide and the fourth antibody variable domain may form part of a second light chain antibody peptide, wherein the first light chain antibody peptide is bound to the first antibody peptide and the second light chain antibody peptide is bound to the second antibody peptide. The first light chain antibody peptide may be bound to the first antibody peptide through a chemical linker. The first light chain antibody peptide may be bound to the first antibody peptide through a covalent linker. The first light chain antibody peptide may be bound to the first antibody peptide through a disulfide linker. The second light chain antibody peptide may be bound to the second antibody peptide through a chemical linker. The second light chain antibody peptide may be bound to the second antibody peptide through a covalent linker. The second light chain antibody peptide may be bound to the second antibody peptide through a disulfide linker. Thus, in embodiments, the third antibody variable domain forms part of a first light chain antibody peptide bound to the first antibody peptide and the fourth antibody variable domain forms part of a second light chain antibody peptide bound to the second antibody peptide.

In embodiments, the first light chain antibody peptide includes a first constant light chain 1 (CL1) domain bound to the third antibody variable domain. In embodiments, the first light chain antibody peptide is bound to the first antibody peptide through the first CL1 domain. In embodiments, the first CL1 domain is bound to the first CH1 domain through a chemical linker. In embodiments, the first CL1 domain is bound to the first CH1 domain through a disulfide linker. In embodiments, the third antibody variable domain is bound to the first antibody peptide through the first CL1 domain.

In embodiments, the second light chain antibody peptide includes a second constant light chain 1 (CL1) domain bound to the fourth antibody variable domain. In embodiments, the second light chain antibody peptide is bound to the second antibody peptide through the second CL1 domain. In embodiments, the second CL1 domain is bound to the second CH1 domain through a chemical linker. In embodiments, the second CL1 domain is bound to the second CH1 domain through a disulfide linker. In embodiments, the fourth antibody variable domain is bound to the second antibody peptide through the second CL1 domain.

In one embodiment, the first antibody variable domain is a first antibody light chain variable domain, the second antibody variable domain is a second antibody light chain variable domain, the third antibody variable domain is a third antibody light chain variable domain, the fourth antibody variable domain is a fourth antibody light chain variable domain, the first antibody domain is a first constant heavy chain consisting of a first CH1 domain bound to a first CH3 domain through a first CH2 domain, the second antibody domain is a second constant heavy chain consisting of a second CH1 domain bound to a second CH3 domain through a second CH2 domain, wherein the third antibody variable domain forms part of the first antibody light chain peptide and the fourth antibody variable domain forms part of the second antibody light chain peptide, the first antibody light chain peptide is bound to the first antibody peptide and the second antibody light chain peptide is bound to the second antibody peptide. In one further embodiment, the first antibody peptide and the second antibody peptide are bound together.

The antibody constructs provided herein are recombinant polypeptides that may include parts or fragments of an antibody (e.g., CDRs, FRs, VL, VH, CH1, CH2, CH3 domains). In embodiments, the antibody construct is an antibody. In embodiments, the antibody construct is an antibody variant.

In embodiments, the antibody construct is a Fab' fragment. In embodiments, the antibody construct is a chimeric antibody. In embodiments, the antibody construct is a humanized antibody. In embodiments, the antibody construct is a human antibody.

The antibody constructs provided herein are contemplated for therapeutic uses. The ability of the antibody constructs provided herein to specifically target cancer cells and avoid healthy cells makes them, inter alia, useful for cancer therapeutics. The antibody constructs provided herein, including embodiments thereof, while conveying lysis of cancer cells, may include a further therapeutic agent and/or administered with a further therapeutic agent useful in treating or preventing a disease such as cancer. In embodiments, the antibody constructs or the antibody variable domain is conjugated or otherwise covalently bound to a therapeutic agent. In embodiments, the antibody constructs or the antibody variable domain is and antibody-drug conjugate.

The antibody constructs provided herein are further contemplated for use in diagnostics. The ability of the antibody constructs provided herein to specifically target cancer cells and avoid healthy cells makes them uniquely useful for accurate diagnosis of cancer.

Therefore, the antibody constructs provided herein, including embodiments thereof, may be equipped with one or more detectable moieties to allow detection of cancer cells.

In embodiments, the antibody construct includes a detectable moiety. The detectable moiety may be bound to the antibody construct through a chemical linker as described above. In embodiments, the detectable moiety is a fluorescent moiety.

In embodiments, the antibody construct is bound to a cancer protein. A "cancer protein" as provided herein refers to any protein (e.g., surface receptor, secreted peptide, or signaling peptide) that is expressed by cancer cells but not healthy cells. In embodiments, the cancer protein forms part of a cancer cell. In embodiments, the cancer cell is a lymphoid cell. In embodiments, the cancer cell is a B cell. In embodiments, the cancer cell is a mantle cell lymphoma (MCL) cell. In embodiments, the antibody construct does not bind to a non-cancer cell. In embodiments, the antibody construct does not bind to a non-cancer cell relative to a standard control. In embodiments, the antibody construct does not detectably bind to a non-cancer cell.

In one embodiment, the antibody construct is a divalent antibody construct including the first antibody peptide bound to the second antibody peptide, wherein the first antibody peptide includes a first antibody light chain variable domain bound to a first constant heavy chain 3 (CH3) domain through a first constant heavy chain 2 (CH2) domain, and the second antibody peptide includes a second antibody light chain variable domain bound to a second constant heavy chain 3 (CH3) domain through a second constant heavy chain 2 (CH2) domain. In embodiments, the first CH2 domain is a murine CH2 domain, the first CH3 domain is a murine CH3 domain, the second CH2 domain is a murine CH2 domain, and the second CH3 domain is a murine CH3 domain.

In one embodiment, the antibody construct is a divalent antibody construct including the first antibody peptide bound to the second antibody peptide, wherein the first antibody peptide includes a first antibody light chain variable domain bound to a first constant heavy chain 3 (CH3) domain through a first constant heavy chain 2 (CH2) domain, and the second antibody peptide includes a second antibody light chain variable domain bound to a second constant heavy chain 3 (CH3) domain through a second constant heavy chain 2 (CH2) domain. In embodiments, the first CH2 domain is a human CH2 domain, the first CH3 domain is a human CH3 domain, the second CH2 domain is a human CH2 domain, and the second CH3 domain is a human CH3 domain.

Nucleic Acids Compositions

Further provided are isolated nucleic acids encoding the antibody constructs described herein, including embodiments thereof. The term "encoding" or "encodes" is used in its customary sense to specify that the nucleic acid includes the genetic code necessary to produce a protein.

In embodiments is provided an isolated nucleic acid encoding the antibody variable domain as described herein, including embodiments thereof. In one aspect, provided is an isolated nucleic acid encoding the first antibody peptide as described herein, including embodiments thereof. In one aspect, provided is an isolated nucleic acid encoding the second antibody peptide as described herein, including embodiments thereof. In one aspect, provided is an isolated nucleic acid encoding the first light chain antibody peptide as described herein, including embodiments thereof. In one aspect, provided is an isolated nucleic acid encoding the second light chain antibody peptide as described herein, including embodiments thereof.

In embodiments, the isolated nucleic acid includes the sequence of SEQ ID NO:4, SEQ ID NO:6, SEQ ID NO:7, SEQ ID NO:8 or SEQ ID NO:9. In embodiments, the isolated nucleic acid includes the sequence of SEQ ID NO:6. In embodiments, the isolated nucleic acid includes the sequence of SEQ ID NO:7. In embodiments, the isolated nucleic acid includes the sequence of SEQ ID NO:8. In embodiments, the isolated nucleic acid includes the sequence of SEQ ID NO:9.

In embodiments, the antibody construct is encoded by an isolated nucleic acid including the sequence of SEQ ID NO:4, SEQ ID NO:6, SEQ ID NO:7, SEQ ID NO:8 or SEQ ID NO:9. In embodiments, the antibody construct is encoded by an isolated nucleic acid including the sequence of SEQ ID NO:4. In embodiments, the antibody construct is encoded by an isolated nucleic acid including the sequence of SEQ ID NO:6. In embodiments, the antibody construct is encoded by an isolated nucleic acid including the sequence of SEQ ID NO:7. In embodiments, the antibody construct is encoded by an isolated nucleic acid including the sequence of SEQ ID NO:8. In embodiments, the antibody construct is encoded by an isolated nucleic acid including the sequence of SEQ ID NO:9. In embodiments, the antibody variable domain is encoded by a nucleic acid including SEQ ID NO:4. In embodiments, the antibody variable domain is encoded by SEQ ID NO:4.

In one embodiment is provided an isolated nucleic acid encoding in 5' to 3' direction a first antibody light chain variable domain, a peptide linker, a first CH2 domain and a first CH3 domain. In one further embodiment, the first antibody light chain variable domain is encoded by a nucleic acid including SEQ ID NO:4. In one further embodiment, the first CH2 domain and the first CH3 domain are encoded by a nucleic acid including SEQ ID NO:6. In one further embodiment, SEQ ID NO:4 and SEQ ID NO:6 form part of the same nucleic acid. In one embodiment, the isolated nucleic acid includes SEQ ID NO:4 and SEQ ID NO:6.

In one embodiment is provided an isolated nucleic acid encoding in 5' to 3' direction a first antibody light chain variable domain, a second antibody light chain variable domain, a first CH2 domain and a first CH3 domain. In one further embodiment, the first antibody light chain variable domain is encoded by a nucleic acid including SEQ ID NO:4 and the second antibody light chain variable domain is encoded by a nucleic acid including SEQ ID NO:4. In one further embodiment, the first CH2 domain and the first CH3 domain are encoded by a nucleic acid including SEQ ID NO:6. In one further embodiment, SEQ ID NO:4 and SEQ ID NO:6 form part of the same nucleic acid. In one embodiment, the isolated nucleic acid includes SEQ ID NO:4 and SEQ ID NO:6.

In one embodiment is provided an isolated nucleic acid encoding in 5' to 3' direction a first antibody light chain variable domain, a first CH1 domain, a peptide linker, a first CH2 domain and a first CH3 domain. In one further embodiment, the first antibody light chain variable domain is encoded by a nucleic acid including SEQ ID NO:4. In one further embodiment, the first CH1 domain, the first CH2 domain and the first CH3 domain are encoded by a nucleic acid including SEQ ID NO:8. In one further embodiment, SEQ ID NO:4 and SEQ ID NO:8 form part of the same nucleic acid. In one embodiment, the isolated nucleic acid includes SEQ ID NO:4 and SEQ ID NO:8.

In one embodiment is provided an isolated nucleic acid encoding in 5' to 3' direction a first antibody light chain variable domain and a first constant light chain (CL1). In one further embodiment, the first antibody light chain variable domain is encoded by a nucleic acid including SEQ ID NO:4. In one further embodiment, the first constant light chain (CL1) is encoded by a nucleic acid including SEQ ID NO:9. In one further embodiment, SEQ ID NO:4 and SEQ ID NO:9 form part of the same nucleic acid. In one embodiment, the isolated nucleic acid includes SEQ ID NO:4 and SEQ ID NO:9.

Pharmaceutical Compositions

In embodiments is provided a pharmaceutical composition including a therapeutically effective amount of the antibody variable domain as described herein, including embodiments thereof, or the antibody construct as described herein, including embodiments thereof, and a pharmaceutically acceptable excipient. In embodiments is provided a pharmaceutical composition including a therapeutically effective amount of the antibody variable domain as described herein, including embodiments thereof, and a pharmaceutically acceptable excipient. In embodiments is provided a pharmaceutical composition including a therapeutically effective amount of the antibody construct as described herein, including embodiments thereof, and a pharmaceutically acceptable excipient.

A "therapeutically effective amount" as provided herein refers to an amount effective to achieve its intended purpose. The actual amount effective for a particular application will depend, inter alia, on the condition being treated. When administered in methods to treat a disease, the pharmaceutical compositions described herein will contain an amount of active antibody construct effective to achieve the desired result, e.g., reducing, eliminating, or slowing the progression of disease symptoms (e.g., cancer). Determination of a therapeutically effective amount of an antibody construct provided herein is well within the capabilities of those skilled in the art, especially in light of the detailed disclosure herein.

Acceptable carriers, excipients or stabilizers are nontoxic to recipients at the dosages and concentrations employed, and include buffers such as phosphate, citrate, or acetate at a pH typically of 5.0 to 8.0, most often 6.0 to 7.0; salts such as sodium chloride, potassium chloride, etc. to make isotonic; antioxidants, preservatives, low molecular weight polypeptides, proteins, hydrophilic polymers such as polysorbate 80, amino acids such as glycine, carbohydrates, chelating agents, sugars, and other standard ingredients known to those skilled in the art (Remington's Pharmaceutical Science $16^{th}$ edition, Osol, A. Ed. 1980). The antibody construct is typically present at a concentration of 0.1-100 mg/ml, e.g., 1-10 mg/ml or 10-50 mg/ml, for example 5, 10, 20, 30, 40, 50 or 60 mg/ml.

A pharmaceutical composition including an antibody construct as described herein can be administered by a variety of methods known in the art. The route and/or mode of administration vary depending upon the desired results. In embodiments, administration is intravenous, intramuscular, intraperitoneal, or subcutaneous, or administered proximal to the site of the target. Pharmaceutically acceptable excipients can be suitable for intravenous, intramuscular, subcutaneous, parenteral, spinal or epidermal administration (e.g., by injection or infusion).

Pharmaceutical compositions of the antibody construct can be prepared in accordance with methods well known and routinely practiced in the art. See, e.g., Remington: *The Science and Practice of Pharmacy*, Mack Publishing Co., $20^{th}$ ed., 2000; and *Sustained and Controlled Release Drug Delivery Systems*, J. R. Robinson, ed., Marcel Dekker, Inc., New York, 1978. Pharmaceutical compositions are preferably manufactured under GMP conditions. Typically, a therapeutically effective dose or efficacious dose of the antibody construct is employed in the pharmaceutical compositions of the invention. The antibody constructs provided can be formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It may be advantageous to formulate the antibody constructs in combination with other therapies or agents. It can be advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of antibody construct calculated to produce the desired therapeutic effect in association with the required pharmaceutical excipient.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular antibody being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibody constructs of the invention employed in the pharmaceutical composition at levels lower than that required to achieve the desired therapeutic effect and gradually increase the dosage until the desired effect is achieved. In general, effective doses of the compositions of the present invention vary depending upon many different factors, including the specific disease or condition to be treated, means of administration, target site, physiological state of the patient, whether the patient is human or an animal, other medications administered, and whether treatment is prophylactic or therapeutic. Treatment dosages need to be titrated to optimize safety and efficacy. For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months.

The antibody constructs provided herein can be administered on multiple occasions. Intervals between single dosages can be weekly, monthly or yearly. Intervals can also be irregular as indicated by measuring blood levels of the antibody construct in the patient. In some methods, dosage is adjusted to achieve a plasma antibody construct concentration of 1-1000 μg/ml and in some methods 25-300 μg/ml. Alternatively, antibody can be administered as a sustained release formulation, in which case less frequent administration is required. Dosage and frequency vary depending on the half-life of the antibody construct in the patient. In general, humanized antibodies (e.g., antibody constructs) show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Methods of Treatment

In embodiments is provided a method of treating cancer in a subject in need thereof, the method including administering to a subject a therapeutically effective amount of the antibody variable domain as described herein, including embodiments thereof, or the antibody construct as described herein, including embodiments thereof, thereby treating cancer in the subject.

In embodiments is provided a method of treating cancer in a subject in need thereof, the method including administering to a subject a therapeutically effective amount of the antibody variable domain as described herein, including embodiments thereof, thereby treating cancer in the subject.

In embodiments is provided a method of treating cancer in a subject in need thereof, the method including administering to a subject a therapeutically effective amount of the antibody construct as described herein, including embodiments thereof, thereby treating cancer in the subject.

In embodiments, the cancer is lymphoma, leukemia or myeloma. In embodiments, the cancer is lymphoma. In embodiments, the cancer is myeloma.

In embodiments, the lymphoma is mantle cell lymphoma, follicular lymphoma, diffuse large B-cell lymphoma, marginal zone lymphoma or Burkitt's lymphoma. In embodiments, the lymphoma is mantle cell lymphoma. In embodiments, the lymphoma is follicular lymphoma. In embodiments, the lymphoma is diffuse large B-cell lymphoma. In embodiments, the lymphoma is marginal zone lymphoma. In embodiments, the lymphoma is Burkitt's lymphoma.

In embodiments, the leukemia is lymphoblastic leukemia, chronic lymphocytic leukemia or hairy cell leukemia. In embodiments, the leukemia is lymphoblastic leukemia. In embodiments, the leukemia is chronic lymphocytic leukemia. In embodiments, the leukemia is hairy cell leukemia.

In embodiments, the method further includes administering to the subject a second therapeutic agent. As described above, a therapeutic agent is a composition useful in treating or preventing a disease such as cancer. In embodiments, the second therapeutic agent is an anti-cancer agent.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclizimab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin Il (including recombinant interleukin II, or rlL.sub.2), interferon alfa-2a; interferon alfa-2b; interferon alfa-n1; interferon alfa-n3; interferon beta-1a; interferon gamma-1tb; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol.™ (i.e. paclitaxel), Taxotere.™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F$_{037}$), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to 111In, 90Y, or 131I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF$_{299804}$, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

In one aspect, a method of inducing cell lysis in a cancer cell is provided. The method includes, in contacting a cancer cell with an effective amount of the antibody variable domain as described herein, including embodiments thereof, or the antibody construct as described herein, including embodiments thereof, and an effector cell, thereby inducing cell lysis in the cancer cell. In embodiments, the contacting occurs in a cancer patient. In embodiments, the contacting occurs in vitro. In embodiments, the effector cell is a natural killer (NK) cell.

EXAMPLES

Example 1: Development of a Mantle Cell Lymphoma-Specific Fully Human Antibody

New cancer immunotherapies are rapidly entering the clinic due to their promising potency. Monoclonal antibodies and antibody-based immunotherapeutics are particularly attractive platforms due to high specificity and proven antitumor effects. Immunotherapeutics are currently developed against a range of targets; however, all pursue tumor-associated targets that are simultaneously present on malignant cells and their benign counterparts. Consequently, these therapeutic agents will inevitably deplete healthy, non-malignant cells in the process of eliminating tumors. Inability to differentiate cancerous from benign cells has limited antibody development and diminishes the success of immunotherapies. Therefore, developing therapeutics specifically targeting tumor cells had been an attractive yet elusive concept.

Deploying Applicants' de novo cell screening technology, Applicants successfully identified a novel mantle cell lymphoma (MCL)-specific, human antibody light chain binding domain (VL) with no recognition of normal human B cells. The cell screening technology incorporates Applicant's unique human antibody library onto phage display technology designed for novel target discovery. The library is comprised of high-diversity human antibody variable fragments (Fv) filtered to exclude Fv sequences that bind normal human tissue. Applicants screened human MCL line JeKo-1 and successfully identified a MCL-specific VL. The VL was engineered into novel human light chain domain antibody variants: LC-Ab, (LC)$_2$-Ab, and LCFv-Ab. The variants demonstrated the specificity of the VL-based antibodies by distinguishing all MCLs out of a panel of B- and T-cell non-Hodgkin lymphomas (NHLs) and remarkably did not bind nor kill normal human B lymphocytes. MCL elimination by antibody-mediated cytotoxicity was demonstrated in vitro and confirmed with significantly extended overall survival in human MCL xenograft models in vivo. Importantly, in vivo human B-cell depletion experiments on humanized mice confirmed our MCL-specific antibody exhibits no cytotoxicity against normal human B cells.

Applicants have successfully developed novel fully human antibody-based agents capable of specifically identifying and killing human MCLs. This is the first known report of a tumor-specific agent with diagnostic and clinical therapeutic indications against MCL.

Materials and Methods.

Generation of Human Antibody Phage Display Library. Human B cells were isolated from the buffy coat of 20 healthy blood donors. cDNA encoding antibody heavy (VH) and light (VL) chains variable regions was copied out of isolated B-cell mRNA. VH and VL cDNA were randomly combined to form antibody single chain variable fragments (scFv). Each scFv DNA sequence was engineered into a recombinant phage antibody system phagemid pCANTAB 5E (GE Healthcare Life Sciences Little Chalfont, UK) for expression on M13 phage according to manufacturer's direction. Phage diversity was confirmed by sequencing the scFv of >200 clones.

Phage Display Library Screen: Biopanning. The human antibody scFv phage display library underwent four rounds of biopanning. Phage were sequenced for the human antibody scFv and analyzed following each round. Phage enrichment was calculated and the predominant sequence(s) were identified.

Each biopanning round was as follows: The phage library was filtered to exclude phage binding normal human B cells. Isolated B cells from normal PBMC was incubated with the phage library. B cell bound phage were discarded and unbound phage were extracted for further biopanning. Extracted phage was incubated for competitive binding with a CD20-labeled malignant human cell line (MCL JeKo-1, ATCC, Manassas, Va.) and normal human B cells at 1:5 ratio. Phage binding the malignant line were eluted from sorted JeKo-1 cells and expanded for sequencing and subsequent biopanning. Phage were expanded in phage display competent TG1 cells (Lucigen, Middleton, Wis.) according to manufacturer's directions.

Generating Antibody Variants. The identified light chain variable region (VL) was genetically fused with murine or human IgG1 constant regions as depicted on FIG. 2A. Expression plasmids were transfected into Freestyle 293 Expression System (Thermo Fisher Scientific, Waltham, Mass.) according to manufacturer's directions. Recombinant antibodies in culture supernatant were purified by HiTrap Protein A affinity chromatography columns according to the manufacturer's directions (GE Healthcare, Marlborough, Mass.). Purified antibodies were confirmed by SDS gels.

TABLE 1

Antibody/Plasmid with corresponding gene and Accession Number.

| Antibody/Plasmid | Gene | Accession Number |
|---|---|---|
| LCmFc-Ab | CH2 and CH3 | LT160968 (SEQ ID NO: 6) |
| LC-Ab | hIgG1Fc | BC018747 (SEQ ID NO: 7) |
| (LC)$_2$-Ab | hIgG1Fc | BC018747 (SEQ ID NO: 7) |
| LCFv-Ab/Heavy | CH1, CH2, CH3 | BC073782 (SEQ ID NO: 8) |
| LCFv-Ab/Light | CL | BC110394 (SEQ ID NO: 9) |

INFORMAL SEQUENCE LISTING

SEQ ID NO: 1 (CDR L1)
SGHSTYA

SEQ ID NO: 2 (CDR L2)
INSDGSH

SEQ ID NO: 3 (CDR L3)
QTWDTGIRV

SEQ ID NO: 4 (4-4 Light Chain Variable Region DNA Sequence)
5'-CAGCCTGTGCTGACTCAATCGCCCTCTGCCTCTGCCTCCCTGGGAGCCTCGGTCAA
GCTCACCTGCACTCTGAGCAGTGGCCACAGTACATACGCCGTCGCATGGCATCAATA
CCAGCCAGAGAAGGGCCCTCGATATTTGATGAAGATTAACAGTGATGGCAGCCACA
TCAAGGCGGTCGGGATTCCTGATCGATTCTCAGGCTCCAGCTCTGGGGCTGAGCGCT
ACCTCACCATCTCCAGCCTCCAATTTGAGGATGAGGGTGACTTTTATTGTCAGACGT
GGGACACTGGCATTCGAGTGTTCGGCGGAGGGACCAAATTGACCGTCCTCGGTCAG
CCCAAGGCT-3'

SEQ ID NO: 5 (4-4 Light Chain Variable Region Protein Sequence
[CDRs in bold])
QPVLTQSPSASASLGASVKLTCTLSSGHSTYAVAWHQYQPEKGPRYLMKINSDGSHIK
AVGIPDRFSGSSSGAERYLTISSLQFEDEGDFYCQTWDTGIRVFGGGTKLTVLGQPKA SEQ ID NO: 6 (*Mus musculus* IgG2b mRNA for heavy chain, clone
Mab23.1.3)
ATGGACAGGC TTACTTCTTC ATTCCTGCTG CTGATTGTCC CTGCATATGT
CTTGTCCCAA GTTACTCTAA AAGAGTCTGG CCCTGGGATA TTGAAGCCCT
CACAGACCCT CAGTCTGACT TGTTCTTTCT CTGGGTTTTC ACTGAGCACT
TCTGGTATGG GTGTAGGCTG GATTCGTCAG CCTTCAGGGA AGGGTCTGGA
GTGGCTGGCA CACATTTGGT GGGATGATGA TAAGCACTAT AACCCATCCC
TAAAGAGCCA GCTCACAATC TCCAAGGATT CCTCCAGAAA CCAGGTTTTC
CTCAAGATCA CCAGTGTGGA CACTGCAGAT ACTGCCACTT ACTACTGTGT
TCGAAGATCC TTTTCATACG GTAGTAGCCG GGACTACTTT GACTACTGGG
GCCAAGGCAC CACTCTCACA GTCTCCTCAG CCAAAACAAC ACCCCCATCA
GTCTATCCAC TGGCCCCTGG GTGTGGAGAT ACAACTGGTT CCTCCGTGAC
TCTGGGATGC CTGGTCAAGG GCTACTTCCC TGAGTCAGTG ACTGTGACTT
GGAACTCTGG ATCCCTGTCC AGCAGTGTGC ACACCTTCCC AGCTCTCCTG
CAGTCTGGAC TCTACACTAT GAGCAGCTCA GTGACTGTCC CCTCCAGCAC
CTGGCCAAGT CAGACCGTCA CCTGCAGCGT TGCTCACCCA GCCAGCAGCA
CCACGGTGGA CAAAAAACTT GAGCCCAGCG GGCCCATTTC AACAATCAAC
CCCTGTCCTC CATGCAAGGA GTGTCACAAA TGCCCAGCTC CTAACCTCGA
GGGTGGACCA TCCGTCTTCA TCTTCCCTCC AAATATCAAG GATGTACTCA
TGATCTCCCT GACACCCAAG GTCACGTGTG TGGTGGTGGA TGTGAGCGAG
GATGACCCAG ACGTCCAGAT CAGCTGGTTT GTGAACAACG TGGAAGTACA
CACAGCTCAG ACACAAACCC ATAGAGAGGA TTACAACAGT ACTATCCGGG
TGGTCAGCAC CCTCCCCATC CAGCACCAGG ACTGGATGAG TGGCAAGGAG
TTCAAATGCA AGGTCAACAA CAAAGACCTC CCATCACCCA TCGAGAGAAC
CATCTCAAAA ATTAAAGGGC TAGTCAGAGC TCCACAAGTA TACATCTTGC
CGCCACCAGC AGAGCAGTTG TCCAGGAAAG ATGTCAGTCT CACTTGCCTG
GTCGTGGGCT TCAACCCTGG AGACATCAGT GTGGAGTGGA CCAGCAATGG
GCATACAGAG GAGAACTACA AGGACACCGC ACCAGTCCTG GACTCTGACG
GTTCTTACTT CATATATAGC AAGCTCAATA TGAAAACAAG CAAGTGGGAG
AAAACAGATT CCTTCTCATG CAACGTGAGA CACGAGGGTC TGAAAAATTA
CTACCTGAAG AAGACCATCT CCCGGTCTCC GGGTAAATGA -continued

INFORMAL SEQUENCE LISTING

SEQ ID NO: 7 (Homo sapiens immunoglobulin heavy constant
G1m marker mRNA, cDNA clone IMAGE: 4851063)
CTTAGCCCTG GACTCCAAGG CCTTTCCACT TGGTGATCAG CACTGAGCAC
AGAGGACTCA CCATGGAATT GGGGCTGAGC TGGGTTTTCC TTGTTGCTAT
TTTAGAAGGT GTCCAGTGTG AGGTGCAGCT GGTGGAGTCT GGGGGAGGCT
TGGTCCAGCC TGGGGGGTCC CTGAGACTCT CCTGTGTAGT CTCTGGATTC
ACCTTTAGTA GTTATTGGAT GAGCTGGGTC CGCCAGGCTC CAGGGAAGGG
GCTGGAGTGG GTGGCCAACA TAAAGCAAGA TGGAAGTGAG AAATACTATG
TGGACTCTGT GAAGGGCCGA TTCACCATCT CCAGAGACAA CGCCAAGAAC
TCACTGTATC TGCAAATGAA CAGCCTGAGA GCCGAGGACA CGGCTGTGTA
TTACTGTGCG AGAGATGGCA GCAGCTGGTA CAGGGACTGG TTCGACCCCT
GGGGCCAGGG AACCCTGGTC ACCGTCTCCT CAGCCTCCAC CAAGGGCCCA
TCGGTCTTCC CCCTGGCACC CTCCTCCAAG AGCACCTCTG GGGCACAGC
GGCCCTGGGC TGCCTGGTCA AGGACTACTT CCCCGAACCG GTGACGGTGT
CATGGAACTC AGGCGCCCTG ACCAGCGGCG TGCACACCTT CCCGGCTGTC
CTACAGTCCT CAGGACTCTA CTCCCTCAGC AGCGTGGTGA CCGTGCCCTC
CAGCAGCTTG GGCACCCAGA CCTACATCTG CAACGTGAAT CACAAGCCCA
GCAACACCAA GGTGGACAAG AAAGTTGAGC CCAAATCTTG TGACAAAACT
CACACATGCC CACCGTGCCC AGCACCTGAA CTCCTGGGGG GACCGTCAGT
CTTCCTCTTC CCCCCAAAAC CCAAGGACAC CCTCATGATC TCCCGGACCC
CTGAGGTCAC ATGCGTGGTG GTGGACGTGA GCCACGAAGA CCCTGAGGTC
AAGTTCAACT GGTACGTGGA CGGCGTGGAG GTGCATAATG CCAAGACAAA
GCCGCGGGAG GAGCAGTACA ACAGCACGTA CCGTGTGGTC AGCGTCCTCA
CCGTCCTGCA CCAGGACTGG CTGAATGGCA AGGAGTACAA GTGCAAGGTC
TCCAACAAAG CCCTCCCAGC CCCCATCGAG AAAACCATCT CCAAAGCCAA
AGGGCAGCCC CGAGAACCAC AGGTGTACAC CCTGCCCCCA TCCCGGGATG
AGCTGACCAA GAACCAGGTC AGCCTGACCT GCCTGGTCAA AGGCTTCTAT
CCCAGCGACA TCGCCGTGGA GTGGGAGAGC AATGGGCAGC CGGAGAACAA
CTACAAGACC ACGCCTCCCG TGCTGGACTC CGACGGCTCC TTCTTCCTCT
ACAGCAAGCT CACCGTGGAC AAGAGCAGGT GGCAGCAGGG GAACGTCTTC
TCATGCTCCG TGATGCATGA GGCTCTGCAC AACCACTACA CGCAGAAGAG
CCTCTCCCTG TCTCCGGGTA AATGAGTGCG ACGGCCGGCA AGCCCCCGCT
CCCCGGGCTC TCGCGGTCGC ACGAGGATGC TTGGCACGTA CCCCCTGTAC
ATACTTCCCG GGCGCCCAGC ATGGAAATAA AGCACCCAGC GCTGCCCTGG
GCCCCTGCGA AAAAAAAAA AAAAAAAAA AAAAAAAAA AAAAAAAAA
AAAAAAAAA AAAAAAAAA AAAAAAAA SEQ ID NO: 8 (Homo sapiens immunoglobulin heavy constant
G1m marker mRNA, cDNA clone IMAGE: 6295732)
CCCGCCCTGG GATTCCCAGG TGTTTTCATT TGGTGATCAG CACTGAACAC
AGAAGAGTCA TGATGGAGTT TGGGCTGAGC TGCGTTTTCC TTGTTGCCAT
TTTTAAAGGT GTCCACTGTG AGGTGCAGCT GGTGGAGTCT GGGGGAGGCT
TGGTCCAGCC GGGGGGGTCC CTGAGACTCT CCTGTGTAGC CTCTGCATTC
ACCCTCAGTA GGCATGCGAT GCACTGGGTC CGCCAGGCTC CAGGGAAGGG
ACTGGAATAT GTTTCAGGTA TTAGTAATAG TGAAAATAGC ACATATTATG
CAGACTCTGT GAAGGGCAGA TTCACCATCT CCAGAGACAA CTACAAGAAC
ACGCTTTATC TTCAACTGGG CAGCCTGAGA GCTGAGGACA AGGCTGTGTA
TTACTGTGCG AGAGCGAGGT GTAGAGGAGA CACATGCCTC AACTTCTACT
ACGGTTTGGA CGTCTGGGGC CAAGGGACCA CGGTCATCGT CTCCTCAGCC
TCCACCAAGG GCCCATCGGT CTTCCCCCTG GCACCCTCCT CCAAGAGCAC
CTCTGGGGGC ACAGCGGCCC TGGGCTGCCT GGTCAAGGAC TACTTCCCCG
AACCGGTGAC GGTGTCGTGG AACTCAGGCG CCCTGACCAG CGGCGTGCAC
ACCTTCCCGG CTGTCCTACA GTCCTCAGGA CTCTACTCCC TCAGCAGCGT
GGTGACCGTG CCCTCCAGCA GCTTGGGCAC CCAGACCTAC ATCTGCAACG
TGAATCACAA GCCCAGCAAC ACCAAGGTGG ACAAGAAAGT TGAGCCCAAA
TCTTGTGACA AAACTCACAC ATGCCCACCG TGCCCAGCAC CTGAACTCCT
GGGGGGACCG TCAGTCTTCC TCTTCCCCCC AAAACCCAAG GACACCCTCA
TGATCTCCCG GACCCCTGAG GTCACATGCG TGGTGGTGGA CGTGAGCCAC
GAAGACCCTG AGGTCAAGTT CAACTGGTAC GTGGACGGCG TGGAGGTGCA
TAATGCCAAG ACAAAGCCGC GGGAGGAGCA GTACAACAGC ACGTACCGTG
TGGTCAGCGT CCTCACCGTC CTGCACCAGG ACTGGCTGAA TGGCAAGGAG
TACAAGTGCA AGGTCTCCAA CAAAGCCCTC CCAGCCCCCA TCGAGAAAAC
CATCTCCAAA GCCAAAGGGC AGCCCCGAGA ACCACAGGTG TACACCCTGC
CCCCATCCCG GGATGAGCTG ACCAAGAACC AGGTCAGCCT GACCTGCCTG
GTCAAAGGCT TCTATCCCAG CGACATCGCC GTGGAGTGGG AGAGCAATGG
GCAGCCGGAG AACAACTACA AGACCACGCC TCCCGTGCTG GACTCCGACG
GCTCCTTCTT CCTCTACAGC AAGCTCACCG TGGACAAGAG CAGGTGGCAG
CAGGGGAACG TCTTCTCATG CTCCGTGATG CATGAGGCTC TGCACAACCA
CTACACGCAG AAGAGCCTCT CCCTGTCTCC GGGTAAATGA GTGCGACGGC
CGGCAAGCCC CCGCTCCCCA GGCTCTCGGG GTCGCGCGAG GATGCTTGGC
ACGTACCCCG TGTACATACT TCCCGGGCGC CCAGCATGGA AATAAAGCAC
CCAGCGCTGC CCTGGGCCCC TGCAAAAAAA AAAAAAAAA A

INFORMAL SEQUENCE LISTING

SEQ ID NO: 9 (Homo sapiens immunoglobulin kappa constant
mRNA, cDNA clone IMAGE: 5215019)
```
GGACTCCTCA GTTCACCTTC TCACAATGAG GCTCCCTGCT CAGCTCCTGG
GGCTGCTAAT GCTCTGGGTC CCAGGATCCA GTGGGGATGT TGTGATGACT
CAGTCTCCAC TCTCCCTGCC CGTCACCCTT GGACAGCCGG CCTCCATCTC
CTGCAGGTCT AGTCAAAGCC TCGTATACAG TGATGGAAAC ACCTACTTGA
ATTGGTTTCA GCAGAGGCCA GGCCAATCTC CAAGGCGCCT AATTTATAAG
GTTTCTATCC GGGACTCTGG GGTCCCAGAC AAATTCAGCG GCAGTGGGTC
AGGCACTGAT TTCACACTGA AAATCAGCAG GGTGGAGGCT GAGGATGTTG
GGGTTTATTA CTGCATGCAA GGTTCACACT GGCCTCCGAT CACCTTCGGC
CAAGGGACAC GACTGGAGAT TAAACGAACT GTGGCTGCAC CATCTGTCTT
CATCTTCCCG CCATCTGATG AGCAGTTGAA ATCTGGAACT GCCTCTGTTG
TGTGCCTGCT GAATAACTTC TATCCCAGAG AGGCCAAAGT ACAGTGGAAG
GTGGATAACG CCCTCCAATC GGGTAACTCC CAGGAGAGTG TCACAGAGCA
GGACAGCAAG GACAGCACCT ACAGCCTCAG CAGCACCCTG ACGCTGAGCA
AAGCAGACTA CGAGAAACAC AAAGTCTACG CCTGCGAAGT CACCCATCAG
GGCCTGAGCT CGCCCGTCAC AAAGAGCTTC AACAGGGGAG AGTGTTAGAG
GGAGAAGTGC CCCCACCTGC TCCTCAGTTC CAGCCTGACC CCCTCCCATC
CTTTGGCCTC TGACCCTTTT TCCACAGGGG ACCTACCCCT ATTGCGGTCC
TCCAGCTCAT CTTTCACCTC ACCCCCCTCC TCCTCCTTGG CTTTAATTAT
GCTAATGTTG GAGGAGAATG AATAAATAAA GTGAATCTTT GCAAAAAAAA
AAAAAAAAAA AAAAAAAAAA AAAAAAAAA AAAAAA
```

Embodiments

Embodiment 1. An antibody variable domain comprising a CDR 1 as set forth in SEQ ID NO:1, a CDR 2 as set forth in SEQ ID NO:2 and a CDR 3 as set forth in SEQ ID NO:3.

Embodiment 2. An antibody construct comprising a first antibody peptide, said first antibody peptide comprising: (i) a first antibody variable domain comprising a CDR 1 as set forth in SEQ ID NO:1, a CDR 2 as set forth in SEQ ID NO:2 and a CDR 3 as set forth in SEQ ID NO:3; and (ii) a first antibody domain bound to said first antibody variable domain.

Embodiment 3. The antibody variable domain of embodiment 1 or the antibody construct of embodiment 2, wherein said antibody variable domain is an antibody light chain variable domain.

Embodiment 4. The antibody variable domain of embodiment 1 or the antibody construct of embodiment 2, wherein said antibody variable domain is an antibody heavy chain variable domain.

Embodiment 5. The antibody construct of one of embodiments 2-4, wherein said antibody construct is a monovalent antibody construct.

Embodiment 6. The antibody construct of one of embodiments 2-5, wherein said first antibody domain is a first variable heavy chain domain.

Embodiment 7. The antibody construct of embodiment 6, wherein said antibody construct is a single chain antibody (scFv).

Embodiment 8. The antibody construct of embodiment 2, wherein said first antibody domain is a first constant heavy chain.

Embodiment 9. The antibody construct of embodiment 8, wherein said first constant heavy chain comprises a first constant heavy chain 2 (CH2) domain bound to a first constant heavy chain 3 (CH3) domain.

Embodiment 10. The antibody construct of embodiment 9, wherein said first CH3 domain is bound to said first antibody variable domain through said first CH2 domain.

Embodiment 11. The antibody construct of embodiment 10, wherein said first antibody peptide further comprises a first constant heavy chain 1 (CH1) domain.

Embodiment 12. The antibody construct of embodiment 11, wherein said first $CH_1$ domain forms part of said first antibody domain.

Embodiment 13. The antibody construct of one of embodiments 11-12, wherein said first antibody variable domain is bound to said first antibody domain through said first $CH_1$ domain.

Embodiment 14. The antibody construct of one of embodiments 11-13, wherein said first antibody variable domain is bound to said first $CH_2$ domain through said first $CH_1$ domain.

Embodiment 15. The antibody construct of one of embodiments 2-14, wherein said antibody construct is a divalent antibody construct further comprising a second antibody peptide bound to said first antibody peptide.

Embodiment 16. The antibody construct of embodiment 15, wherein said second peptide is bound to said first antibody domain.

Embodiment 17. The antibody construct of embodiment 15, wherein said second antibody peptide is bound to said first $CH_2$ domain.

Embodiment 18. The antibody construct of one of embodiments 15-17, wherein said second antibody peptide and said first antibody peptide are chemically identical.

Embodiment 19. The antibody construct of one of embodiments 15-17, wherein said second antibody peptide and said first antibody peptide are chemically different.

Embodiment 20. The antibody construct of one of embodiments 15-17, wherein said second antibody peptide comprises: (i) a second antibody variable domain; and (ii) a second antibody domain bound to said second antibody variable domain.

Embodiment 21. The antibody construct of embodiment 20, wherein said second antibody variable domain comprises a CDR 1 as set forth in SEQ ID NO:1, a CDR 2 as set forth in SEQ ID NO:2 and a CDR 3 as set forth in SEQ ID NO:3.

Embodiment 22. The antibody construct of embodiment 20 or 21, wherein said second antibody domain is a second constant heavy chain.

Embodiment 23. The antibody construct of embodiment 22, wherein said second constant heavy chain comprises a second constant heavy chain 2 (CH$_2$) domain bound to a second constant heavy chain 3 (CH$_3$) domain.

Embodiment 24. The antibody construct of embodiment 23, wherein said second CH$_3$ domain is bound to said second antibody variable domain through said second CH$_2$ domain.

Embodiment 25. The antibody construct of embodiment 24, wherein said second antibody peptide further comprises a second constant heavy chain 1 (CH$_1$) domain.

Embodiment 26. The antibody construct of embodiment 25, wherein said second CH$_1$ domain forms part of said second antibody domain.

Embodiment 27. The antibody construct of one of embodiments 25-26, wherein said second antibody variable domain is bound to said second antibody domain through said second CH$_1$ domain.

Embodiment 28. The antibody construct of one of embodiments 25-27, wherein said second antibody variable domain is bound to said second CH$_2$ domain through said second CH$_1$ domain.

Embodiment 29. The antibody construct of embodiment 28, wherein said first CH$_1$ domain and said second CH$_1$ domain are bound together.

Embodiment 30. The antibody construct of embodiment 15-29, wherein said antibody construct is a tetravalent antibody construct further comprising a third antibody variable domain bound to said first antibody peptide and a fourth antibody variable domain bound to said second antibody peptide.

Embodiment 31. The antibody construct of embodiment 30, wherein said third antibody variable domain forms part of said first antibody peptide and said fourth antibody variable domain forms part of said second antibody peptide.

Embodiment 32. The antibody construct of embodiment 30 or 31, wherein said third antibody variable domain is bound to said first antibody domain through said first antibody variable domain.

Embodiment 33. The antibody construct of one of embodiments 30-32, wherein said third antibody variable domain is bound to said first CH$_2$ domain through said first antibody variable domain.

Embodiment 34. The antibody construct of one of embodiments 30-33, wherein said fourth antibody variable domain is bound to said second antibody domain through said second antibody variable domain.

Embodiment 35. The antibody construct of one of embodiments 30-34, wherein said fourth antibody variable domain is bound to said second CH$_2$ domain through said second antibody variable domain.

Embodiment 36. The antibody construct of embodiment 30, wherein said third antibody variable domain forms part of a first light chain antibody peptide bound to said first antibody peptide and said fourth antibody variable domain forms part of a second light chain antibody peptide bound to said second antibody peptide.

Embodiment 37. The antibody construct of embodiment 36, wherein said first light chain antibody peptide comprises a first constant light chain 1 (CL1) domain bound to said third antibody variable domain.

Embodiment 38. The antibody construct of embodiment 37, wherein said first light chain antibody peptide is bound to said first antibody peptide through said first CL1 domain.

Embodiment 39. The antibody construct of embodiment 37 or 38, wherein said third antibody variable domain is bound to said first antibody peptide through said first CL1 domain.

Embodiment 40. The antibody construct of one of embodiments 36-39, wherein said second light chain antibody peptide further comprises a second constant light chain 1 (CL1) domain bound to said fourth antibody variable domain.

Embodiment 41. The antibody construct of embodiment 40, wherein said second light chain antibody peptide is bound to said second antibody peptide through said second CL1 domain.

Embodiment 42. The antibody construct of embodiment 37 or 38, wherein said fourth antibody variable domain is bound to said second antibody peptide through said second CL1 domain.

Embodiment 43. The antibody construct of one of embodiments 2-42, wherein said antibody construct is an antibody.

Embodiment 44. The antibody construct of one of embodiments 2-42, wherein said antibody construct is an antibody variant.

Embodiment 45. The antibody construct of one of embodiments 2-42, wherein said antibody construct is a Fab' fragment.

Embodiment 46. The antibody construct of one of embodiments 2-42, wherein said antibody construct is a chimeric antibody.

Embodiment 47. The antibody construct of one of embodiments 2-42, wherein said antibody construct is a humanized antibody.

Embodiment 48. The antibody construct of one of embodiments 2-42, wherein said antibody construct is a human antibody.

Embodiment 49. The antibody construct of one of embodiments 2-48, wherein said antibody construct comprises a detectable moiety.

Embodiment 50. The antibody construct of embodiment 49, wherein said detectable moiety is a fluorescent moiety.

Embodiment 51. The antibody construct of one of embodiments 2-50, wherein said antibody construct is bound to a cancer protein.

Embodiment 52. The antibody construct of one of embodiments 2-51, wherein said cancer protein forms part of a cancer cell.

Embodiment 53. The antibody construct of embodiment 52, wherein said cancer cell is a lymphoid cell.

Embodiment 54. The antibody construct of embodiment 52 or 53, wherein said cancer cell is a B cell.

Embodiment 55. An isolated nucleic acid encoding said antibody variable domain of embodiment 1, said first antibody peptide of one of embodiments 2-54, said second antibody peptide of one of embodiments 15-54, said first light chain antibody peptide of one of embodiments 36-54 or said second light chain antibody peptide of one of embodiments 36-54.

Embodiment 56. A pharmaceutical composition comprising a therapeutically effective amount of said antibody variable domain of embodiment 1 or said antibody construct of one of embodiments 2-54 and a pharmaceutically acceptable excipient.

Embodiment 57. A method of treating cancer in a subject in need thereof, said method comprising administering to a subject a therapeutically effective amount of said antibody variable domain of embodiment 1 or said antibody construct of one of embodiments 2-54, thereby treating cancer in said subject.

Embodiment 58. The method of embodiment 57, wherein said cancer is lymphoma, leukemia or myeloma.

Embodiment 59. The method of embodiment 58, wherein said lymphoma is mantle cell lymphoma, follicular lymphoma, diffuse large B-cell lymphoma, marginal zone lymphoma or Burkitt's lymphoma.

Embodiment 60. The method of embodiment 58, wherein said leukemia is lymphoblastic leukemia, chronic lymphocytic leukemia or hairy cell leukemia.

Embodiment 61. The method of one of embodiments 57-60, said method further comprising administering to said subject a second therapeutic agent.

What is claimed is:

1. An antibody light chain variable domain comprising SEQ ID NO:5.

2. An antibody construct comprising a first antibody peptide, said first antibody peptide comprising:
   (i) a first antibody light chain variable domain comprising SEQ ID NO: 5; and
   (ii) a first antibody domain bound to said first antibody light chain variable domain.

3. The antibody construct of claim 2, wherein said first antibody domain is a first constant heavy chain.

4. The antibody construct of claim 3, wherein said first constant heavy chain comprises a first constant heavy chain 2 (CH2) domain bound to a first constant heavy chain 3 (CH3) domain.

5. The antibody construct of claim 2, wherein said antibody construct is a divalent antibody construct further comprising a second antibody peptide bound to said first antibody peptide.

6. The antibody construct of claim 5, wherein said second antibody peptide and said first antibody peptide are chemically identical.

7. The antibody construct of claim 5, wherein said second antibody peptide and said first antibody peptide are chemically different.

8. The antibody construct of claim 5, wherein said second antibody peptide comprises:
   (i) a second antibody light chain variable domain comprising SEQ ID NO:5; and
   (ii) a second antibody domain bound to second antibody light chain variable domain.

9. The antibody construct of claim 8, wherein said antibody construct is a tetravalent antibody construct further comprising a third antibody light chain variable domain bound to said first antibody peptide and a fourth antibody light chain variable domain bound to said second antibody peptide.

10. The antibody construct of claim 9, wherein said third antibody light chain variable domain forms part of said first antibody peptide and said fourth antibody light chain variable domain forms part of said second antibody peptide.

11. The antibody construct of claim 9, wherein said third antibody light chain variable domain forms part of a first light chain antibody peptide bound to said first antibody peptide and said fourth antibody light chain variable domain forms part of a second light chain antibody peptide bound to said second antibody peptide.

12. The antibody construct of claim 2, wherein said antibody construct is a human antibody.

13. An isolated nucleic acid encoding said antibody light chain variable domain of claim 1, said first antibody peptide of claim 2, said second antibody peptide of claim 5, said first light chain antibody peptide of claim 11 or said second light chain antibody peptide of claim 11.

14. A pharmaceutical composition comprising a therapeutically effective amount of said antibody light chain variable domain of claim 1 or said antibody construct of claim 2 and a pharmaceutically acceptable excipient.

15. A method of treating mantle cell lymphoma in a subject in need thereof, said method comprising administering to a subject a therapeutically effective amount of said antibody construct of claim 2, thereby treating mantle cell lymphoma in said subject.

16. The method of claim 15, wherein said first antibody domain bound to said first antibody light chain variable domain is a first constant heavy chain that comprises a first constant heavy chain 2 (CH2) domain bound to a first constant heavy chain 3 (CH3) domain.

* * * * *

UNITED STATES PATENT AND TRADEMARK OFFICE
CERTIFICATE OF CORRECTION

Page 1 of 1

PATENT NO. : 11,597,774 B2
APPLICATION NO. : 16/610868
DATED : March 7, 2023
INVENTOR(S) : Hong Qin et al.

It is certified that error appears in the above-identified patent and that said Letters Patent is hereby corrected as shown below:

In the Claims

At Column 68, Claim number 13, Line number 33, please delete "of claim 2, said second antibody peptide of claim 5, said first" and insert -- of claim 2, said second antibody peptide of claim 8, said first --.

Signed and Sealed this
Twenty-third Day of May, 2023

Katherine Kelly Vidal
*Director of the United States Patent and Trademark Office*

SEQUENCE LISTING

```
<160> NUMBER OF SEQ ID NOS: 9

<210> SEQ ID NO 1
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 1

Ser Gly His Ser Thr Tyr Ala
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 2

Ile Asn Ser Asp Gly Ser His
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Gln Thr Trp Asp Thr Gly Ile Arg Val
1               5

<210> SEQ ID NO 4
<211> LENGTH: 348
<212> TYPE: DNA
<213> ORGANISM: Artificial Sequence
<220> FEATURE:
<223> OTHER INFORMATION: Synthetic polynucleotide

<400> SEQUENCE: 4
cagcctgtgc tgactcaatc gccctctgcc tctgcctccc tgggagcctc ggtcaagctc      60
acctgcactc tgagcagtgg ccacagtaca tacgccgtcg catggcatca ataccagcca     120
gagaagggcc ctcgatattt gatgaagatt aacagtgatg gcagccacat caaggcggtc     180
gggattcctg atcgattctc aggctccagc tctggggctg agcgctacct caccatctcc     240
agcctccaat ttgaggatga gggtgacttt tattgtcaga cgtgggacac tggcattcga     300
gtgttcggcg gagggaccaa attgaccgtc ctcggtcagc ccaaggct                  348

<210> SEQ ID NO 5
<211> LENGTH: 116
<212> TYPE: PRT
<213> ORGANISM: Artificial sequence
<220> FEATURE:
<223> OTHER INFORMATION: Synthetic polypeptide
```

<400> SEQUENCE: 5

```
Gln Pro Val Leu Thr Gln Ser Pro Ser Ala Ser Ala Ser Leu Gly Ala
1               5                   10                  15

Ser Val Lys Leu Thr Cys Thr Leu Ser Ser Gly His Ser Thr Tyr Ala
            20                  25                  30

Val Ala Trp His Gln Tyr Gln Pro Glu Lys Gly Pro Arg Tyr Leu Met
        35                  40                  45

Lys Ile Asn Ser Asp Gly Ser His Ile Lys Ala Val Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Phe Glu Asp Glu Gly Asp Phe Tyr Cys Gln Thr Trp Asp
                85                  90                  95

Thr Gly Ile Arg Val Phe Gly Gly Gly Thr Lys Leu Thr Val Leu Gly
            100                 105                 110

Gln Pro Lys Ala
        115
```

<210> SEQ ID NO 6
<211> LENGTH: 1440
<212> TYPE: DNA
<213> ORGANISM: Mus musculus

<400> SEQUENCE: 6

```
atggacaggc ttacttcttc attcctgctg ctgattgtcc ctgcatatgt cttgtcccaa      60
gttactctaa aagagtctgg ccctgggata ttgaagccct cacagaccct cagtctgact     120
tgttctttct ctgggttttc actgagcact tctggtatgg gtgtaggctg gattcgtcag    180
ccttcaggga agggtctgga gtggctggca cacatttggt gggatgatga taagcactat    240
aacccatccc taagagccca gctcacaatc tccaaggatt cctccagaaa ccaggttttc    300
ctcaagatca ccagtgtgga cactgcagat actgccactt actactgtgt tcgaagatcc    360
ttttcatacg gtagtagccg ggactacttt gactactggg gccaaggcac cactctcaca    420
gtctcctcag ccaaaacaac ccccccatca gtctatccac tggcccctgg gtgtggagat    480
acaactggtt cctccgtgac tctgggatgc ctggtcaagg gctacttccc tgagtcagtg    540
actgtgactt ggaactctgg atccctgtcc agcagtgtgc acaccttccc agctctcctg    600
cagtctggac tctacactat gagcagctca gtgactgtcc cctccagcac ctggccaagt    660
cagaccgtca cctgcagcgt tgctcaccca gccagcagca ccgtggagga caaaaaactt    720
gagcccagcg ggcccatttc aacaatcaac cctgtcctc catgcaagga gtgtcacaaa    780
tgcccagctc ctaacctcga gggtggacca tccgtcttca tcttccctcc aaatatcaag    840
gatgtactca tgatctccct gacacccaag gtcacgtgtg tggtggtgga tgtgagcgag    900
gatgacccag acgtccagat cagctggttt gtgaacaacg tggaagtaca cacagctcag    960
acacaaaccc atagagagga ttacaacagt actatccggg tggtcagcac cctccccatc   1020
cagcaccagg actggatgag tggcaaggag ttcaaatgca aggtcaacaa caaagacctc   1080
ccatcaccca tcgagagaac catctcaaaa attaaagggc tagtcagagc tccacaagta   1140
tacatcttgc cgccaccagc agagcagttg tccaggaaag atgtcagtct cacttgcctg   1200
gtcgtgggct tcaaccctgg agacatcagt gtggagtgga ccagcaatgg catacagag   1260
gagaactaca ggacaccgc accagtcctg gactctgacg gttcttactt catatatagc   1320
aagctcaata tgaaaacaag caagtgggag aaaacagatt ccttctcatg caacgtgaga   1380
```

```
cacgagggtc tgaaaaatta ctacctgaag aagaccatct cccggtctcc gggtaaatga    1440
```

<210> SEQ ID NO 7
<211> LENGTH: 1679
<212> TYPE: DNA
<213> ORGANISM: Homo sapiens

<400> SEQUENCE: 7

```
cttagccctg gactccaagg cctttccact tggtgatcag cactgagcac agaggactca      60
ccatggaatt ggggctgagc tgggttttcc ttgttgctat tttagaaggt gtccagtgtg     120
aggtgcagct ggtggagtct gggggaggct tggtccagcc tggggggtcc ctgagactct     180
cctgtgtagt ctctggattc acctttagta gttattggat gagctgggtc cgccaggctc     240
cagggaaggg gctggagtgg gtggccaaca taaagcaaga tggaagtgag aaatactatg     300
tggactctgt gaagggccga ttcaccatct ccagagacaa cgccaagaac tcactgtatc     360
tgcaaatgaa cagcctgaga gccgaggaca cggctgtgta ttactgtgcg agagatggca     420
gcagctggta cagggactgg ttcgacccct ggggccaggg aaccctggtc accgtctcct     480
cagcctccac caagggccca tcggtcttcc cctggcacc  ctcctccaag agcacctctg     540
ggggcacagc ggccctgggc tgcctggtca aggactactt ccccgaaccg gtgacggtgt     600
catggaactc aggcgccctg accagcggcg tgcacacctt cccggctgtc ctacagtcct     660
caggactcta ctccctcagc agcgtggtga ccgtgccctc cagcagcttg ggcacccaga     720
cctacatctg caacgtgaat cacaagccca gcaacaccaa ggtggacaag aaagttgagc     780
ccaaatcttg tgacaaaact cacacatgcc caccgtgccc agcacctgaa ctcctggggg     840
gaccgtcagt cttcctcttc cccccaaaac ccaaggacac cctcatgatc tcccggaccc     900
ctgaggtcac atgcgtggtg gtggacgtga gccacgaaga ccctgaggtc aagttcaact     960
ggtacgtgga cggcgtggag gtgcataatg ccaagacaaa gccgcgggag gagcagtaca    1020
acagcacgta ccgtgtggtc agcgtcctca ccgtcctgca ccaggactgg ctgaatggca    1080
aggagtacaa gtgcaaggtc tccaacaaag ccctcccagc ccccatcgag aaaaccatct    1140
ccaaagccaa agggcagccc cgagaaccac aggtgtacac cctgccccca tcccgggatg    1200
agctgaccaa gaaccaggtc agcctgacct gcctggtcaa aggcttctat cccagcgaca    1260
tcgccgtgga gtgggagagc aatgggcagc cggagaacaa ctacaagacc acgcctcccg    1320
tgctggactc cgacggctcc ttcttcctct acagcaagct caccgtggac aagagcaggt    1380
ggcagcaggg gaacgtcttc tcatgctccg tgatgcatga ggctctgcac aaccactaca    1440
cgcagaagag cctctccctg tctccgggta aatgagtgcg acggccggca agccccgct    1500 cccgggctc tcgcggtcgc acgaggatgc ttggcacgta cccctgtac atacttcccg    1560 ggcgcccagc atggaaataa agcacccagc gctgccctgg gccctgcga aaaaaaaaa    1620 aaaaaaaaa aaaaaaaaa aaaaaaaaa aaaaaaaaa aaaaaaaaa aaaaaaa          1679
```

<210> SEQ ID NO 8
<211> LENGTH: 1641
<212> TYPE: DNA
<213> ORGANISM: Homo sapiens

<400> SEQUENCE: 8

```
cccgccctgg gattcccagg tgttttcatt tggtgatcag cactgaacac agaagagtca      60
tgatggagtt tgggctgagc tgcgttttcc ttgttgccat ttttaaaggt gtccactgtg     120
```

```
aggtgcagct ggtggagtct gggggaggct tggtccagcc ggggggtcc ctgagactct      180 cctgtgtagc ctctgcattc accctcagta ggcatgcgat gcactgggtc cgccaggctc      240
cagggaaggg actggaatat gtttcaggta ttagtaatag tgaaaatagc acatattatg      300
cagactctgt gaagggcaga ttcaccatct ccagagacaa ctacaagaac acgctttatc      360
ttcaactggg cagcctgaga gctgaggaca aggctgtgta ttactgtgcg agagcgaggt      420
gtagaggaga cacatgcctc aacttctact acggtttgga cgtctggggc caagggacca      480
cggtcatcgt ctcctcagcc tccaccaagg gcccatcggt cttccccctg gcaccctcct      540
ccaagagcac ctctgggggc acagcggccc tgggctgcct ggtcaaggac tacttccccg      600
aaccggtgac ggtgtcgtgg aactcaggcg ccctgaccag cggcgtgcac accttcccgg      660
ctgtcctaca gtcctcagga ctctactccc tcagcagcgt ggtgaccgtg ccctccagca      720
gcttgggcac ccagacctac atctgcaacg tgaatcacaa gcccagcaac accaaggtgg      780
acaagaaagt tgagcccaaa tcttgtgaca aaactcacac atgcccaccg tgcccagcac      840
ctgaactcct ggggggaccg tcagtcttcc tcttccccccc aaaacccaag gacaccctca      900
tgatctcccg gacccctgag gtcacatgcg tggtggtgga cgtgagccac gaagaccctg      960
aggtcaagtt caactggtac gtggacggcg tggaggtgca taatgccaag acaaagccgc     1020
gggaggagca gtacaacagc acgtaccgtg tggtcagcgt cctcaccgtc ctgcaccagg     1080
actggctgaa tggcaaggag tacaagtgca aggtctccaa caaagccctc ccagccccca     1140
tcgagaaaac catctccaaa gccaagggc agccccgaga accacaggtg tacaccctgc     1200
ccccatcccg ggatgagctg accaagaacc aggtcagcct gacctgcctg gtcaaaggct     1260
tctatcccag cgacatcgcc gtggagtggg agagcaatgg gcagccggag aacaactaca     1320
agaccacgcc tcccgtgctg gactccgacg gctccttctt cctctacagc aagctcaccg     1380
tggacaagag caggtggcag caggggaacg tcttctcatg ctccgtgatg catgaggctc     1440
tgcacaacca ctacacgcag aagagcctct ccctgtctcc gggtaaatga gtgcgacggc     1500
cggcaagccc ccgctcccca ggctctcggg gtcgcgcgag gatgcttggc acgtaccccg     1560
tgtacatact tcccgggcgc ccagcatgga aataaagcac ccagcgctgc cctgggcccc     1620
tgcaaaaaaa aaaaaaaaaa a                                              1641

<210> SEQ ID NO 9
<211> LENGTH: 986
<212> TYPE: DNA
<213> ORGANISM: Homo sapiens

<400> SEQUENCE: 9
ggactcctca gttcaccttc tcacaatgag gctccctgct cagctcctgg ggctgctaat       60
gctctgggtc ccaggatcca gtggggatgt tgtgatgact cagtctccac tctccctgcc      120
cgtcacccrt ggacagccgg cctccatctc ctgcaggtct agtcaaagcc tcgtatacag      180
tgatggaaac acctacttga attggtttca gcagaggcca ggccaatctc caaggcgcct      240
aatttataag gtttctatcc gggactctgg ggtcccagac aaattcagcg gcagtgggtc      300
aggcactgat ttcacactga aaatcagcag ggtggaggct gaggatgttg ggglttatta      360 ctgcatgcaa ggttcacact ggcctccgat caccttcggc caagggacac gactggagat      420
taaacgaact gtggctgcac catctgtctt catcttcccg ccatctgatg agcagttgaa      480
atctggaact gcctctgttg tgtgcctgct gaataacttc tatcccagag aggccaaagt      540
acagtggaag gtggataacg cccctccaatc gggtaactcc caggagagtg tcacagagca      600
```

```
ggacagcaag gacagcacct acagcctcag cagcaccctg acgctgagca aagcagacta    660
cgagaaacac aaagtctacg cctgcgaagt cacccatcag ggcctgagct cgcccgtcac    720
aaagagcttc aacaggggag agtgttagag ggagaagtgc ccccacctgc tcctcagttc    780
cagcctgacc ccctcccatc ctttggcctc tgacccttt  tccacagggg acctacccct    840
attgcggtcc tccagctcat ctttcacctc accccctcc  tcctccttgg ctttaattat    900
gctaatgttg gaggagaatg aataaataaa gtgaatcttt gcaaaaaaaa aaaaaaaaaa    960
aaaaaaaaaa aaaaaaaaa aaaaaa                                          986
```